United States Patent
Herzlinger

(10) Patent No.: US 11,806,397 B2
(45) Date of Patent: Nov. 7, 2023

(54) METHODS, SYSTEMS, AND APPARATUS FOR ADMINISTERING A MONOCLONAL AND/OR POLYCLONAL ANTIBODY TREATMENT VIA RAPID INFUSION

(71) Applicant: Regina E. Herzlinger, Belmont, MA (US)

(72) Inventor: Regina E. Herzlinger, Belmont, MA (US)

( * ) Notice: Subject to any disclaimer, the term of this patent is extended or adjusted under 35 U.S.C. 154(b) by 0 days.

(21) Appl. No.: 17/589,068

(22) Filed: Jan. 31, 2022

(65) Prior Publication Data

US 2022/0193236 A1 Jun. 23, 2022

Related U.S. Application Data

(63) Continuation of application No. 17/558,295, filed on Dec. 21, 2021.
(Continued)

(51) Int. Cl.
*A61K 39/395* (2006.01)
*A61M 5/142* (2006.01)
(Continued)

(52) U.S. Cl.
CPC ......... *A61K 39/3955* (2013.01); *A61M 5/002* (2013.01); *A61M 5/1413* (2013.01);
(Continued)

(58) Field of Classification Search
CPC .. A61K 39/00; A61K 39/395; A61K 39/3955; A61M 5/002; A61M 5/1413; A61M 5/14244; A61M 5/152; A61M 5/162; A61M 5/165; A61M 5/16813; A61M 5/16881; A61M 5/14; A61M 5/142; A61M 5/145; A61M 5/148; A61M 5/16804; A61M 5/168; A61M 5/16877
See application file for complete search history.

(56) References Cited

U.S. PATENT DOCUMENTS 5,319,170 A 6/1994 Cassidy
5,366,346 A 11/1994 Danby
(Continued)

FOREIGN PATENT DOCUMENTS

WO WO-2020/084375 A1 4/2020
WO WO-2022/140463 A1 6/2022

OTHER PUBLICATIONS

AIS Health, Rezurock is approved with more transplant agents in pipeline, Member: RADAR on Drug Benefits, 8 pages, (Jul. 22, 2021).
(Continued)

*Primary Examiner* — Jason E Flick
(74) *Attorney, Agent, or Firm* — William R. Haulbrook; Peter A. Flynn; Samuel E. Bliesner

(57) ABSTRACT

Presented herein are methods, systems, and apparatus for administering a monoclonal and/or polyclonal antibody treatment via a rapid infusion device, e.g., for the treatment of a disease, e.g., a disease caused by a pathogen, e.g., for the treatment of COVID-19, caused by the virus SARS-CoV-2, or for the treatment of other conditions/diseases, such as neurological diseases, organ and/or tissue transplants, or certain forms of cancer, that require infusions of monoclonal and/or polyclonal antibodies.

28 Claims, 3 Drawing Sheets

Related U.S. Application Data

(60) Provisional application No. 63/286,353, filed on Dec. 6, 2021, provisional application No. 63/280,953, filed on Nov. 18, 2021, provisional application No. 63/253,790, filed on Oct. 8, 2021, provisional application No. 63/249,299, filed on Sep. 28, 2021, provisional application No. 63/227,803, filed on Jul. 30, 2021, provisional application No. 63/223,921, filed on Jul. 20, 2021, provisional application No. 63/220,854, filed on Jul. 12, 2021, provisional application No. 63/129,401, filed on Dec. 22, 2020.

(51) Int. Cl.
*A61M 5/162* (2006.01)
*A61M 5/14* (2006.01)
*A61M 5/168* (2006.01)
*A61M 5/152* (2006.01)
*A61M 5/165* (2006.01)
*A61M 5/00* (2006.01)

(52) U.S. Cl.
CPC ........ *A61M 5/14244* (2013.01); *A61M 5/152* (2013.01); *A61M 5/162* (2013.01); *A61M 5/165* (2013.01); *A61M 5/16813* (2013.01); *A61M 5/16881* (2013.01)

(56) References Cited

U.S. PATENT DOCUMENTS

| | | | |
|---|---|---|---|
| 6,175,688 | B1 | 1/2001 | Cassidy et al. |
| 6,236,809 | B1 | 5/2001 | Cassidy et al. |
| 6,480,257 | B2 | 11/2002 | Cassidy et al. |
| 7,819,875 | B2 | 10/2010 | Chana |
| 9,737,672 | B2 | 8/2017 | Landy et al. |
| 10,293,099 | B2 | 5/2019 | Woolford |
| 10,485,936 | B2 | 11/2019 | Landy, III et al. |
| 10,822,379 | B1 * | 11/2020 | Dimitrov .............. C07K 14/005 |
| 10,995,137 | B2 * | 5/2021 | Pedersen ............ G01N 33/6896 |
| 2002/0016570 | A1 * | 2/2002 | Cartledge ............. A61M 5/142 604/131 |
| 2004/0009216 | A1 * | 1/2004 | Rodrigueza ................ A61P 9/06 424/450 |
| 2009/0162353 | A1 * | 6/2009 | Johnson ............... C07K 16/081 424/139.1 |
| 2009/0192446 | A1 * | 7/2009 | Landy, III ......... A61M 5/16881 137/12 |
| 2013/0216742 | A1 * | 8/2013 | DeMartino ............ A61J 1/1468 428/34.4 |
| 2016/0355589 | A1 * | 12/2016 | Williams ........... C07K 16/2803 |
| 2021/0246226 | A1 * | 8/2021 | Baum .................... C07K 16/40 |
| 2021/0284732 | A1 * | 9/2021 | Zugmaier .......... C07K 16/2878 |
| 2022/0088075 | A1 | 3/2022 | O'Rourke et al. |
| 2022/0193235 | A1 | 6/2022 | Herzlinger |

OTHER PUBLICATIONS

Anderson, T.S. et al., Uptake of Outpatient Monoclonal Antibody Treatments for COVID-19 in the United States: a Cross-Sectional Analysis, J Gen. Intern. Med., 36(12):3922-3924 (2021).
Bariola, J.R. et al., Impact of Bamlanivimab Monoclonal Antibody Treatment on Hospitalization and Mortality Among Nonhospitalized Adults With Severe Acute Respiratory Syndrome Coronavirus 2 Infection, Open Forum Infectious Diseases, 8(7):ofab254 (2021).
Barnard, J.G. et al., Subvisible particle counting provides a sensitive method of detecting and quantifying aggregation of monoclonal antibody caused by freeze-thawing: insights into the roles of particles in the protein aggregation pathway, J. Pharm. Sci., 100(2):492-503 (2011).
Berrill, A. et al., Product quality during manufacture and supply, Peptide and Protein Delivery, Academic Press, pp. 313-339, (2011).
Bozzette, S.A. et al., Cardiovascular and cerebrovascular events in patients treated for human immunodeficiency virus infection. N. Engl. J. Med., 348(8):702-710 (2003).
Bril, V. et al., Efficacy and Safety of Rozanolixizumab in Moderate to Severe Generalized Myasthenia Gravis: A Phase 2 Randomized Control Trial, Neurology, 96(6):e853-e865 (2021).
Buntz, B., 50 of 2020's best-selling pharmaceuticals, Drug Discovery and Development, 6 pages, (May 14, 2021), retrieved online at: https://www.drugdiscoverytrends.com/50-of-2020s-best-selling-pharmaceuticals/.
Castaneda, R., Oral Covid-19 drugs: Merck's molnupiravir and its closest rivals, Clinical Trials Arena, 12 pages, (2021), retrieved online at: https://www.clinicaltrialsarena.com/analysis/oral-covid-19-drugs-molnupiravir/.
Centers for Medicare and Medicaid Services, CMS Increases Medicare Payment for COVID-19 Monoclonal Antibody Infusions, 2 pages, (2021), retrieved online at: https://www.cms.gov/newsroom/press-releases/cms-increases-medicare-payment-covid-19-monoclonal-antibody-infusions.
Chi, E.Y., et al., Physical stability of proteins in aqueous solution: mechanism and driving forces in nonnative protein aggregation, Pharm. Res., 20(9):1325-1336 (2003).
clinicaltrials.gov, A Study to Evaluate Safety, Tolerability, and Efficacy of Lecanemab in Subjects with Early Alzheimer's Disease, 11 pages, (2020), retrieved online at: https://clinicaltrials.gov/ct2/show/NCT01767311.
Cohen, M.S. et al. Effect of Bamlanivimab vs Placebo on Incidence of COVID-19 Among Residents and Staff of Skilled Nursing and Assisted Living Facilities: A Randomized Clinical Trial, JAMA, 326(1):46-55 (2021).
Creative Biolabs Therapeutics, Antibody Stability Analysis, (2022), retrieved online at: https://www.creative-biolabs.com/drug-discovery/therapeutics/antibody-stability-analysis.htm.
Dirks, N.L. and Meibohm, B., Population pharmacokinetics of therapeutic monoclonal antibodies. Clin. Pharamcokinet., 49:633-659 (2010).
Dostalek, M. et al., Pharmacokinetics, pharmacodynamics and physiologically-based pharmacokinetic modelling of monoclonal antibodies, Clin. Pharmacokinet., 52:83-124 (2013).
Duan, T. et al., Affinity-matured 'aquaporumab' anti-aquaporin-4 antibody for therapy of seropositive neuromyelitis optica spectrum disorders, Neuropharmacology, 162:107827 (2019).
Dunleavy, K., Regeneron, GlaxoSmithKline and Eli Lilly COVID-19 drugs prioritized for expedited review, 3 pages, (Jun. 30, 2021), retrieved online at: https://www.fiercepharma.com/pharma/covid-19-treatments-from-regeneron-lilly-gsk-vir-among-5-prioritized-for-expedited-review.
Eli Lilly, Emergency Use Authorization (EUA) for the Treatment or Post-Exposure Prophylaxis of COVID-19, 2 pages, (2021), retrieved online at: https://www.covid19.lilly.com/bamlanivimab/hcp/dosing-administration.
Eviq, Infusion related reaction, NSW Government, 1 page, (2017), retrieved online at: https://www.eviq.org.au/dose-mod-gradings/standard-ctcae/infusion-related-reaction-irr.
Gaudinski M.R. et al., Safety, tolerability, pharmacokinetics, and immunogenicity of the therapeutic monoclonal antibody mAb114 targeting Ebola virus glycoprotein (VRC 608): an open-label phase 1 study, Lancet, 393(10174):889-898 (2019).
Gedeon, P.C. et al., GLP toxicology study of a fully-human T cell redirecting CD3:EGFRvIII binding immunotherapeutic bispecific antibody. PLoS ONE, 15:e0236374 (2020).
Genentech, Inc., A Study of Rituximab Alternative Dosing Rate in Patients With Previously Untreated Diffuse Large B-cell or Follicular Non-Hodgkin's Lymphoma (RATE) (RATE), 8 pages, (2017), U.S. National Library of Medicine, retrieved online at: https://clinicaltrials.gov/ct2/show/study/NCT00719472.
Genentech, Inc., Fact Sheet for Healthcare Providers: Emergency Use Authorization for Actemra® (tocilizumab), 18 pages, (2021), retrieved online at: https://www.fda.gov/media/150321/download.
Genentech, Inc., Rituxan Dosing and Administration, 7 pages, (2022), retrieved online at: https://www.rituxan-hcp.com/nhl-cll/dosing-and-administration/rituxan-administration/rituxan-infusion.html.

(56) References Cited

OTHER PUBLICATIONS

Genentech, Inc., Rituxan, 5 pages, (2022), retrieved online at: rituxan-hcp.com.

Genzyme Polyclonals S.A.S., Thymoglobulin Highlights of Prescribing Information, 6 pages, (2020), retrieved online at: https://products.sanofi.us/thymoglobulin/thymoglobulin.pdf.

Gklinos, P. et al., Monoclonal Antibodies as Neurological Therapeutics, Pharmaceuticals, 14(2):92 (2021).

Glaxosmithkline, LLC, Fact Sheet for Healthcare Providers Emergency Use Authorization (Eua) of Sotrovimab, 32 pages, (2022), retrieved online at: https://www.fda.gov/media/149534/download.

Glaxosmithkline, Primary endpoint met in COMET-TAIL Phase III trial evaluating intramuscular administration of sotrovimab for early treatment of COVID-19, 16 pages, (2021), retrieved online at: https://www.gsk.com/en-gb/media/press-releases/primary-endpoint-met-in-comet-tail-phase-iii-trial-evaluating-intramuscular-administration-of-sotrovimab-for-early-treatment-of-covid-19/.

Gupta, A. et al., Early Treatment for Covid-19 with SARS-CoV-2 Neutralizing Antibody Sotrovimab, N. Engl. J. Med., 385(21):1941-1950 (2021).

Harn, N. et al., Highly concentrated monoclonal antibody solutions: direct analysis of physical structure and thermal stability, J. Pharm. Sci., 96(3):532-546 (2007).

Hauptmann, A. et al., Impact of buffer, protein concentration and sucrose addition on the aggregation and particle formation during freezing and thawing, Pharm. Res., 35(5):101 (2018).

Hawe, A. et al., Structural properties of monoclonal antibody aggregates induced by freeze-thawing and thermal stress, Eur. J. Pharm. Sci., 38(2):79-87 (2009).

Herzlinger, B. and Richman, B., Preparing Hospitals for the Next Pandemic. Harvard Business Review, 6 pages, (2021), retrieved online at: https://hbr.org/2021/06/preparing-hospitals-for-the-next-pandemic.

Horn, J. et al., Impact of fast and conservative freeze-drying on product quality of protein-mannitol-sucrose-glycerol lyophilizates, Eur. J. Pharm. Biopharm., 127:342-354 (2018).

Hospimedica International, European Commission Identifies 10 Most Promising Treatments for COVID-19, 2 pages, (Oct. 26, 2021), retrieved online at: https://www.hospimedica.com/covid-19/articles/294790274/european-commission-identifies-10-most-promising-treatments-for-covid-19.html.

Hruz, P.W., HIV protease inhibitors and insulin resistance: lessons from in-vitro, rodent and healthy human volunteer models. Curr. Opin. HIV AIDS, 3(6):660-665 (2008).

Kamath, E.D. et al., Translational pharmacokinetics and pharmacodynamics of monoclonal antibodies, Drug Discov. Today Technol., 21-22:75-83 (2016).

Katella, K., 9 Things You Need to Know About the New COVID-19 Pill, Yale Medicine, 5 pages, (2021), retrieved online at: https://www.yalemedicine.org/news/9-things-to-know-about-covid-pill.

Keizer, R.J. et al., Clinical pharmacokinetics of therapeutic monoclonal antibodies, Clin. Pharmacokinet., 49:493-507 (2010).

Kimball, S., FDA advisory panel narrowly endorses Merck's oral Covid treatment pill, despite reduced efficacy and safety questions, CNBC Health and Science, 7 pages, (2021), retrieved online at: Covid news: FDA panel narrowly endorses Merck pill, despite reduced efficacy (cnbc.com).

Kotler, D.P., HIV and antiretroviral therapy: lipid abnormalities and associated cardiovascular risk in HIV-infected patients. J. Acquir. Immune Defic. Syndr., 49(Suppl. 2):S79-S85 (2008).

Kueltzo, L.A. et al., Effects of solution conditions, processing parameters, and container materials on aggregation of a monoclonal antibody during freeze-thawing, J. Pharm. Sci., 97(5):1801-1812 (2008).

Le Basle, Y. et al., Physiochemical stability of monoclonal antibodies: a review, J. Pharm. Sci. 109:169-190 (2020).

Li, S. et al., Aggregation and precipitation of human relaxin induced by metal-catalyzed oxidation, Biochemistry, 34(17):5762-5772 (1995).

Lobo, E.D. et al., Antibody pharmacokinetics and pharmacodynamics, J. Pharm. Sci., 93:2645-2668 (2004).

Mahler, H.C. et al., Protein aggregation: pathways, induction factors and analysis, J Pharm Sci., 98(9):2909-2934 (2009).

Masato, A. et al., Suppression of Methionine Oxidation of a Pharmaceutical Antibody Stored in a Polymer-Based Syringe, J. Pharm. Sci., 105(2):623-629 (2016).

Mehta, S.B. et al., Gelation of a monoclonal antibody at the silicone oilewater interface and subsequent rupture of the interfacial gel results in aggregation and particle formation, J. Pharm. Sci., 104(4):1282-1290 (2015).

Merck and Co., Inc., Merck and Ridgeback's Investigational Oral Antiviral Molnupiravir Reduced the Risk of Hospitalization or Death by Approximately 50 Percent Compared to Placebo for Patients with Mild or Moderate COVID-19 in Positive Interim Analysis of Phase 3 Study, 8 pages, (2021), retrieved online at: https://www.merck.com/news/merck-and-ridgebacks-investigational-oral-antiviral-molnupiravir-reduced-the-risk-of-hospitalization-or-death-by-approximately-50-percent-compared-to-placebo-for-patients-with-mild-or-moderat/.

Minnema, L.A. et al., Exploring the Association between Monoclonal Antibodies and Depression and Suicidal Ideation and Behavior: A VigiBase Study, Drug Saf., 42(7):887-895 (2019).

Munson, E.S., Air from IV bags may pose danger; venous embolism comes from many causes, APSF Newsletter, 8(2), 6 pages, (1993), retreived online at: https://www.apsf.org/article/air-from-iv-bags-may-pose-danger-venous-embolism-comes-from-many-causes/.

National Home Infusion Association, Home Infusion of Covid-19 Monoclonal Antibodies, 4 pages, (2021), retrieved online at: https://nhia.org/NEWS/BAM-PILOT-PROGRAM/.

National Infusion Center Association website, 9 pages, retrieved online at: https://infusioncenter.org.

NBC Channel 5 Chicago, What to Know About COVID-19 Pills and What They Mean for the Pandemic Fight, 6 pages, (2021), retrieved online at: https://www.nbcchicago.com/news/coronavirus/what-to-know-about-covid-19-pills-and-what-they-mean-for-the-pandemic-fight/2686151/.

Nicoud, L. et al., Kinetics of monoclonal antibody aggregation from dilute toward concentrated conditions, J. Phys. Chem. B. 120(13):3267-3280 (2016).

NIH COVID-19 Treatment Guidelines, Anti-SARS-CoV-2 Monoclonal Antibodies, 8 pages, (2022), retrieved online at: https://www.covid19treatmentguidelines.nih.gov/therapies/anti-sars-cov-2-antibody-products/anti-sars-cov-2-monoclonal-antibodies/.

Ogawa, C. et al., Analysis of inline-filter blockage with trastuzumab formulation using scanning-electron microscopy, Biomed. Pharmacother., 112:108711 (2019).

Osterberg, L. and Blaschke, T., Adherence to medication, N. Engl. J. Med., 353:487-497 (2005).

Pfizer Inc., Pfizer's Novel COVID-19 Oral Antiviral Treatment Candidate Reduced Risk of Hospitalization or Death by 89% in Interim Analysis of Phase 2/3 EPIC-HR Study, 8 pages, (2021), retrieved online at: https://www.pfizer.com/news/press-release/press-release-detail/pfizers-novel-covid-19-oral-antiviral-treatment-candidate.

Pfizer Injectables, ATGAM Full Prescribing Information, 15 pages, (2021), retrieved online at: http://labeling.pfizer.com/ShowLabeling.aspx?id=525.

Regeneron Pharmaceuticals, Inc., COV-2067 Phase 3 Trial in High-Risk Outpatients Shows That Regen-Covtm (2400 Mg and 1200 Mg Iv Doses) Significantly Reduces Risk of Hospitalization or Death While Also Shortening Symptom Duration, 40 pages, (2021), retrieved online at: https://newsroom.regeneron.com/index.php/static-files/a7173b5a-28f3-45d4-bede-b97370bd03f8.

Regeneron Pharmaceuticals, Inc., Fact Sheet for Health Care Providers Emergency Use Authorization (EUA) of Regen-Cov® (casirivimab and imdevimab), 54 pages, (2022), retrieved online at: https://www.regeneron.com/downloads/treatment-covid19-eua-fact-sheet-for-hcp.pdf.

Regeneron Pharmaceuticals, Inc., Phase 3 Trial Shows Regen-Cov™ (Casirivimab With Imdevimab) Antibody Cocktail Reduced Hospitalization or Death by 70% in Non-Hospitalized Covid-19 Patients, 7 pages, (2021), retrieved online at: https://investor.regeneron.com/news-releases/news-release-details/phase-3-trial-shows-regen-covtm-casirivimab-imdevimab-antibody.

(56) References Cited

OTHER PUBLICATIONS

Rombouts, M.D. et al., Systematic Review on Infusion Reactions to and Infusion Rate of Monoclonal Antibodies Used in Cancer Treatment, Anticancer Research, 40(3):1201-1218 (2020).
Rosenberg, A.S., Effects of protein aggregates: am immunologic perspective, AAPS J., 8(3):E501-E507 (2006).
Ryman, J.T. and Meibohm, B., Pharmacokinetics and Monoclonal Antibodies, CPT Pharmacometrics Syst. Pharmacol., 6(9):576-588 (2017).
Salinas, B. et al., Understanding and modulating opalescence and viscosity in a monoclonal antibody formulation, J Pharm. Sci., 99(1):82-93 (2010).
Schermeyer, M.T. et al., Characterization of highly concentrated antibody solution—a toolbox for the description of protein long-term solution stability, MAbs, 9(7):1169-1185 (2017).
Schofield, D.J. et al., Preclinical development of a high affinity a-synuclein antibody, MEDI1341, that can enter the brain, sequester extracellular a-synuclein and attenuate a-synuclein spreading in vivo, Neurobiol. Dis., 132:104582 (2019).
Shire, S.J., Stability of monoclonal antibodies (mAbs), Monoclonal Antibodies, Woodhead Publishing, pp. 45-92, (2015).
Soontornniyomkij, V. et al., HIV protease inhibitor exposure predicts cerebral small vessel disease. AIDS. 28(9):1297-1306 (2014).
Sreedhara, A. et al., Stability of IgG1 monoclonal antibodies in intravenous infusion bags under clinical in-use conditions, J. Pharm. Sci., 101(1):21-30 (2012).
STAT Staff, Eight lingering questions about the new Covid pills from Merck and Pfizer, STAT Health, 10 pages, (2021), retrieved online at: https://www.statnews.com/2021/11/15/8-lingering-questions-about-the-new-covid-pills-from-merck-and-pfizer/.
The White House, National COVID-19 Preparedness Plan, 11 pages, (2022), retrieved online at: https://www.whitehouse.gov/covidplan/.
U.S. Department of Health and Human Services and U.S. Department of Defense, OWS Therapeutics Pre-EUA Playbook—Monoclonal Antibodies, Operation Warp Speed, 22 pages, (2020), retrieved online at: https://www.aha.org/system/files/media/file/2020/11/operation-warp-speed-playbook-allocation-distribution-covid-19-therapeutic-medications.pdf.
U.S. Department of Health and Human Services, Monoclonal Antibody Infusion Center Model (15 Stations), 4 pages, (2021), retrieved online at: https://www.phe.gov/emergency/events/COVID19/therapeutics/Pages/Infusion-Center-Model.aspx.
U.S. Food and Drug Administration, Emergency Use Authorization for Vaccines Explained, 3 pages, (2020), retrieved online at: https://www.fda.gov/vaccines-blood-biologics/vaccines/emergency-use-authorization-vaccines-explained.
U.S. Food and Drug Administration, Fact Sheet for Health Care Providers Emergency Use Authorization (EUA) of Bamlanivimab and Etesevimab, 45 pages, (2022), retrieved online at: https://www.fda.gov/media/145802/download.
U.S. Food and Drug Administration, Points to Consider in the Manufacture and Testing of Monoclonal Antibody Products for Human Use, 2 pages, (1997), retrieved online at: https://www.fda.gov/regulatory-information/search-fda-guidance-documents/points-consider-manufacture-and-testing-monoclonal-antibody-products-human-use.
Uchiyama, S., Liquid formulation for antibody drugs. Biochim. Biophys. Acta. 1844(11):2041-2052 (2014).
Wan, H., What ADME tests should be conducted for preclinical studies? ADMET and DMPK, 1(3):19-28 (2013).
Wang, M. et al., Interactions between biological products and product packaging and potential approaches to overcome them, AAPS PharmSciTech., 19(8):3681-3686 (2018).
Wang, W. et al., Monoclonal antibody pharmacokinetics and pharmacodynamics, Clin. Pharmacol. Ther., 84:548-558 (2008).
Wang, W., Protein aggregation and its inhibition in biopharmaceutics, Int. J. Pharm., 289(1-2):1-30 (2005).
Yang, R. et al., Rapid assessment of oxidation via middledown LCMS correlates with methionine side-chain solvent-accessible surface area for 121 clinical stage monoclonal antibodies, MAbs, 9(4):646-653 (2017).
Zhao L. et al., The antibody drug absorption following subcutaneous or intramuscular administration and its mathematical description by coupling physiologically based absorption process with the conventional compartment pharmacokinetic model, J. Clin. Pharmacol., 53:314-325 (2013).
International Search Report for PCT/US21/64724, filed Dec. 21, 2021, 4 pages, (dated May 18, 2022).
Mita, A. C. et al., Phase I and pharmacokinetic study of AI-850, a novel microparticle hydrophobic drug delivery system for paclitaxel, Clin. Cancer Res., 13(11):3293-3301, (2007).
Rivera, G. et al., Rapid implementation of pharmacy infusion services for emergency use authorization COVID-19 treatments at a field hospital, Am. J. Health Syst. Pharm., 78(22):2015-2019, (2021).
Swan, J. T. et al., Use of a pharmacy protocol to convert standard rituximab infusions to rapid infusion shortens outpatient infusion clinic visits, Pharmacotherapy, 34(7):686-694, (2014).
Written Opinion for PCT/US21/64724, filed Dec. 21, 2021, 9 pages, (dated May 18, 2022).
Atmar, J., Review of the Safety and Feasibility of Rapid Infusion of Rituximab, Journal of Oncology Practice, 6(2):91-93 (2010).
Creative Biolabs Therapeutics, C-Terminal Lysine Variant Analysis, 5 pages, (2022), retrieved online at: https://www.creative-biolabs.com/drug-discovery/therapeutics/c-terminal-lysine-variant-analysis.htm.
Creative Biolabs Therapeutics, Dynamic Light Scattering (DLS), 5 pages, (2022), retrieved online at: https://www.creative-biolabs.com/drug-discovery/therapeutics/dynamic-light-scattering-dls.htm.
Creative Biolabs Therapeutics, N-Terminal Cyclization Analysis, 5 pages, (2022), retrieved online at: https://www.creative-biolabs.com/drug-discovery/therapeutics/n-terminal-cyclization-analysis.htm.
Creative Biolabs Therapeutics, Oxidation Analysis, 5 pages, (2022), retrieved online at: https://www.creative biolabs.com/drug-discovery/therapeutics/oxidation-analysis.htm.
Creative Biolabs Therapeutics, Sedimentation Velocity Analytical Ultracentrifugation (SV-AUC) for Antibody Aggregation Analysis, 5 pages, (2022), retrieved online at: https://www.creative-biolabs.com/drug discovery/therapeutics/sedimentation-velocity-analytical-ultracentrifugation-sv-auc-for-antibody-aggregation-analysis.htm.
Creative Biolabs Therapeutics, Size Exclusion Chromatography (SEC) for Antibody Aggregation Analysis, 5 pages, (2022), retrieved online at: https://www.creative-biolabs.com/drug-discovery/therapeutics/size-exclusion-chromatography-sec-for-antibody-aggregation-analysis.htm.
European Commission, Questions and Answers: COVID-19 Therapeutics Strategy—list of 5 candidate therapeutics, 4 pages, (2021), retrieved online at: https://ec.europa.eu/commission/presscorner/detail/en/qanda_21_3301.
Franklin, B.D., 'Smart' intravenous pumps: how smart are they?, BMJ Qual. Saf., 26:93-94 (2017).

* cited by examiner

METHODS, SYSTEMS, AND APPARATUS FOR ADMINISTERING A MONOCLONAL AND/OR POLYCLONAL ANTIBODY TREATMENT VIA RAPID INFUSION

RELATED APPLICATIONS

This application is a continuation of U.S. application Ser. No. 17/558,295 filed on Dec. 21, 2021, which claims the benefit of U.S. Provisional Application No. 63/129,401 filed on Dec. 22, 2020, U.S. Provisional Application No. 63/220,854 filed on Jul. 12, 2021, U.S. Provisional Application No. 63/223,921 filed on Jul. 20, 2021, U.S. Provisional Application No. 63/227,803 filed on Jul. 30, 2021, U.S. Provisional Application No. 63/249,299 filed on Sep. 28, 2021, U.S. Provisional Application No. 63/253,790 filed on Oct. 8, 2021, U.S. Provisional Application No. 63/280,953 filed on Nov. 18, 2021, and U.S. Provisional Application No. 63/286,353 filed on Dec. 6, 2021, the entire contents of each which are hereby incorporated by reference.

FIELD

The subject matter described herein relates to methods, systems, and apparatus for rapid infusion of a monoclonal and/or polyclonal antibody, particularly for use in disease therapy.

SUMMARY OF THE INVENTION

Currently, a number of monoclonal antibody treatments are being tested for treatment of COVID-19, the illness caused by the virus SARS-CoV-2. For example, the following are among the therapeutic agents currently under investigation for treatment of COVID-19: LY-CoV555 (bamlanivimab) (Eli Lilly); LY-CoV555 (bamlanivimab)+JS016 (etesevimab) antibody cocktail (Eli Lilly); REGN-COV2 aka REGEN-COV™ aka REGN10933+REGN10987, aka Ronapreve, aka casirivimab and imdevimab antibody cocktail, (Regeneron, Roche); gimsilumab (Roivant Sciences); Actemra aka tocilizumab (Genentech); B38, H4, B5 and/or H2 Capital Medical University, Beijing; COVI-GUARD™ (STI-1499) and COVI-AMG™ (STI-2020) (Sorrento Therapeutics); regdanvimab (Celltrion); VIR-7831 (sotrovimab) and VIR-7832 (Vir Biotechnology).

Moreover, in June 2021, the European Commission identified five COVID-19 therapeutics it would prioritize with the hope to authorize three by October 2021 (https://ec.europa.eu/commission/presscorner/detail/en/qanda_21_3301). The list of five therapeutic candidates include four monoclonal antibody regimens—Eli Lilly's bamlanivimab/etesevimab combination, Celltrion's regdanvimab (Regkirona), Regeneron and Roche's casirivimab/imdevimab cocktail, and GlaxoSmithKline and Vir Biotechnology's sotrovimab.[1]

In October 2021, the European Commission identified a portfolio of ten promising treatments for COVID-19.[2] Within the category of monoclonal antibodies, the Commission identified Ronapreve (a combination of two monoclonal antibodies casirivimab and imdevimab), manufactured by Regeneron Pharmaceuticals and Roche; Xevudy (sotrovimab), manufactured by Vir Biotechnology and GlaxoSmithKline; and Evusheld (a combination of two monoclonal antibodies tixagevimab and cilgavimab), manufactured by AstraZeneca. On Nov. 12, 2021, the European Commission granted marketing authorizations for the aforementioned Ronapreve (casirivimab/imdevimab) and Regkirona (regdanvimab).

IV-administered mAbs are among the most widely used pharmaceuticals in the world.[3] These include Keytruda (pembrolizumab), manufactured by Merck, for various cancers; Opdivo (nivolumab), manufactured by Bristol Myers Squibb, for various forms of cancer; Avastin (bevacizumab), manufactured by Roche, for colorectal, lung, glioblastoma, kidney, cervical, and ovarian cancer; Ocrevus (ocrelizumab), manufactured by Roche, for relapsing or primary progressive multiple sclerosis; Rituxan (rituximab), manufactured by Roche, Pharmstandard, for various autoimmune diseases and cancers; Darzalex (daratumumab), manfucatured by Janssen (Johnson & Johnson), for multiple myeloma; Perjeta (pertuzumab), manufactured by Roche, for HER2-positive breast cancer; Herceptin (trastuzumab), manufactured by Genentech (Roche), for breast, stomach, and esophageal cancer; Remicade (infliximab), manufactured by Janssen (Johnson & Johnson), for Crohn's disease, ulcerative colitis, rheumatoid arthritis, ankylosing spondylitis, psoriatic arthritis, and plaque psoriasis; Actemra/RoActemra (tocilizumab), manufactured by Roche, for rheumatoid arthritis, forms of juvenile idiopathic arthritis and giant cell arteritis as well as CAR T cell-induced severe or life-threatening cytokine release syndrome; and Tecentriq (atezolizumab), manufactured by Roche, for urothelial carcinoma, non-small cell lung cancer, and triple-negative breast cancer. Other IV-administered mAbs include Bexxar (tositumomab-1131), manufactured by GSK, for non-Hodgkin lymphoma; Lartruvo (olaratumab), manufactured by Eli Lilly, for soft tissue sarcoma; MabThera, Rituxan (rituximab), manufactured by Biogen/Genentech, for non-Hodgkin lymphoma; Simulect (basiliximab), manufactured by Novartis, for prevention of kidney transplant rejection; Zevalin (ibritumomab tiuxetan), manufactured by Spectrum, for non-Hodgkin lymphoma; Erbitux (cetuximab), manufactured by Bristol Meyers Squibb, Eli Lilly, and Merck, for colorectal cancer; Tysabri (natalizumab), manufactured by Biogen/Elan, for multiple sclerosis; Vectibix (panitumumab), manufactured by Amgen, for colorectal cancer; Lucentix (ranibizumab), manufactured by Genentech/Novartis, for macular degeneration; Soliris (eculizumab), manufactured by Alexion, for paroxysmal nocturnal hemoglobinuria; Arzerra (ofatumumab), manufactured by Novartis, for chronic lymphocytic leukemia; Benlysta (belimumab), manufactured by Human Genome Sciences, for systemic lupus erythematosus; Yervoy (ipilimumab), manufactured by Bristol Meyers Squibb, for metastatic melanoma; Perjeta (pertuzumab), manufactured by Genentech, for breast cancer; raxibacumab, manufactured by Human Genome Sciences, for anthrax infection; Gazyva, Gazyvaro (obinutuzumab), manufactured by Genentech, for chronic lymphocytic leukemia; Sylvant (siltuximab), manufactured by Janssen Biotech), for Castelman disease; Cyramza, (ramucirumab), manufactured by Eli Lilly, for gastric cancer; Entyvio (vedolizumab), manufactured by Takeda, for ulcerative colitis, Crohn's disease; Lemtrada, MabCampath, Campath-1H (alemtuzumab), manufactured by Genzyme, for multiple sclerosis and chronic myeloid leukemia, Portrazza (necitumumab), manufactured by Eli Lilly, for non-small cell lung cancer; Qarziba, Unituxin (dinutuximab), manufactured by United Therapeutics, for neuroblastoma; Empliciti (elotuzumab), manufactured by Bristol Meyers Squibb, for multiple myeloma; Cinqaero, Cinqair (reslizumab), manufactured by Teva, for asthma; Zinplava (bezlotoxumab), manufactured by Merck Sharp Dohme, for prevention of *Clostridium difficile* infection recurrence; Anthim (obiltoxaximab), for prevention of inhalational anthrax, Bavencio (avelumab), manufactured by Merck, for Merkel cell carcinoma; and Imfinzi (durvalumab), manufactured by AstraZeneca, for bladder cancer.

Also, a number of monoclonal antibody treatments are approved, and a number are being evaluated, for treatment of various neurological diseases and conditions[4]. These include the following:

Alzheimer's disease (AD): aducanumab (Biogen Inc.), gantenerumab (Chugai Pharmaceutical Co., Ltd., Hoffmann-La Roche), donanemab (Eli Lilly and Company), BAN2401[5] (Eisai Co., Ltd. and Biogen Inc.), gosuranemab (Biogen Inc., Bristol-Myers Squibb), zagotenemab (Eli Lilly and Company), tilavonemab (AbbVie, C2N Diagnostics, LLC), semorinemab (AC Immune SA, Genentech, Hoffmann-La Roche);

Parkinson's disease (PD): cinpanemab (Biogen, Neurimmune), MEDI1341[6] (AstraZeneca, Takeda Pharmaceutical Company);

Duchene's muscular dystrophy (DMD): domagrozumab (Pfizer Inc.);

Multiple sclerosis (MS): natalizumab (humanized Ab directed against α4 β1 integrin) (Biogen Inc.), alemtuzumab (Sanofi), ocrelizumab (Genentech USA, Inc.), ofatumumab (Novartis Pharmaceuticals Corporation), inebilizumab (Horizon Therapeutics plc);

Migraine: erenumab (Amgen Inc.), fremanezumab (Teva Pharmaceuticals USA, Inc.), eptinezumab (Lundbeck), galcanezumab (Lilly USA, LLC);

Migraine and cluster headache: galcanezumab (Lilly USA, LLC);

Neuromyelitis optica spectrum disorder (NMOSD), aka Devic disease: rituximab (Amgen Inc.), eculizumab (Alexion Pharmaceuticals, Inc.), inebilizumab (Horizon Therapeutics plc), tocilizumab (Genentech, Inc.), satralizumab (Genentech USA, Inc.), ravulizumab (Alexion Pharmaceuticals, Inc.), aquaporumab[7];

Idiopathic inflammatory myopathies (IIM) (includes dermatomyositis (DM), polymyositis (PM), inclusion body myositis, immune-mediated necrotizing myopathy, and antisynthetase syndrome: rituximab (Amgen Inc.), infliximab (Amgen Inc.), tocilizumab (Genentech, Inc.), alemtuzumab (Sanofi);

Myasthenia gravis (MG): rituximab (Amgen Inc.), eculizumab (Alexion Pharmaceuticals, Inc.), ravulizumab (Alexion Pharmaceuticals, Inc.), rozanolixizumab[8], nipocalimab (Johnson & Johnson Inc.), batoclimab (Harbour BioMed), efgartigimod (Argenx);

Immune-related peripheral neuropathies (multifocal motor neuropathy (MMN), anti-myelin associate glycoprotein (anti-MAG) neuropathy, chronic inflammatory demyelinating polyneuropathy (CIDP)): rituximab (Amgen Inc.);

Neurooncological conditions (malignant glioma, recurrent glioblastoma): bevacizumab (Pfizer Inc.), rilotumumab (Amgen Inc.), CD3-binding bispecific antibody (hEGFRvIII-CD3-bi-scFv)[9] for immunotherapy of malignant glioma.

Moreover, a number of polyclonal antibody (pAb) treatments and other treatments have been or are being evaluated for treatment of organ and tissue transplant patients, which must be administered by infusion[10]. These include Thymoglobulin® (anti-thymocyte globulin [rabbit]) (Sanofi), which is FDA approved for prophylaxis of acute rejection. Currently, the first dose is required to be infused over at least 6 hours, with doses on subsequent days infused over at least 4 hours[11]. Another approved polyclonal antibody treatment is Atgam® (lymphocyte immune globulin, anti-thymocyte globulin [equine] sterile solution) (Pfizer), where currently, each dose must be infused over at least 4 hours[12]. Other drugs being investigated for chronic graft vs. host disease (GVHD) include an anti-CD6 antibody called alpha-1 antitrypsin, and a double antibody conjugate that is an anti-CD3 and anti-CD7 agent. Monoclonal antibodies used for treatment of transplant patients include alemtuzumab (Sanofi), rituximab (Amgen Inc), and others.

It is generally accepted that mAb and pAb treatments must be administered intravenously. For example, LY-CoV555 is administered to a patient by intravenous (IV) infusion over at least a one-hour period of time. Moreover, it is often impractical for a mAb or pAb treatment to be administered by injection (i.e., one or multiple "shots" or injections of a relatively small volume of drug directly into a vein with a needle) or by intravenous "push," IVP (i.e., rapid administration of a small volume of medication into the vein via a previously inserted intravenous catheter). Instead, mAbs and pAbs are infused in an out-patient setting, e.g., at a free-standing or hospital-based infusion center,[13] a skilled nursing facility (SNF), or via in-home infusion. Both infusion centers and in-home infusion require health care personnel to manage nursing assistance and supplies to support infusion therapy delivered in an Ambulatory Infusion Suite or in the home. Ambulatory and home infusion resources are limited in capacity and human resources. Reducing the time necessary to complete each infusion would significantly reduce the person-hours of personnel resources needed and free up capacity and other resources. Likely to aid increased supply, the U.S. Department of Health & Human Services has issued designs for monoclonal antibody infusion centers, dedicated for the administration of monoclonal antibodies in the treatment of COVID-19.[14]

Administration of certain mAbs by subcutaneous injection for the treatment of COVID-19 is currently allowed under Emergency Use Authorization. Under an EUA, the FDA may allow the use of unapproved medical products or unapproved uses of approved medical products in an emergency to diagnose, treat, or prevent serious or life-threatening diseases or conditions when certain statutory criteria have been met, including that there are no adequate, approved, and available alternatives.[15] However, data suggest mAbs administered by subcutaneous injection may have decreased bioavailability compared to infusion.[16] Moreover, the Emergency Use Authorization (EUA) fact sheet for REGEN-COV™ (casirivimab and imdevimab)[17] states, in all-caps, "FOR TREATMENT, INTRAVENOUS INFUSION IS STRONGLY RECOMMENDED. SUBCUTANEOUS INJECTION IS AN ALTERNATIVE ROUTE OF ADMINISTRATION WHEN INTRAVENOUS INFUSION IS NOT FEASIBLE AND WOULD LEAD TO DELAY IN TREATMENT." The FDA updated the EUA for casirivimab plus imdevimab on Jun. 3, 2021, to authorize administration by subcutaneous injection in situations where an IV infusion is not feasible or would delay treatment. Here, administration by subcutaneous injection requires four injections at four different sites on the body. The NIH notes on its website that safety and efficacy data for casirivimab plus imdevimab administered by subcutaneous injection are limited, and that subcutaneous injection should only be used when IV infusion is not feasible or would lead to a delay in treatment.[18]

Administration of a monoclonal antibody by intramuscular (IM) administration is currently under investigation by GlaxoSmithKline plc and Vir Biotechnology, Inc., for their COVID-19 mAb, sotrovimab. Intramuscular injections are generally more painful than subcutaneous injections. A company press release dated Nov. 12, 2021, stated, "COMET-TAIL Phase III data demonstrated that intramuscular administration of sotrovimab was non-inferior and offered similar efficacy to intravenous administration for high-risk populations".[19] However, it should be noted, there was a higher rate of progression to hospitalization or death for recipients of the IM injection versus those who received IV infusion. The press release states, "In the IM administration (500 mg) arm of the trial, there was a 2.7% rate of progression to hospitalisation for more than 24 hours or death through Day 29 of the trial, compared to 1.3% in the IV administration arm (also 500 mg). The adjusted difference between the IM and IV arms of the trial was 1.07% with a 95% confidence interval (CI) of −1.25% to 3.39%. The upper bound of the 95% CI is within the predetermined 3.5% non-inferiority margin set for the trial's primary endpoint in consultation with the US Food and Drug Administration (FDA)." According to the press release, the companies plan to submit the full COMET-TAIL data set to a peer-reviewed journal for publication in the first quarter of 2022.

mAb solutions that are of sufficiently high concentration to reasonably limit the number of injections required per patient per treatment may have unsuitably high viscosity. Such solutions require increased force and time required for subcutaneous injection or intramuscular injection. Viscous formulations can result in increased pain upon injection, or may even preclude this route of delivery. High mAb concentration may also increase opalescence, which introduces a potential safety issue, for example, because an opalescent solution is easily confused with turbid solutions that can result from protein aggregation or other particulate formation. Thus, even if rapid administration through subcutaneous injection is technically feasible, infusion is likely to be more effective.[20]

Moreover, injections may be significantly more costly than infusion since they may require multiple injection sites per treatment. For example, the estimated cost per treatment by infusion using 1 vial of Regeneron's antibody cocktail (casirivimab+imdevimab) is from $1893 to $2,086, whereas cost per treatment by injection is from $6,320 to $6,532, assuming 4 vials are required to complete the full treatment regimen (four injections, each given at a different location, i.e., right arm, right leg, left leg, and left arm) (based on data compiled by PRA Health Sciences, as of Jun. 19, 2021). Thus, even if rapid administration through subcutaneous injection is feasible, infusion may be more effective and less expensive.

It was announced Oct. 1, 2021, that an investigational oral antiviral (pill), molnupiravir (Merck and Ridgeback Biotherapeutics), reduced the risk of hospitalization or death of unvaccinated mild to moderate COVID-19 patients by approximately 50% compared to placebo for patients with mild or moderate COVID-19 in a positive interim analysis of Phase 3 trial.[21] However, a more complete set of data presented to the FDA on Nov. 30, 2021, indicated the drug is only 30% effective, not 50% as reported earlier.[22] While the FDA's Antimicrobial Drugs Advisory Committee voted 13 to 10 to recommend emergency authorization of molnupiravir, it was reported to be a difficult vote due to unanswered questions about drug safety, including the potential for birth defects if taken during pregnancy (discussed in more detail below), as well as questions about potential rare-event escape mutant concerns and evolution of the virus.[23]

On Nov. 5, 2021, Pfizer announced that its oral medication for treatment of COVID-19, Paxlovid (PF-07321332; ritonavir), reduced hospitalization or death by 89% versus placebo according to its interim analysis of its Phase 2/3 study.[24] However, data beyond the press release are not yet available, with information about potential side effects unknown.[25] Moreover, the 89% figure applied to patients who started taking the pill within three days of their first COVID-19 symptoms, whereas Merck's original 50% figure applied to patients who began treatment within five days.[26] It may be difficult for a patient to be tested soon enough following first symptoms to be diagnosed with COVID-19 and begin the pill regimen immediately, while the medication is most effective. Paxlovid is given as a five-day course and must be taken with a second medicine, ritonavir (AbbVie), so that the Pfizer regimen involves taking 30 pills over a five-day period;[27] thus, there is the potential for patient compliance issues, as is discussed in more detail below.

While a COVID-19 therapeutic in pill form may offer convenience benefits, it appears infusion-delivered mAbs may be more effective at reducing hospitalization or death, at least versus the Merck pill, and infusion-delivered mAbs may be less problematic in terms of potential negative side effects. For example, Regeneron's mAb therapeutic REGEN-COV™ (casirivimab with imdevimab) reduced hospitalization or death by 70% in non-hospitalized COVID-19 patients in a Phase 3 trial, as compared to the 30% figure for the Merck pill above.[28] Furthermore, infusion-delivered mAbs are better established in terms of understood, minimal side effects. The Merck COVID-19 pill (molnupiravir) and the Pfizer COVID-19 pill (PF-07321332; ritonavir), are protease inhibitors,[29] and there is some concern about the potential mutagenicity of protease inhibitors. For example, these drugs may interfere with RNA replication needed for fetal development and cause birth defects.[30]

While pill-form medications are convenient, it is known that non-compliance is a significant problem—for example, in the United States, approximately one in five new prescriptions for pill-form medication are never filled, and of those filled, about half are taken incorrectly with regard to timing, dosage, frequency, and/or duration.[31] Moreover, protease inhibitors, which have long been used, like those for HIV treatment, are known to induce non-compliance, in part, because of side effects such as metabolic syndromes (e.g., dyslipidemia, insulin-resistance, lipodystrophy/lipoatrophy), jaundice, diarrhea, as well as cardiovascular and cerebrovascular diseases.[32] As indicated above, non-compliance is a risk especially noted for these COVID drugs, which have a complex dosage regimen—both drugs are given for five days. Pfizer's regimen is three pills in the morning and three pills at night. Merck's drug is taken as four pills in the morning and four at night. Said Dr. Robert Murphy, an infectious disease specialist and executive director of the Institute for Global Health at Northwestern University Feinberg School of Medicine, about the Pfizer pill, "It's a cumbersome regimen,". "You have to take 30 pills over five days. That's a lot of pills. That includes two ritonavirs and four Paxlovids per day. It's not like you pop one pill."[33] Patient non-compliance is avoided by infusion-administered medication. Additionally, mAbs administered by infusion enable on-site inspection/evaluation for infusion related reactions (IRRs).

A pilot test of home infusion of COVID-19 monoclonal antibodies to increase convenience demonstrated satisfactory results and participation by home infusion firms.[34] Moreover, new companies are emerging to enhance convenience by facilitating administration of mAbs infusions in the home. For example, CourMed, a health concierge startup in the Dallas area, is working to assure COVID-19 patients who may be immunocompromised can obtain mAbs infusion on-demand for about $1000 (USD) with the help of a partnering pharmacy and qualified nurse who administers the infusion at the patient's home.

It has been thought that monoclonal and polyclonal antibodies may have restrictions on their rate of infusion, for example, to allow sufficient time to identify an allergic or otherwise adverse reaction that the patient is experiencing during IV administration of the drug so that administration can be halted before a potentially dangerous quantity of the drug is received by the patient. The rate of infusion may need to be limited to reduce the severity of known side effects experienced during or immediately after infusion. However, it should be noted that traditional infusion has been linked to depression and suicidal ideation,[35] and, where possible, it may be beneficial to avoid a lengthier infusion due to a slow infusion rate, at least from a mental health standpoint. Infusion related reactions (IRRs) are classified in four categories—Grade 1: mild transient reaction, infusion interruption not indicated, intervention not indicated; Grade 2: therapy or infusion interruption indicated but patient responds promptly to symptomatic treatment (e.g., antihistamines, NSAIDS, narcotics, IV fluids), prophylactic medications indicated for up to 24 hours; Grade 3: prolonged (e.g., not rapidly responsive to symptomatic medication and/or brief interruption of infusion); recurrence of symptoms following initial improvement, hospitalization indicated for clinical sequelae; Grade 4: life-threatening consequences, urgent intervention indicated.[36] Infusion requires observation time following administration of the infusion to monitor and, if needed, provide medical intervention in the event of an adverse infusion reaction experienced by the patient. For example, the Emergency Use Authorization (EUA) for administering the authorized dosage of the Eli Lilly drug bamlanivimab and etesevimab instructs clinical monitoring of each patient for at least one hour after infusion is complete.[37] Monoclonal and polyclonal antibodies that are not fully humanized may require even more time after infusion to monitor the patient for adverse reactions.

Infusion rates vary by drug, though an infusion of a mAbs treatment solution is typically completed within a range of 20 to 90 minutes, not including after-administration patient observation time. The lower infusion times in this range generally correspond to administration of higher concentration mAbs solutions, with their concomitant higher viscosities, increased opalescence, and potentially greater administration difficulty, greater side effects and/or lower effectiveness, as discussed above with respect to subcutaneous injection of high concentration mAb solutions. Polyclonal antibody treatments generally require at least 4 hours per dose, currently. See, for example, Thymoglobulin (anti-thymocyte globulin, Sanofi), and Atgam (lymphocyte immune globulin, anti-thymocyte globulin [equine] sterile solution, Pfizer), both of which require at least 4 hours infusion time per dose.

It is recognized herein that it would be beneficial to increase infusion rate for treatment of acute conditions, including those caused by viral infections, such as COVID-19 and other acute conditions caused by a viral infection, e.g., coronavirus infection, as well as for treatment of various kinds of cancer (e.g., leukemia); neurological disorders such as Alzheimer's disease, Parkinson's disease, and migraine; autoimmune diseases such as rheumatoid arthritis, Crohn's disease, lupus, and ulcerative colitis; dermatitis; arthritis; psoriasis; asthma and other respiratory diseases; multiple sclerosis; macular degeneration; and for treatment of organ and tissue transplant patients, thereby reducing the time required to administer a full effective dose of the drug (e.g., monoclonal and/or polyclonal antibody/ies). For treatment of COVID-19, it was estimated that the Total Addressable Market (TAM) in the U.S. in July 2021 was about 12,514 daily patients for a seven-day average (https://www.cdc.gov/coronavirus/2019-ncov/covid-data/covid-view/index.html). Of these infections, approximately 80% were Mild/Moderate, and approximately 50% were either (i) above the age of 65 or (ii) above the age of 55 with an underlying health condition. Assuming the existing monoclonal antibody treatments are appropriate for mild/moderate cases for patients in either category (i) or (ii), the U.S. daily TAM is 12.5 k×80%×50%=5,000 patients. However, variant strains of SARS-CoV-2 have been identified, and some are believed to be more rapidly transmissible than other circulating strains of SARS-CoV-2. It is possible other variant strains will be identified over time, possibly one or more vaccine-resistant variants, and the need for treatment of the disease(s) caused by these viruses may increase despite availability of some vaccines.

Administering infusions to 5,000 patients per day in the U.S. presents a difficult challenge. Currently, infusions for various diseases such as cancer and diabetes are administered at infusion centers, most established for treatment of patients with chronic conditions who require regular infusions. Many of these patients are immunocompromised, and it would be risky to comingle such patients having chronic conditions with COVID-19 patients receiving an infusion for COVID-19 treatment (e.g., monoclonal antibody/ies), an acute condition. Existing infusion centers are likely not able to provide treatment for COVID-19 patients due to the need for segregation of space to protect their chronic immunocompromised patients. It is reported that there is lower uptake of monoclonal antibody treatments for COVID-19 than expected, perhaps due in part to their mode of administration.[38] There is a need for more infusion centers, particularly those dedicated for treatment of COVID-19 patients (and/or patients who suffer from an infectious disease). Because of a lack of such sites, Florida, North Carolina, Rhode Island, and Texas are among the states that have opened state-sponsored sites where infusion-delivered monoclonal antibody therapy is offered for treatment of COVID-19.

Moreover, on Dec. 2, 2021, the White House announced a COVID-19 surge response effort to launch "monoclonal antibody strike teams" to deploy clinical personnel through HHS, FEMA, and DOD to help hospitals and health systems provide this infusion-delivered therapy.[39] It was also announced the HHS will amend the Public Readiness and Emergency Preparedness (PREP) Act declaration to allow more providers, including pharmacists, to administered monoclonal antibody infusions for the treatment of COVID-19.[40]

The U.S. Centers for Medicare & Medicaid Services (CMS) increased the Medicare payment rate for administering monoclonal antibodies from $310 to $450 on May 6, 2021, and has stated a higher national payment rate of $750 will be established when monoclonal antibodies are administered in the beneficiary's home.[41] However, these sums are likely not economically sufficient for coverage of the costs for two hours of work at infusion sites or three to four hours of work for at-home administration.

In 2020, the National Home Infusion Association (NHIA) estimated that home and specialty infusion is a $19 billion industry made up of about 900 providers serving 3.2 million patients annually (https://www.nhia.org/about-infusiontherapy/). However, the July 2021-estimated TAM for treatment of COVID-19 by monoclonal antibody infusion was 5,000 daily, for a total of 1.8 million yearly, over half the 3.2 million total of 2020 infusion patients. While the aforementioned states have opened state-sponsored sites for administration of monoclonal antibody infusion for treatment of COVID-19 (e.g., Florida, North Carolina, Rhode Island, and Texas), such state-sponsored sites are not currently available nationwide.

It has been found that the use of monoclonal antibody treatment for COVID-19 results in a significant reduction in the risk of hospitalization or mortality for at-risk populations.[42] In addition to the reduction in hospitalization and mortality, a strong economic case can be made for increased use of monoclonal antibody treatment to avoid the much greater costs associated with hospitalization, and to alleviate shortages of beds in hospitals due to hospitalized COVID-19 patients.[43]

It is presented herein that increasing infusion rate is crucial to administering monoclonal and/or polyclonal antibody treatment of COVID-19 to as many of the patients in need thereof as possible. The benefit provided by these treatments is significant. For example, clinical trial of the Regeneron mAbs infusion (casirivimab+imdevimab) demonstrated a significant reduction in COVID-related hospitalization or death of 71.3% (1.3% vs. 4.6%; p<0.0001) in the 2,400 mg group and 70.4% (1.0% vs. 3.2%) in the 1,200 mg group, as compared to placebo.[44] Moreover, a study of 966 participants in a clinical trial of Eli Lilly's bamlanivimab demonstrated reduced symptomatic and severe COVID-19 infection by 80% when compared to placebo (8.8% vs. 22.5%; or 0.20 [0.08-0.49]; p<0.001). This effect held true for the subpopulation at high risk for severe disease.[45]

It would be beneficial to establish a safe prescribed administration rate to facilitate safe administration of a full effective dose of the drug within as short a time as possible. Restrictions on rate of drug infusion are generally determined during registration trials. For fully humanized antibodies such as bamlanivimab and etesevimab, it is likely that a higher prescribed administration rate can be established. As discussed in more detail below, safe rapid infusion of certain high dose monoclonal antibodies has been established.

An infusion rate study was conducted for more rapid administration of Rituximab in patients with previously untreated diffuse large B-cell or follicular non-Hodgkin's lymphoma.[46] The maximum infusion rate was 400 mg/hr, with total infusion time of 90 minutes (20% in the first 30 minutes, 80% in the last 60 minutes). A review of studies of more-rapid infusion protocols for rituximab reported that few adverse events were observed, the vast majority of which were grade 1 in nature (Review of the Safety and Feasibility of Rapid Infusion of Rituximab, *Journal of Oncology Practice*, Vol. 6, No. 2, Mar. 1, 2010, https://ascopubs.org/doi/10.1200/JOP.200001).

TABLE 1

Reported Safety Results From Rapid Infusion of Rituximab

| Study | No. of Patients | Infusion-Related Adverse Events |
| --- | --- | --- |
| 60-min Infusion | | |
| Byrd, 2001 | 33 (26 CLL, 7 SLL) | No accelerated infusion-related reactions |
| Aurran-Schleinitz, 2005[12] | 69 (56 NHL, 11 CLL) | Grade 1 event in 1 patient |
| Provencio, 2006 | 40 (39 NHL, 1 Hodgkin's) | Grade 1 events: chills (2); limited cutaneous reaction with rash (2); fever (1) |
| Siano, 2008 | 32 NHL | Grade 1-2 events: headache (4); asthenia (3); dyspnea (1); hypotension (1) |

Rituximab is a partially humanized monoclonal antibody, whereas bamlanivimab and etesevimab are full human immunoglobulin G-1 (IgG1 variant) monoclonal antibodies and are presently thought to be even less likely to result in infusion reactions.

Moreover, a recent review article studied the infusion rate of monoclonal antibodies used in cancer treatment and stated, "In order to improve patient satisfaction in combination with reducing hospital drug-delivery related healthcare costs, shortening infusion duration or shortening post-administration observation time is an attractive option . . . . From our review, we conclude that administration of the following monoclonal antibodies in an increased infusion rate as compared to the one stated by the manufacturer is safe: Bevacizumab, ipilimumab, nivolumab (low dose), panitumumab and rituximab."[47] Interestingly, one of the approaches to reducing the incidence of infusion-related reactions prescribed by the manufacturer of daratumumab is "diluting the first dose into 1,000 ml versus 500 ml for subsequent doses".[48] Unfortunately, increasing the administered volume requires a longer infusion duration using standard infusion methods.

Also, a dose-escalation study for a fully humanized monoclonal antibody, mAb114, was conducted by the US National Institutes of Health (NIH) to assess safety and tolerability for the treatment of Ebola. The study found mAb114 was well tolerated and was easily and relatively quickly infused (the drug was administered intravenously over 30 minutes).[49]

Thus, it is likely possible to establish safe higher infusion rates of bamlanivimab and etesevimab (and/or other monoclonal antibodies) for the treatment of COVID-19 (and other virus-caused diseases) than the rate prescribed in the Emergency Use Authorization (EUA) for administering the authorized dosage of the Eli Lilly drug bamlanivimab and etesevimab. Higher rates could also be established for other monoclonal antibodies and/or polyclonal antibodies that require long infusion times.

As explained above, most IV-administered drugs are infused over a 60 to 90 minute period of time. For a drug administered to a large number of individuals in response to a viral outbreak, such as the SARS-CoV-2 virus which causes COVID-19, this length of time may not only reduce patient satisfaction and adversely affect patient mental health, but it may also result in the serious problem of an inability to treat all patients who need the drug. In recognition of this issue, Operation Warp Speed mentions the one-hour infusion time for LY-CoV555 as a potential problem for widespread rollout.[50] Only approximately 361 k doses of mAbs were administered as of April 2021, relative to the 14.4 million individuals who, in that time period, contracted mild-to-moderate COVID-19 and who could have benefited from the mAbs treatment (based on data compiled by PRA Health Sciences).

As of July 2021, protocols for administration of various mAbs for treatment of COVID-19 have been established. These are illustrated in the tables below.

Fact Sheet, Emergency Use Authorization (EUA) of Bamlanivimab and Etesevimab (Eli Lilly)[51]

TABLE 1

Recommended Dilution and Administration Instructions for Bamlanivimab and Etesevimab for IV Infusion$^a$ in Patients Weighing 50 kg or More
Drug$^a$: Add 20 mL of bamlanivimab (1 vial) and 40 mL of etesevimab (2 vials) for a total of 60 mL to a prefilled infusion bag and administer as instructed below

| Size of Prefilled 0.9% Sodium Chloride Infusion Bag | Maximum Infusion Rate | Maximum Infusion Time |
|---|---|---|
| 50 mL | 310 mL/hr | 21 minutes |
| 100 mL | 310 mL/hr | 31 minutes |
| 150 mL | 310 mL/hr | 41 minutes |
| 250 mL | 310 mL/hr | 60 minutes |

$^a$700 mg of bamlanivimab and 1,400 mg of etesevimab are added to the same infusion bag and administered together as a single intravenous infusion.

TABLE 2

Recommended Dilution and Administration Instructions for Bamlanivimab and Etesevimab for IV Infusion in Patients Weighing Less Than 50 kg
Drug$^a$: Add 20 mL of bamlanivimab (1 vial) and 40 mL of etesevimab (2 vials) for a total of 60 mL to a prefilled infusion bag and administer as instructed below

| Size of Prefilled 0.9% Sodium Chloride Infusion Bag | Maximum Infusion Rate | Maximum Infusion Time |
|---|---|---|
| 50 mL | 310 mL/hr | 21 minutes |
| 100 mL | 310 mL/hr | 31 minutes |
| 150 mL | 310 mL/hr | 41 minutes |
| 250 mL$^b$ | 266 mL/hr | 70 minutes |

$^a$700 mg of bamlanivimab and 1,400 mg of etesevimab are added to the same infusion bag and administered together as a single intravenous infusion.
$^b$The minimum infusion time for patients weighing less than 50 kg who are administered bamlanivimab and etesevimab together using the 250 mL prefilled 0.9% Sodium Chloride infusion bag must be extended to at least 70 minutes to ensure safe use (endotoxin load).

Fact Sheet, Emergency Use Authorization (EUA) of Casirivimab and Imdevimab (Regeneron)[52]

TABLE 1

Recommended Dilution Instructions for 600 mg of Casirivimab and 600 mg of Imdevimab for Intravenous Infusion

| Size of Prefilled 0.9% Sodium Chloride Infusion Bag | Preparing Using Co-Formulated Casirivimab and Imedvimab Vial | Preparing Casirivimab and Imdevimab Using Individual Vials$^a$ |
|---|---|---|
| 50 mL<br>100 mL<br>150 mL<br>250 mL | Add 10 mL of co-formulated casirivimab and imdevimab (1 vial) into a prefilled 0.9% sodium chloride infusion bag and administer as instructed below | Add: 5 mL of casirivimab (may use 2 vials of 2.5 mL OR 1 vial of 11.1 mL) and 5 mL of imdevimab (may use 2 vials of 2.5 mL OR 1 vial of 11.1 mL) and inject into a prefilled 0.9% sodium chloride infusion bag and administer as instructed below |

$^a$600 mg of casirivimab and 600 mg of imdevimab are added to the same infusion bag and administered together as a single intravenous infusion.

TABLE 2

Recommended Administration Rate for Casirivimab and Imdevimab for Intravenous Infusion.

| Size of Prefilled 0.9% Sodium Chloride Infusion Bag Used | Maximum Infusion Rate | Maximum Infusion Time |
|---|---|---|
| 50 mL$^a$ | 180 mL/hr | 20 minutes |
| 100 mL | 310 mL/hr | 21 minutes |
| 150 mL | 310 mL/hr | 31 minutes |
| 250 mL | 310 mL/hr | 50 minutes |

$^a$The minimum infusion time for patients administered casirivimab and imdevimab together using the 50 mL prefilled 0.9% Sodium Chloride infusion bag must be at least 20 minutes to ensure safe use.

Fact Sheet, Emergency Use Authorization (EUA) of Tocilizumab (Genentech)[53]

Dosage and Administration

The recommended dosage of ACTMERA is a single 60-minute intravenous infusion as follows:
 Patients less than 30 kg weight: 12 mg/kg
 Patients at or above 30 kg weight: 8 mg/kg
If clinical signs or symptoms worsen or do not improve after the first dose, one additional infusion of ACTMERA may be administered at least 8 hours after the initial infusion.
Maximum dosage in COVID-19 patients is 800 mg per infusion.
Preparation and Administration
 For patients less than 30 kg, dilute to 50 mL in 0.9% or 0.45% Sodium Chloride Injection, USP for intravenous infusion using aseptic technique.
 For patients at or above 30 kg, dilute to 100 mL in 0.9% or 0.45% Sodium Chloride Injection, USP for intravenous infusion using aseptic technique.
 Administer as a single intravenous drip infusion over 1 hour; do not administer as bolus or push.
Fact Sheet, Emergency Use Authorization (EUA) of Sotrovimab (Vir Biotechnology)[54]
 Administer one vial (500 mg/8 mL) added into prefilled 50-mL or 100-mL infusion bag containing 0.9% sodium chloride.
 Administer the entire infusion solution in the bag over 30 minutes. Due to potential overfill of prefilled saline bags, the entire infusion solution in the bag should be administered to avoid underdosage.
 Do not administer as an IV push or bolus.
 Clinically monitor patients during infusion and observe patients for at least 1 hour after infusion is complete.

As seen above, the EUA protocols for administration of mAbs for treatment of COVID-19 allow for the use of different size infusion bags, with corresponding minimum infusion times, to be chosen at the discretion of the healthcare provider conducting the infusion. A variety of factors may influence choice of the IV bag size and corresponding mAb concentration and infusion duration. For example, a slower infusion may be desirable where the patient is at greater risk of an infusion-related reaction such that more time is available to identify the reaction and cease treatment, thereby preventing or limiting patient injury. A faster infusion may be desired where the patient is at low risk for infusion-related reactions, although the speed of administration by drip IV is limited by the apparatus being used and by the need to administer a sufficiently dilute concentration of mAbs for adequate distribution in the body.

While some of the above EUA protocols allow for the use of smaller infusion volumes (e.g., 50 mL and 100 mL) and corresponding higher mAb concentrations and shorter minimum infusion times, it is not immediately clear that these options are as well-supported by clinical trial data as the larger infusion volumes (e.g., 250 mL) and corresponding lower mAb concentrations and longer minimum infusion times. For example, in the phase 3 clinical trial of sotrovimab (GSK and Vir Biotechnology), a single 500 mg dose of sotrovimab was administered to each of the 291 patients in the sotrovimab group via a one-hour infusion,[55] while the EUA Fact Sheet for sotrovimab, revised November 2021, instructs administration of 500 mg of sotrovimab via 30 minute infusion using either a 50-mL or 100-mL infusion bag.[56]

Agitation of the mAbs can be caused in normal IV lines with gravity fed administration where drip chambers are used to gauge the flow rate. The drip chambers cause agitation as the infusate forms droplets and falls to the bottom of the drip chamber. Furthermore, higher protein concentrations, as used in subcutaneous administration of mAbs and some drip infusions may increase the viscosity of the infusate, which may increase the aggregation potential of proteins. High mAb concentration may also increase opalescence, which introduces a potential safety issue, for example, because an opalescent solution can be confused with turbid solutions that can result from protein aggregation or other particulate formation. Protocols for mAb infusions may warn the medical provider to look for opalescence as a sign of such aggregation, but high mAb concentration may cause opalescence and make it difficult for a medical provider to judge if the solution is sufficiently clear.

Currently, infusion pumps for the delivery of medications such as insulin and other hormones, antibiotics, chemotherapy drugs, and pain relievers are operated by a trained medical technician who programs a precise rate and duration of fluid delivery through a built-in software interface. These pumps usually have safety features such as alarms to alert users of the detection of air or another blockage in the tubing. Newer medication infusion pumps—sometimes referred to as 'smart pumps'—may alert a user when there is a risk of adverse drug interaction or when the pump rate or other parameters are outside of specified safety limits. Smart pumps may include software that checks programmed infusion rates against preset limits with the goal of reducing the risk of infusion rates that are too high or too low (https://qualitysafety.bmj.com/content/26/2/93). Some metering pumps are bag devices with roller pumps that draw fluid through silicone tubing via rollers. Metering pumps are also called dosing pumps or proportioning pumps and are generally able to deliver liquid with an accuracy of better than 3% across a range of discharge pressures. Certain pump devices involve a controlled screw to draw a small volume of drug from a syringe at a controlled slow rate. Osmotic pumps may also be used for controlled drug delivery, and are generally implanted.

Rapid infusion systems are designed to rapidly administer a large volume of plasma, blood, or other fluid to patients in military or civilian emergency situations, for example, a patient suffering from a traumatic injury such as uncontrolled hemorrhage. These systems typically feature a roller pump, centrifugal pump, or other pump mechanism, often with a warmer or other temperature control device. Examples of rapid infusion systems include the Hotline HL-1200A Rapid Infuser Infusion Pump (capable of infusion rates from 30 mL/min to 1100 mL/min, with maximum rate of 1400 mL/min) (Smiths Group Plc, London, UK); the Belmont® Rapid Infuser RI-2 (capable of infusion rates from 2.5 mL/min to 1000 mL/min), the FMS2000, the Buddy™ and the Buddy Lite™ portable IV & infusion pump (Belmont Medical Technologies, Billerica, Mass.); LifeFlow Rapid Fluid Infuser, and LifeFlow Plus Rapid Fluid and Blood Infuser (capable of 500 mL of fluid in less than 2 min, 20G IV catheter, or 274 mL/min via 18 ga catheter) (410 Medical, Durham, N.C.); Thermacor 1200 (capable of infusion rates from 10 mL/hour to 1200 mL/min) (Smisson-Cartledge Biomedical, Macon, Ga.); The Warrior lite, Warrior, Warrior EXTREME, Warrior Hybrid, and Warrior AC (QinFlow Ltd. of Rosh Ha'ayin Israel); enFlow® IV fluid and blood warming system (CareFusion, Vernon Hills, Ill.); Medi-Temp by Stryker (Kalamazoo, Mich.); Ranger by 3M (St. Paul, Minn.); Level 1 h-1200 Fast Flow Fluid Warmer (Smiths Medical, Dublin, Ohio); and Thermal Angel® blood and IV fluid infusion warmer (Estill Medical Technologies, Inc., Arlington, Tex.). Devices with proprietary tubing sets include the enFlow with a 4-mL priming volume and a flow rate up to 200 mL/minute; the Medi-Temp with a flow rate up to 500 mL/minute; and the Ranger by 3M (St. Paul, Minn.) with a flow rate up to 500 mL/minute. The portable Belmont® Buddy™ system is designed for flow rates up to 100 mL/min for crystalloids at 20° C. and up to 50 mL/min for packed red cells at 10° C. The portable, battery powered Buddy Lite™ system is designed for maximum flow rates of 50-80 mL/min, depending on the input temperature. Pressurized devices for massive transfusion of blood include the Belmont Rapid Infuser RI-2 which can deliver a flow rate of more than 750 mL/minute (e.g., up to 1500 mL/minute); the Level 1 h-1200 Fast Flow Fluid Warmer which can infuse fluids at flows of up to 600 mL/min. Many of the above devices (including the portable devices) include a flow control system and/or other flow and/or metering control devices, such as pressure-regulating valves (PRVs) and/or pressure-responsive valves, to control the specific flow rate of a liquid delivered to the patient and/or to ensure the flow stays below a predetermined maximum flow rate and/or above a predetermined minimum flow rate. Moreover, these flow control devices and/or systems may allow the operator to establish an initial lower flow rate, then increase to a safe higher flow rate if no serious IRRs are observed in the patient.

As used in certain embodiments described herein for administration of mAb and/or pAb treatment, the rapid infusion system would feature air venting, which prevents oxidation of the mAb and/or pAb. Furthermore, in certain embodiments, the rapid infusion system would feature temperature control, which can be important in maintaining the stability of the mAb and/or pAb. Moreover, in certain embodiments, the rapid infusion system would not need a drip pan (e.g., used in drip IVs), which can disturb mAb stability.

These rapid infusion systems are not currently used for administration of drugs. Rapid infusions include those described in any of the following U.S. patents and published patent application, the disclosures of which are incorporated herein by reference: U.S. Pat. Nos. 5,319,170; 6,175,688; 6,236,809; 6,480,257; 7,819,875; 9,737,672; 10,293,099; and 10,485,936; and U.S. Patent Application Publication No. 2009/0192446 (U.S. patent application Ser. No. 12/228,618).

The fact sheet for health care providers under the Emergency Use Authorization (EUA) of bamlanivimab and etesevimab (Eli Lilly) describes the authorized dosage as 700 mg bamlanivimab and 1400 mg etesevimab administered together as a single intravenous (IV) infusion of 700 mg, administered in either a 250 mL, 150 mL, 100 mL, or 50 mL bag over a minimum of at least 60 minutes, 41 minutes, 31 minutes, or 21 minutes, respectively, via pump or gravity. Patients are to be monitored during administration and observed for at least one hour after infusion is complete. The prescribed maximum infusion rate is 310 mL/hr (5.17 mL/min), regardless of the size bag used.

By increasing the infusion rate from 5.17 mL/min to 50 mL/min, the time required for an infusion of the 700 mg/1400 mg (bamlanivimab/etesevimab) dose in the 250 mL solution could decrease from 60 minutes to 5 minutes—that is, a dosing rate that increases from 35 mg/min to 420 mg/min. Existing rapid infusion systems, which are currently designed for rapid transfer of plasma and other biological fluids, not drugs, are easily capable of achieving flow rates of 50 mL/min to 80 mL/min, for example.

Administration by rapid infusion device has the added benefit of enabling administration of mAbs at a lower concentration and higher volume, thereby potentially reducing the incidence of infusion-related reactions and/or promoting better distribution of drug throughout the body.

For example, the 700 mg+1400 mg (bamlanivimab/etesevimab) dose can be diluted to a 250 mL solution as in the most dilute solution indicated in the EUA fact sheet, yet delivered much more rapidly than the prescribed minimum 60 minutes (e.g., 5 minutes or less).

For example, mAbs or pAbs can be rapidly administered by a rapid infusion device in dilute solutions of less than or equal to 10 mg/mL, less than or equal to 9 mg/mL, less than or equal to 8.5 mg/mL, less than or equal to 8 mg/mL, less than or equal to 7 mg/mL, less than or equal to 6 mg/mL, less than or equal to 5 mg/mL, less than or equal to 4.5 mg/mL, less than or equal to 4 mg/mL, less than or equal to 3.5 mg/mL, less than or equal to 3.0 mg/mL, less than or equal to 2.5 mg/mL, or less than or equal to 2.0 mg/mL.

Rapid infusion systems include convenient portable systems, for example, systems with a total weight (including heater, battery, and disposable) less than 5 lbs, and preferably less than 3 lbs, and more preferably less than 2 lbs. An example is the aforementioned portable Belmont® Buddy™ system with a total weight (including heater, battery, and disposable) less than 1.6 lbs. Such portable rapid infusion systems can be conveniently used in the home, for example. Certain existing rapid infusion systems may be certified for use in the administration of drugs and/or adapted (e.g., retrofitted or redesigned) for use in the administration of drugs.

In general, administration of lower concentration/higher volume mAbs or pAbs requires additional time for administration. In certain embodiments, rapid infusion may facilitate faster/more efficient administration of a more desirable lower-concentration/higher volume mAb or pAb solution to a patient, e.g., where lower concentration/higher volume mAb or pAb solution is more effective and/or safer for the patient than a higher concentration/lower volume mAb or pAb solution.

Administration of mAbs by rapid infusion allows the flexibility to administer higher volumes of lower concentration mAbs in a short amount of time, where it would be desirable to do so. For example, to reduce infusion duration using an IV drip, it is necessary to use a lower volume/higher concentration mAbs infusate. Rapid infusion avoids the drawbacks associated with use of higher mAbs concentrations and/or lower infusate volumes. For example, rapid infusion can deliver the same mAbs dose at a lower mAbs concentration (and higher infusate volume) more quickly than infusion via IV drip.

Furthermore, as explained in more detail herein, unlike normal IV lines with gravity fed administration (drip IV), a rapid infusion device does not need a drip chamber to gauge flow rates, since a software-controlled pump is used to administer the fluids. By eliminating the drip chamber, a rapid infusion device provides for administration of mAbs with reduced agitation of the mAbs and infusate, as compared to administration by drip IV. The reduced agitation can help avoid problems due to mAbs instability, aggregation, and protein unfolding, potentially improving efficacy. This is described in more detail in the Appendix, attached hereto.

Moreover, because of the relative hydrophobicity of air compared to water, proteins may adsorb at the air-water interface, forming layers. Significant volumes of air may be inherently present in IV infusion lines, which a rapid infusion device completely eliminates. Air can be present within the IV line due to pre-existing air within the fluid bag, introduction of air during the bag spiking process, or incomplete priming efforts. A rupture of these protein absorption layers at air interfaces leads to the formation of protein aggregates in the solution. Removing oxygen in the IV line suppresses aggregation due to the elimination of air interfaces. In certain embodiments in which the rapid infusion device comprises a warmer, the rapid infusion device eliminates air as it is naturally outgassed from the solution during the warming process. The solubility of gases in liquids decreases with increasing temperature. As fluid is warmed to normothermic body temperature, any dissolved gases will come out of solution. By collecting and eliminating this air, the rapid infusion device potentially avoids excess protein aggregation from infusion in the body and potential aggregation that would otherwise have been formed within the body if the infusion was not pre-warmed to normothermic temperature prior to infusion. Furthermore, oxidation may cause a reduction in binding affinity and mAb potency. Removing dissolved oxygen in solution suppresses oxidation effects of mAbs, and the rapid infusion device, therefore, protects mAb potency. This is described in more detail in the Exemplary Embodiments section.

The ability to more effectively deliver mAbs and pAbs therapeutics (e.g., COVID-19 therapeutics) in an outpatient, SNF, or home setting to patients, e.g., those with mild to moderate disease, has the potential to provide more and better care at a lower overall cost by reducing resource utilization by the healthcare provider and by reducing the need for inpatient hospitalization.

Presented herein are methods, systems, and apparatus for administering a monoclonal and/or polyclonal antibody treatment via rapid infusion, e.g., for the treatment of a disease or condition, e.g., a disease caused by a pathogen, e.g., for the treatment of COVID-19, caused by the virus SARS-CoV-2, or for the treatment of other conditions, such as various kinds of cancer (e.g., leukemia); neurological disorders such as Alzheimer's disease, Parkinson's disease, and migraine; autoimmune diseases such as rheumatoid arthritis, Crohn's disease, lupus, and ulcerative colitis; dermatitis; arthritis; psoriasis; asthma and other respiratory diseases; multiple sclerosis; macular degeneration; and for treatment of organ and tissue transplant patients, where said treatment otherwise would require lengthy (and, potentially, numerous) infusions of monoclonal and/or polyclonal antibodies.

In another aspect, the invention is directed to a kit for administering a monoclonal and/or polyclonal antibody treatment via a rapid infusion device (e.g., for the treatment of a disease, e.g., a disease caused by a pathogen, e.g., for the treatment of COVID-19, caused by the virus SARS-CoV-2) according any of the methods described herein.

In certain embodiments, a rapid infusion device suitable for use in the administration of a drug may comprise flow rate control equipment that allows an operator to set and/or vary the flow rate of drug solution to the patient during infusion.

In some embodiments, rapid infusion begins at a lower initial flow rate and may be increased after the patient experiences no serious adverse infusion-related reactions that would indicate discontinuing the infusion.

In another aspect, the invention is directed to a method for administering a monoclonal and/or polyclonal antibody treatment via a rapid infusion device (e.g., a low flow rapid infusion) (e.g., for the treatment of a disease, e.g., a disease caused by a pathogen, e.g., for the treatment of COVID-19, caused by the virus SARS-CoV-2), the method comprising: administering by intravenous infusion a volume of solution (e.g., a sodium chloride solution) comprising one or more (e.g., a cocktail of) monoclonal and/or polyclonal antibodies to a patient using a rapid infusion device, wherein the rapid infusion device comprises a pump (e.g., a roller pump or centrifugal pump) and a tubing line or lines, wherein the tubing line or lines fluidly connect (e.g., directly or indirectly) (i) an intravenous (IV) bag or other receptacle containing the volume of solution to the pump and (ii) the pump to the patient, for intravenous delivery of the volume of solution to the patient, wherein one, two, or all three of (a), (b), and (c), as follows, applies: (a) the pump administers the volume of solution to the patient at a flow rate substantially faster than by gravity alone (e.g., at a flow rate of at least 10 mL/min, or at least 15 mL/min, or at least 20 mL/min, or at least 25 mL/min, or at least 30 mL/min, or at least 35 mL/min, or at least 40 mL/min, or at least 45 mL/min, or at least 50 mL/min); (b) the pump administers the volume of solution at a dosing rate of at least 35 mg of the one or more monoclonal and/or polyclonal antibodies (e.g., combined) per minute (e.g., at least 40 mg/min, at least 50 mg/min, at least 60 mg/min, at least 70 mg/min, at least 80 mg/min, at least 90 mg/min, at least 100 mg/min, at least 125 mg/min, at least 150 mg/min, at least 175 mg/min, at least 200 mg/min, at least 225 mg/min, at least 250 mg/min, at least 275 mg/min, at least 300 mg/min, at least 325 mg/min, at least 350 mg/min, at least 375 mg/min, or at least 400 mg/min of the one or more monoclonal and/or polyclonal antibodies (e.g., combined)) and/or at a total [mAb(s) and/or pAb(s)] concentration of less than or equal to 20 mg/mL, less than or equal to 15 mg/mL, less than or equal to 10 mg/mL, less than or equal to 9 mg/mL, less than or equal to 8.5 mg/mL, less than or equal to 8 mg/mL, less than or equal to 7 mg/mL, less than or equal to 6 mg/mL, less than or equal to 5 mg/mL, less than or equal to 4.5 mg/mL, less than or equal to 4 mg/mL, less than or equal to 3.5 mg/mL, less than or equal to 3.0 mg/mL, less than or equal to 2.5 mg/mL, or less than or equal to 2.0 mg/mL [total mg mAb(s) and/or pAb(s) per mL IV solution e.g., aqueous solution e.g., saline solution]; and (c) administration of the volume of solution to the patient is completed in no more than 30 minutes (e.g., no more than 25 minutes, e.g., no more than 20 minutes, e.g., no more than 15 minutes, e.g., no more than 10 minutes, e.g., no more than 7 minutes, e.g., no more than 5 minutes, e.g., no more than 4 minutes, e.g., no more than 3 minutes).

In some embodiments, the one or more monoclonal and/or polyclonal antibodies comprises a monoclonal and/or polyclonal antibody (or cocktail of antibodies) for the treatment of one or more members selected from the group consisting of cancer (e.g., colorectal, lung, glioblastoma, kidney, breast, stomach, esophageal, cervical, or ovarian cancer, or multiple myeloma, soft tissue sarcoma, lymphoma, melanoma, neuroblastoma, or leukemia), a neurological disease or condition {e.g., Alzheimer's disease (AD), Parkinson's disease (PD); Duchene's muscular dystrophy (DMD); multiple sclerosis (MS); myasthenia gravis; migraine; migraine and cluster headache; neuromyelitis optica spectrum disorder (NMOSD); idiopathic inflammatory myopathies (IIM); immune-related peripheral neuropathies (multifocal motor neuropathy (MMN), anti-myelin associate glycoprotein (anti-MAG) neuropathy, chronic inflammatory demyelinating polyneuropathy (CIDP)); or a neurooncological condition (e.g., malignant glioma or recurrent glioblastoma)}; dermatitis; psoriasis; asthma or other respiratory disease; macular degeneration; an autoimmune disease (e.g., rheumatoid arthritis, Crohn's disease, lupus, or ulcerative colitis); cytokine release syndrome; Castelman disease; a disease caused by a pathogen (e.g., infection or other disease caused by a virus, bacteria, fungus, or protozoa); and organ and/or tissue transplant.

In some embodiments, the one or more monoclonal and/or polyclonal antibodies comprises a member selected from the group consisting of the following: an anti-inflammatory (e.g., infliximab, adalimumab, basiliximab, daclizumab, or omalizumab); an anti-cancer (e.g., gemtuzumab, alemtuzumab, rituximab, trastuzumab, nimotuzumab, cetuximab, or bevacizumab & ranibizumab); an anti-cancer and anti-viral (e.g., bavituximab); palivizumab; and abciximab.

In some embodiments, the method is performed for the treatment of COVID-19 (i.e., caused by the virus SARS-CoV-2) [e.g., wherein the one or more monoclonal and/or polyclonal antibodies comprises one or more members selected from the group consisting of bamlanivimab (aka LY-CoV555, Eli Lilly); bamlanivimab and etesevimab antibody cocktail (aka LY-CoV555 (bamlanivimab)+JS016 (etesevimab) antibody cocktail, Eli Lilly); casirivimab and imdevimab antibody cocktail (aka REGN-COV2 aka REGEN-COV™ aka REGN10933+REGN10987, aka Ronapreve, Regeneron, Roche); gimsilumab (Roivant Sciences); tocilizumab (aka Actemra, Genentech); B38, H4, B5 and/or H2 Capital Medical University, Beijing; COVI-GUARD™ (STI-1499) and/or COVI-AMG™ (STI-2020) (Sorrento Therapeutics); regdanvimab aka Regkirona (Celltrion); sotrovimab (aka VIR-7831 aka Xevudy) and/or VIR-7832, Vir Biotechnology); and tixagevimab and cilgavimab antibody cocktail (aka Evusheld, AstraZeneca)].

In some embodiments, the method is performed for the treatment of a neurological disease or condition {e.g., Alzheimer's disease (AD), Parkinson's disease (PD); Duchene's muscular dystrophy (DMD); multiple sclerosis (MS);

myasthenia gravis; migraine; migraine and cluster headache; neuromyelitis optica spectrum disorder (NMOSD); idiopathic inflammatory myopathies (IIM); immune-related peripheral neuropathies (multifocal motor neuropathy (MMN), anti-myelin associate glycoprotein (anti-MAG) neuropathy, chronic inflammatory demyelinating polyneuropathy (CIDP)); or a neurooncological condition (e.g., malignant glioma or recurrent glioblastoma)} [e.g., wherein the one or more monoclonal antibodies comprises one or more members selected from the group consisting of aducanumab (Biogen Inc.), gantenerumab (Chugai Pharmaceutical Co., Ltd., Hoffmann-La Roche), donanemab (Eli Lilly and Company), BAN2401 (Eisai Co., Ltd. and Biogen Inc.), gosuranemab (Biogen Inc., Bristol-Myers Squibb), zagotenemab (Eli Lilly and Company), tilavonemab (AbbVie, C2N Diagnostics, LLC), semorinemab (AC Immune SA, Genentech, Hoffmann-La Roche), cinpanemab (Biogen, Neurimmune), MEDI1341 (AstraZeneca, Takeda Pharmaceutical Company), domagrozumab (Pfizer Inc.), natalizumab (humanized Ab directed against α4 β1 integrin) (Biogen Inc.), alemtuzumab (Sanofi), ocrelizumab (Genentech USA, Inc.), ofatumumab (Novartis Pharmaceuticals Corporation), inebilizumab (Horizon Therapeutics plc), erenumab (Amgen Inc.), fremanezumab (Teva Pharmaceuticals USA, Inc.), eptinezumab (Lundbeck), galcanezumab (Lilly USA, LLC), rituximab (Amgen Inc.), eculizumab (Alexion Pharmaceuticals, Inc.), tocilizumab (Genentech, Inc.), satralizumab (Genentech USA, Inc.), ravulizumab (Alexion Pharmaceuticals, Inc.), aquaporumab, infliximab (Amgen Inc.), rozanolixizumab, nipocalimab (Johnson & Johnson Inc.), batoclimab (Harbour BioMed), efgartigimod (Argenx), bevacizumab (Pfizer Inc.), and rilotumumab (Amgen, Inc.).

In some embodiments, the one or more monoclonal antibodies comprises one or more members selected from the group consisting of: pembrolizumab (Keytruda), manufactured by Merck for treatment of cancer; nivolumab (Opdivo), manufactured by Bristol Myers Squibb, for various forms of cancer; bevacizumab (Avastin), manufactured by Roche, for colorectal, lung, glioblastoma, kidney, cervical, and/or ovarian cancer; ocrelizumab (Ocrevus), manufactured by Roche, for relapsing or primary progressive multiple sclerosis; rituximab (Rituxan), manufactured by Roche, Pharmstandard, for various autoimmune diseases and cancers; daratumumab (Darzalex), manufactured by Janssen (Johnson & Johnson), for multiple myeloma; pertuzumab (Perjeta), manufactured by Roche, for HER2-positive breast cancer; trastuzumab (Herceptin), manufactured by Genentech (Roche), for breast, stomach, and esophageal cancer; infliximab (Remicade), manufactured by Janssen (Johnson & Johnson), for Crohn's disease, ulcerative colitis, rheumatoid arthritis, ankylosing spondylitis, psoriatic arthritis, and plaque psoriasis; tocilizumab (Actemra/RoActemra), manufactured by Roche, for rheumatoid arthritis, forms of juvenile idiopathic arthritis and giant cell arteritis as well as CAR T cell-induced severe or life-threatening cytokine release syndrome; atezolizumab (Tecentriq), manufactured by Roche, for urothelial carcinoma, non-small cell lung cancer, and triple-negative breast cancer; tositumomab-l131 (Bexxar), manufactured by GSK, for non-Hodgkin lymphoma; olaratumab (Lartruvo), manufactured by Eli Lilly, for soft tissue sarcoma; MabThera, rituximab (Rituxan), manufactured by Biogen/Genentech, for non-Hodgkin lymphoma; basiliximab (Simulect), manufactured by Novartis, for prevention of kidney transplant rejection; ibritumomab tiuxetan (Zevalin), manufactured by Spectrum, for non-Hodgkin lymphoma; cetuximab (Erbitux), manufactured by Bristol Meyers Squibb, Eli Lilly, and Merck, for colorectal cancer; natalizumab (Tysabri), manufactured by Biogen/Elan, for multiple sclerosis; panitumumab (Vectibix), manufactured by Amgen, for colorectal cancer; ranibizumab (Lucentix), manufactured by Genentech/Novartis, for macular degeneration; eculizumab (Soliris), manufactured by Alexion, for paroxysmal nocturnal hemoglobinuria; ofatumumab (Arzerra), manufactured by Novartis, for chronic lymphocytic leukemia; belimumab (Benlysta), manufactured by Human Genome Sciences, for systemic lupus erythematosus; ipilimumab (Yervoy), manufactured by Bristol Meyers Squibb, for metastatic melanoma; pertuzumab (Perjeta), manufactured by Genentech, for breast cancer; raxibacumab, manufactured by Human Genome Sciences, for anthrax infection; obinutuzumab (Gazyva, Gazyvaro), manufactured by Genentech, for chronic lymphocytic leukemia; siltuximab (Sylvant), manufactured by Janssen Biotech), for Castelman disease; ramucirumab (Cyramza), manufactured by Eli Lilly, for gastric cancer; vedolizumab (Entyvio), manufactured by Takeda, for ulcerative colitis, Crohn's disease; alemtuzumab (Lemtrada, MabCampath, Campath-1H), manufactured by Genzyme, for multiple sclerosis and chronic myeloid leukemia, necitumumab (Portrazza), manufactured by Eli Lilly, for non-small cell lung cancer; dinutuximab (Qarziba, Unituxin), manufactured by United Therapeutics, for neuroblastoma; elotuzumab (Empliciti), manufactured by Bristol Meyers Squibb, for multiple myeloma; reslizumab (Cinqaero, Cinqair), manufactured by Teva, for asthma; bezlotoxumab (Zinplava), manufactured by Merck Sharp Dohme, for prevention of *Clostridium difficile* infection recurrence; obiltoxaximab (Anthim), for prevention of inhalational anthrax; avelumab (Bavencio), manufactured by Merck, for Merkel cell carcinoma; and durvalumab (Imfinzi), manufactured by AstraZeneca, for bladder cancer.

In some embodiments, the method is performed for the treatment of an organ and/or tissue transplant patient [e.g., wherein the one or more polyclonal and/or monoclonal antibodies comprises one or more members selected from the group consisting of anti-thymocyte globulin [rabbit] (Thymoglobulin, Sanofi), lymphocyte immune globulin, anti-thymocyte globulin [equine] sterile solution (Atgam, Pfizer), alemtuzumab (Sanofi), rituximab (Amgen Inc), alpha-1 antitrypsin, and a double antibody conjugate that is an anti-CD3 and anti-CD7 agent].

In some embodiments, the rapid infusion device comprises a flow control value or other feature that limits flow of fluid to the patient to no greater than a predetermined maximum flow rate.

In some embodiments, the rapid infusion device delivers the volume of solution to the patient at a rate that approximates a predetermined fixed rate (e.g., within 30%, or within 25%, or within 20%, or within 15%, or within 10%, or within 5%, or within 2%, or within 1% of the predetermined fixed rate) (e.g., wherein the rapid infusion device is designed for operation at a single approximate rate, e.g., to avoid noncompliance with a prescribed solution delivery rate).

In some embodiments, the method includes using a disposable infusion set for connection to the rapid infusion device, e.g., wherein the disposable infusion set comprises one or more members of the group consisting of: a needle (e.g., straight steel needle), one or more lengths of tubing, and an adhesive support (e.g., to avoid dislodging of the needle).

In some embodiments, the rapid infusion device comprises an elastomeric (e.g., ball) pump, wherein the pump comprises the receptacle containing the volume of solution, and wherein the tubing line or lines fluidly connect (e.g., directly or indirectly) the pump (and, therefore, the receptacle containing the volume of solution) to the patient, for intravenous delivery of the volume of solution to the patient.

In some embodiments, the rapid infusion device comprises a heater and/or an air venting mechanism (e.g., wherein the rapid infusion device does not comprise dripping chambers or a drip pan as used in drip I.V. infusers).

In some embodiments, the rapid infusion device comprises a filter for filtering out particles (e.g., monoclonal antibody aggregates and/or polyclonal antibody aggregates) from the volume of solution prior to (upstream of) delivery of the filtered solution to the patient.

In some embodiments, the filter has a size small enough (e.g., a mesh tight enough) to catch the particles (e.g., monoclonal antibody aggregates and/or polyclonal antibody aggregates) (e.g., wherein the filter has a size below 170 microns, e.g., below 150 microns, e.g., below 125 microns, e.g., below 100 microns, e.g., below 75 microns, e.g., below 50 microns, e.g., below 40 microns, e.g., below 30 microns, e.g., below 20 microns, e.g., below 10 microns, e.g., below 8 microns, e.g., below 5 microns, e.g., below 4 microns, e.g., below 2 microns, e.g., below 1 micron, e.g., below 0.7 micron, e.g., below 0.5 micron, e.g., below 0.3 micron, e.g., about 0.2 μm).

In some embodiments, the rapid infusion device is portable and/or is designed for a single use.

In another aspect, the invention is directed a rapid infusion device for administering by intravenous infusion a volume of solution (e.g., a sodium chloride solution) comprising one or more (e.g., a cocktail of) monoclonal and/or polyclonal antibodies to a patient, the rapid infusion device comprising: a pump (e.g., a roller pump or centrifugal pump); and a tubing line or lines, wherein the tubing line or lines fluidly connect (e.g., directly or indirectly) (i) an intravenous (IV) bag or other receptacle containing the volume of solution to the pump and (ii) the pump to the patient, and wherein the pump is configured such that one, two, or all three of (a), (b), and (c), as follows, applies: (a) the pump is capable of administering the volume of solution to the patient at a flow rate substantially faster than by gravity alone (e.g., at a flow rate of at least 10 mL/min, or at least 15 mL/min, or at least 20 mL/min, or at least 25 mL/min, or at least 30 mL/min, or at least 35 mL/min, or at least 40 mL/min, or at least 45 mL/min, or at least 50 mL/min); (b) the pump is capable of administering the volume of solution at a dosing rate of at least 35 mg of the one or more monoclonal and/or polyclonal antibodies (e.g., combined) per minute (e.g., at least 40 mg/min, at least 50 mg/min, at least 60 mg/min, at least 70 mg/min, at least 80 mg/min, at least 90 mg/min, at least 100 mg/min, at least 125 mg/min, at least 150 mg/min, at least 175 mg/min, at least 200 mg/min, at least 225 mg/min, at least 250 mg/min, at least 275 mg/min, at least 300 mg/min, at least 325 mg/min, at least 350 mg/min, at least 375 mg/min, or at least 400 mg/min of the one or more monoclonal and/or polyclonal antibodies (e.g., combined)) and/or at a total [mAb(s) and/or pAb(s)] concentration of less than or equal to 20 mg/mL, less than or equal to 15 mg/mL, less than or equal to 10 mg/mL, less than or equal to 9 mg/mL, less than or equal to 8.5 mg/mL, less than or equal to 8 mg/mL, less than or equal to 7 mg/mL, less than or equal to 6 mg/mL, less than or equal to 5 mg/mL, less than or equal to 4.5 mg/mL, less than or equal to 4 mg/mL, less than or equal to 3.5 mg/mL, less than or equal to 3.0 mg/mL, less than or equal to 2.5 mg/mL, or less than or equal to 2.0 mg/mL [total mg mAb(s) and/or pAb(s) per mL IV solution, e.g., aqueous solution e.g., saline solution]; and (c) the pump is capable of administering the volume of the solution in no more than 30 minutes (e.g., no more than 25 minutes, e.g., no more than 20 minutes, e.g., no more than 15 minutes, e.g., no more than 10 minutes, e.g., no more than 7 minutes, e.g., no more than 5 minutes, e.g., no more than 4 minutes, e.g., no more than 3 minutes).

In some embodiments, the device comprises a flow control valve or other feature that limits flow of fluid to the patient to no greater than a predetermined maximum flow rate.

In some embodiments, the rapid infusion device is capable of delivering the volume of solution to the patient at a rate that approximates a predetermined fixed rate (e.g., within 30%, or within 25%, or within 20%, or within 15%, or within 10%, or within 5%, or within 2%, or within 1% of the predetermined fixed rate) (e.g., wherein the rapid infusion device is designed for operation at a single approximate rate, e.g., to avoid noncompliance with a prescribed solution delivery rate).

In some embodiments, the rapid infusion device includes a disposable infusion set, e.g., wherein the disposable infusion set comprises one or more members of the group consisting of: a needle (e.g., straight steel needle), one or more lengths of tubing, and an adhesive support (e.g., to avoid dislodging of the needle).

In some embodiments, the rapid infusion device comprises an elastomeric (e.g., ball) pump, wherein the pump comprises the receptacle containing the volume of solution, and wherein the tubing line or lines fluidly connect (e.g., directly or indirectly) the pump (and, therefore, the receptacle containing the volume of solution) to the patient, for intravenous delivery of the volume of solution to the patient.

In some embodiments, the rapid infusion device comprises a heater and/or an air venting mechanism (e.g., wherein the rapid infusion device does not comprise dripping chambers or a drip pan as used in drip I.V. infusers).

In some embodiments, the rapid infusion device comprises a filter for filtering out particles (e.g., monoclonal antibody aggregates and/or polyclonal antibody aggregates) from the volume of solution prior to (upstream of) delivery of the filtered solution to the patient.

In some embodiments, the filter has a size small enough (e.g., a mesh tight enough) to catch the particles (e.g., monoclonal antibody aggregates and/or polyclonal antibody aggregates) (e.g., wherein the filter has a size below 170 microns, e.g., below 150 microns, e.g., below 125 microns, e.g., below 100 microns, e.g., below 75 microns, e.g., below 50 microns, e.g., below 40 microns, e.g., below 30 microns, e.g., below 20 microns, e.g., below 10 microns, e.g., below 8 microns, e.g., below 5 microns, e.g., below 4 microns, e.g., below 2 microns, e.g., below 1 micron, e.g., below 0.7 micron, e.g., below 0.5 micron, e.g., below 0.3 micron, e.g., about 0.2 μm).

In some embodiments, the rapid infusion device is portable and/or is designed for a single use (e.g., wherein the rapid infusion device has a total weight (e.g., including heater, battery, and disposable) less than 5 lbs., e.g., less than 3 lbs., e.g., less than 2 lbs.).

In another aspect, the invention is directed a kit for administering a monoclonal and/or polyclonal antibody treatment via a rapid infusion device (e.g., for the treatment of a disease) (e.g., for the treatment of a disease caused by a pathogen, e.g., for the treatment of COVID-19, caused by the virus SARS-CoV-2) according to the method of any one of the preceding claims.

In certain embodiments, a rapid infusion device suitable for use in the administration of a drug (e.g., a monoclonal antibody or antibody cocktail, e.g., for the treatment of COVID-19) may include a flow control system, a flow control valve (e.g., pressure-regulating valve, PRV), and/or other equipment that ensures no flow greater than a prescribed maximum flow rate is capable of being delivered to the patient when the rapid infusion device is in operation to deliver the drug solution.

In certain embodiments, a rapid infusion device suitable for use in the administration of a drug (e.g., a monoclonal antibody or antibody cocktail, e.g., for the treatment of COVID-19) may include flow and/or metering control that ensures a steady flow rate of the drug solution is delivered to the patient.

BRIEF DESCRIPTION OF DRAWINGS

The foregoing and other objects, aspects, features, and advantages of the present disclosure will become more apparent and better understood by referring to the following description taken in conjunction with the accompanying drawings, in which.

Figure 1:
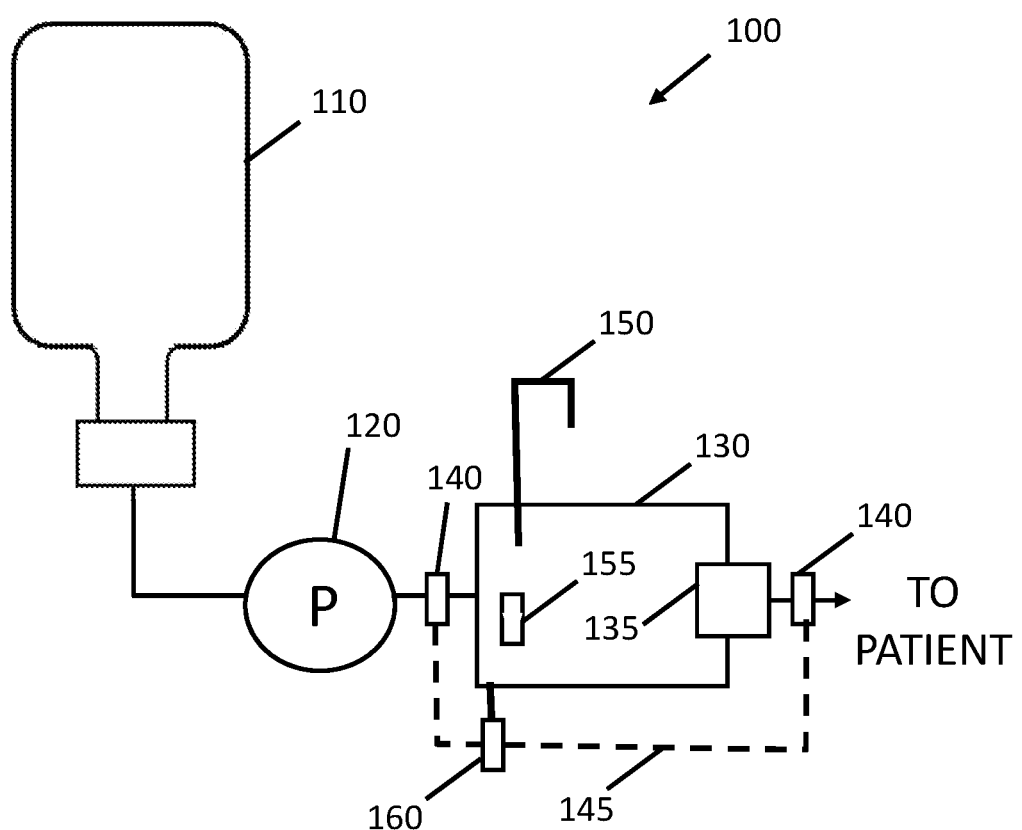
FIG. 1 shows a system and device for administering a monoclonal and/or polyclonal antibody solution via rapid infusion, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

In one aspect, the invention is directed to a system for administering a monoclonal and/or polyclonal antibody treatment via a rapid infusion device (e.g., for the treatment of a disease caused by a pathogen, e.g., for the treatment of COVID-19, caused by the virus SARS-CoV-2), the system comprising: a volume of solution administered by intravenous infusion (e.g., an aqueous sodium chloride solution) comprising one or more (e.g., a cocktail of) monoclonal and/or polyclonal antibodies to a patient using a rapid infusion device, wherein the rapid infusion device comprises a pump (e.g., a roller pump or centrifugal pump, e.g., a centrifugal pump has a motor that supplies rotational energy, and the pump transports fluid by converting rotational kinetic energy to the hydrodynamic energy of the fluid flow) and a tubing line or lines, wherein the tubing line or lines fluidly connect directly or indirectly (i) an intravenous (IV) bag or other receptacle containing the volume of solution to the pump and (ii) the pump to the patient, for intravenous delivery of the volume of solution to the patient, wherein one, two, or all three of (a), (b), and (c), as follows, applies: (a) the pump administers the volume of solution to the patient substantially faster than by gravity alone, at a flow rate ranging from at least 5.17 mL/min or in some embodiments 6.5 mL/min to at least 300 mL/min; (b) the pump administers the volume of solution at a dosing rate ranging from at least 35 mg/min to at least 400 mg/min of the one or more monoclonal and/or polyclonal antibodies and/or combinations thereof and/or at a total [total mg mAb(s) and/or pAb(s) per mL IV solution, e.g., aqueous solution, e.g., saline solution] concentration ranging from at most 20 mg/mL to at most 2.0 mg/mL; and (c) administration of the volume of solution to the patient is completed in a range of no more than 40 minutes to no more than 3 minutes.

In certain embodiments, the rapid infusion device comprises a flow control valve or other feature that limits flow of fluid to the patient to no greater than a predetermined maximum flow rate.

In certain embodiments, the rapid infusion device delivers the volume of solution to the patient at a rate that approximates a predetermined fixed rate within the range of 1% to 30% of the predetermined fixed rate to avoid noncompliance with a prescribed solution delivery rate.

In certain embodiments, the rapid infusion device delivers the volume of solution to the patient at a rate that approximates a predetermined fixed rate within the range of 1% to 30% of the predetermined fixed rate to avoid noncompliance with a prescribed solution delivery rate, wherein the rapid infusion device is designed for operation at a single approximate rate.

In certain embodiments, the rapid infusion device permits a lower initial flow rate then a faster controlled flow rate, permitting but not requiring a higher flow rate after no serious IRRs are observed in the patient at the lower initial flow rate.

In certain embodiments, the method comprises using a disposable infusion set for connection to the rapid infusion device, e.g., wherein the disposable infusion set comprises one or more members of the group consisting of: a needle (e.g., straight steel needle), one or more lengths of tubing, an infusion bag, and an adhesive support (e.g., to avoid dislodging of the needle).

In certain embodiments, the rapid infusion device comprises a heater and/or an air venting mechanism, wherein the rapid infusion device does not comprise dripping chambers or a drip pan as used in drip I.V. infusers.

In certain embodiments, the rapid infusion device comprises a filter for filtering out particles from the volume of solution prior to (upstream of) delivery of the filtered solution to the patient.

In certain embodiments, the filter has a mesh size suitable to catch particles, wherein the filter mesh size ranges from at most 170 μm to at most 0.2 μm.

In certain embodiments, the rapid infusion device is portable and/or is designed for a single use.

In certain embodiments, the rapid infusion device comprises a pressure infusion bag (e.g., IV bag inserted into a cuff with an inflatable bladder, e.g., inflated at 300 mmHg, putting pressure on the contents of the IV bag.

In certain embodiments, the pressure infusion bag device comprises a flow control valve to limit flow to a prescribed maximum.

In certain embodiments, the rapid infusion device is portable and/or is designed for a single use, wherein the rapid infusion device has a total weight ranging from at most 5 lbs to at most 2 lbs.

In certain embodiments, the rapid infusion device comprises an elastomeric pump, wherein the pump comprises the receptacle containing the volume of solution, and wherein the tubing line or lines fluidly connect directly or indirectly the pump (and, therefore, the receptacle containing the volume of solution) to the patient, for intravenous delivery of the volume of solution to the patient.

In certain embodiments, the rapid infusion device may include a disposable set with a sterile fluid path intended for single-use, with standard luer connectors for connection to a standard catheter and a pressure-regulating valve (PRV) at the input to protect the disposable set and the patient from unintended exposure to high pressure applied to the IV line, wherein the PRV may allow an increase of flow from a low level to a higher level by application of a pressure (e.g., up to 300 mmHg), but will prevent pressure higher than this from reaching the set or IV line distal to it.

In certain embodiments, the rapid infusion device may also include a check valve at the output to prevent back flow.

In certain embodiments, the solution is a crystalloid solution (e.g., an aqueous solution of sodium chloride and/or dextrose).

In certain embodiments, the solution is a colloidal solution (e.g., an aqueous solution comprising albumin, dextrans, gelatin, and/or hydroxyethyl starch (HES)).

In certain embodiments, the one or more monoclonal and/or polyclonal antibodies comprises a monoclonal and/or polyclonal antibody (or cocktail of antibodies) for the treatment of one or more members selected from the group consisting of cancer (e.g., colorectal, lung, glioblastoma, kidney, breast, stomach, esophageal, cervical, or ovarian cancer, or multiple myeloma, soft tissue sarcoma, lymphoma, melanoma, neuroblastoma, or leukemia), a neurological disease or condition {e.g., Alzheimer's disease (AD), Parkinson's disease (PD); Duchene's muscular dystrophy (DMD); multiple sclerosis (MS); myasthenia gravis; migraine; migraine and cluster headache; neuromyelitis optica spectrum disorder (NMOSD); idiopathic inflammatory myopathies (IIM); immune-related peripheral neuropathies (multifocal motor neuropathy (MMN), anti-myelin associate glycoprotein (anti-MAG) neuropathy, chronic inflammatory demyelinating polyneuropathy (CIDP)); or a neurooncological condition (e.g., malignant glioma or recurrent glioblastoma)}; dermatitis; psoriasis; asthma or other respiratory disease; macular degeneration; an autoimmune disease (e.g., rheumatoid arthritis, Crohn's disease, lupus, or ulcerative colitis); cytokine release syndrome; Castelman disease; a disease caused by a pathogen (e.g., infection or other disease caused by a virus, bacteria, fungus, or protozoa); and organ and/or tissue transplant. For example, in certain embodiments where the one or more monoclonal and/or polyclonal antibodies comprises a monoclonal and/or polyclonal antibody (or cocktail of antibodies) approved for the treatment of a disease caused by a pathogen, the pathogen comprises one or more of the following: Adenovirus, Herpes simplex, type 1, Herpes simplex, type 2, a coronavirus (e.g., SARS-CoV-2, previously called 2019-nCoV, variant strain SARS-CoV-2 VUI 202012/01, Severe acute respiratory syndrome coronavirus (SARS-CoV), and Middle East Respiratory Syndrome Coronavirus (MERS-CoV)), Varicella-zoster virus, Epstein-Barr virus, Human cytomegalovirus, Human herpesvirus, type 8, Human papillomavirus, BK virus, JC virus, Smallpox, Hepatitis B virus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, TBE virus, Rubella virus, Hepatitis E virus, Human immunodeficiency virus (HIV), Influenza virus, Lassa virus, Crimean-Congo hemorrhagic fever virus, Hantaan virus, Ebola virus, Marburg virus, Measles virus, Mumps virus, Parainfluenza virus, Respiratory syncytial virus, Rabies virus, Hepatitis D, Rotavirus, Orbivirus, Coltivirus, and Banna virus.

In certain embodiments, the pathogen comprises one or more of the following: *Acetobacter aurantius, Acinetobacter baumannii, Actinomyces israelii, Agrobacterium radiobacter, Agrobacterium tumefaciens, Anaplasma, Anaplasma phagocytophilum, Azorhizobium caulinodans, Azotobacter vinelandii*, viridans streptococci, *Bacillus, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, "Bacillus Thuringiensis", Bacteroides, Bacteroides fragilis, Bacteroides gingivalis, Bacteroides melaninogenicus* (now known as *Prevotella melaninogenica*), *Bartonella, Bartonella henselae, Bartonella quintana, Bordetella, Bordetella bronchiseptica, Bordetella pertussis, Borrelia burgdorferi, Brucella, Brucella abortus, Brucella melitensis, Brucella suis, Burkholderia, Burkholderia mallei, Burkholderia pseudomallei, Burkholderia cepacia, Calymmatobacterium granulomatis, Campylobacter, Campylobacter coli, Campylobacter fetus, Campylobacter jejuni, Campylobacter pylori, Chlamydia, Chlamydia trachomatis, Chlamydophila, Chlamydophila pneumoniae* (previously called *Chlamydia pneumoniae*), *Chlamydophila psittaci* (previously called *Chlamydia psittaci*), *Clostridium, Clostridium botulinum, Clostridium difficile, Clostridium perfringens* (previously called *Clostridium welchii*), *Clostridium tetani*, Coronavirus (e.g., SARS-COV-2, previously called 2019-nCoV), *Corynebacterium, Corynebacterium diphtheriae, Corynebacterium fusiforme, Coxiella burnetii, Ehrlichia chaffeensis, Enterobacter cloacae, Enterococcus, Enterococcus avium, Enterococcus durans, Enterococcus faecalis, Enterococcus faecium, Enterococcus gallinarum, Enterococcus maloratus, Escherichia coli, Francisella tularensis, Fusobacterium nucleatum, Gardnerella vaginalis, Haemophilus, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma, Mycoplasma fermentans, Mycoplasma genitalium, Mycoplasma hominis, Mycoplasma penetrans, Mycoplasma pneumoniae, Mycoplasma mexican, Neisseria, Neisseria gonorrhoeae, Neisseria meningitidis, Pasteurella, Pasteurella multocida, Pasteurella tularensis, Peptostreptococcus, Porphyromonas gingivalis, Prevotella melaninogenica* (previously called *Bacteroides melaninogenicus*), *Pseudomonas aeruginosa, Rhizobium radiobacter, Rickettsia, Rickettsia prowazekii, Rickettsia psittaci, Rickettsia quintana, Rickettsia rickettsii, Rickettsia trachomas, Rochalimaea, Rochalimaea henselae, Rochalimaea quintana, Rothia dentocariosa, Salmonella, Salmonella enteritidis, Salmonella typhi, Salmonella typhimurium, Serratia marcescens, Shigella dysenteriae, Spirillum volutans, Staphylococcus, Staphylococcus aureus, Staphylococcus epidermidis, Stenotrophomonas maltophilia, Streptococcus, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema, Treponema pallidum, Treponema denticola, Thiobacillus,*

*Vibrio, Vibrio cholerae, Vibrio comma, Vibrio parahaemolyticus, Vibrio vulnificus, Wolbachia, Yersinia, Yersinia enterocolitica, Yersinia pestis*, and *Yersinia pseudotuberculosis*.

In certain embodiments, the pathogen comprises one or more of the following: *Candida, Candida albicans, Aspergillus, Aspergillus fumigatus, Aspergillus flavus, Aspergillus clavatus, Cryptococcus, Cryptococcus neoformans, Cryptococcus laurentii, Cryptococcus albidus, Cryptococcus gattii, Histoplasma, Histoplasma capsulatum, Pneumocystis, Pneumocystis jirovecii, Pneumocystis carinii, Stachybotrys*, and *Stachybotrys chartarum*.

In certain embodiments, the one or more monoclonal and/or polyclonal antibodies comprises a member selected from the group consisting of the following: an anti-inflammatory (e.g., infliximab, adalimumab, basiliximab, daclizumab, or omalizumab); an anti-cancer (e.g., gemtuzumab, alemtuzumab, rituximab, trastuzumab, nimotuzumab, cetuximab, or bevacizumab & ranibizumab); an anti-cancer and anti-viral (e.g., bavituximab); palivizumab; and abciximab.

In certain embodiments, where the method is a method for administering a monoclonal and/or polyclonal antibody treatment via a rapid infusion (e.g., via a low flow rapid infuser) is performed for the treatment of COVID-19, caused by the virus SARS-CoV-2, the one or more monoclonal and/or polyclonal antibodies comprises one or more members selected from the group consisting of bamlanivimab (aka LY-CoV555, Eli Lilly); bamlanivimab+etesevimab antibody cocktail (aka LY-CoV555 (bamlanivimab)+JS016 (etesevimab) antibody cocktail, Eli Lilly); casirivimab and imdevimab antibody cocktail (aka REGN-COV2 aka REGEN-COV™ aka REGN10933+REGN10987, aka Ronapreve, Regeneron, Roche); gimsilumab (Roivant Sciences); tocilizumab (aka Actemra, Genentech); B38, H4, B5 and/or H2 Capital Medical University, Beijing; COVI-GUARD™ (STI-1499) and/or COVI-AMG™ (STI-2020) (Sorrento Therapeutics); regdanvimab aka Regkirona (Celltrion); sotrovimab (aka VIR-7831 aka Xevudy) and/or VIR-7832, Vir Biotechnology); and tixagevimab and cilgavimab antibody cocktail (aka Evusheld, AstraZeneca).

In certain embodiments, the method is performed for the treatment of a neurological disease or condition {e.g., Alzheimer's disease (AD), Parkinson's disease (PD); Duchene's muscular dystrophy (DMD); multiple sclerosis (MS); myasthenia gravis; migraine; migraine and cluster headache; neuromyelitis optica spectrum disorder (NMOSD); idiopathic inflammatory myopathies (IIM); immune-related peripheral neuropathies (multifocal motor neuropathy (MMN), anti-myelin associate glycoprotein (anti-MAG) neuropathy, chronic inflammatory demyelinating polyneuropathy (CIDP)); or a neurooncological condition (e.g., malignant glioma or recurrent glioblastoma)} [e.g., wherein the one or more monoclonal antibodies comprises one or more members selected from the group consisting of aducanumab (Biogen Inc.), gantenerumab (Chugai Pharmaceutical Co., Ltd., Hoffmann-La Roche), donanemab (Eli Lilly and Company), BAN2401 (Eisai Co., Ltd. and Biogen Inc.), gosuranemab (Biogen Inc., Bristol-Myers Squibb), zagotenemab (Eli Lilly and Company), tilavonemab (AbbVie, C2N Diagnostics, LLC), semorinemab (AC Immune SA, Genentech, Hoffmann-La Roche), cinpanemab (Biogen, Neurimmune), MEDI1341 (AstraZeneca, Takeda Pharmaceutical Company), domagrozumab (Pfizer Inc.), natalizumab (humanized Ab directed against α4 β1 integrin) (Biogen Inc.), alemtuzumab (Sanofi), ocrelizumab (Genentech USA, Inc.), ofatumumab (Novartis Pharmaceuticals Corporation), inebilizumab (Horizon Therapeutics plc), erenumab (Amgen Inc.), fremanezumab (Teva Pharmaceuticals USA, Inc.), eptinezumab (Lundbeck), galcanezumab (Lilly USA, LLC), rituximab (Amgen Inc.), eculizumab (Alexion Pharmaceuticals, Inc.), tocilizumab (Genentech, Inc.), satralizumab (Genentech USA, Inc.), ravulizumab (Alexion Pharmaceuticals, Inc.), aquaporumab, infliximab (Amgen Inc.), rozanolixizumab, nipocalimab (Johnson & Johnson Inc.), batoclimab (Harbour BioMed), efgartigimod (Argenx), bevacizumab (Pfizer Inc.), and rilotumumab (Amgen, Inc.).

In certain embodiments, the monoclonal antibody is an anti-inflammatory (e.g., infliximab, adalimumab, basiliximab, daclizumab, or omalizumab).

In certain embodiments, the monoclonal antibody is an anti-cancer (e.g., gemtuzumab, alemtuzumab, rituximab, trastuzumab, nimotuzumab, cetuximab, or bevacizumab & ranibizumab. In certain embodiments, the monoclonal antibody is an anti-cancer and anti-viral (e.g., bavituximab).

In certain embodiments, the monoclonal antibody is palivizumab or abciximab.

In certain embodiments, the one or more monoclonal antibodies comprises one or more members selected from the group consisting of: pembrolizumab (Keytruda), manufactured by Merck for treatment of cancer; nivolumab (Opdivo), manufactured by Bristol Myers Squibb, for various forms of cancer; bevacizumab (Avastin), manufactured by Roche, for colorectal, lung, glioblastoma, kidney, cervical, and/or ovarian cancer; ocrelizumab (Ocrevus), manufactured by Roche, for relapsing or primary progressive multiple sclerosis; rituximab (Rituxan), manufactured by Roche, Pharmstandard, for various autoimmune diseases and cancers; daratumumab (Darzalex), manufactured by Janssen (Johnson & Johnson), for multiple myeloma; pertuzumab (Perjeta), manufactured by Roche, for HER2-positive breast cancer; trastuzumab (Herceptin), manufactured by Genentech (Roche), for breast, stomach, and esophageal cancer; infliximab (Remicade), manufactured by Janssen (Johnson & Johnson), for Crohn's disease, ulcerative colitis, rheumatoid arthritis, ankylosing spondylitis, psoriatic arthritis, and plaque psoriasis; tocilizumab (Actemra/RoActemra), manufactured by Roche, for rheumatoid arthritis, forms of juvenile idiopathic arthritis and giant cell arteritis as well as CAR T cell-induced severe or life-threatening cytokine release syndrome; atezolizumab (Tecentriq), manufactured by Roche, for urothelial carcinoma, non-small cell lung cancer, and triple-negative breast cancer; tositumomab-I131 (Bexxar), manufactured by GSK, for non-Hodgkin lymphoma; olaratumab (Lartruvo), manufactured by Eli Lilly, for soft tissue sarcoma; MabThera, rituximab (Rituxan), manufactured by Biogen/Genentech, for non-Hodgkin lymphoma; basiliximab (Simulect), manufactured by Novartis, for prevention of kidney transplant rejection; ibritumomab tiuxetan (Zevalin), manufactured by Spectrum, for non-Hodgkin lymphoma; cetuximab (Erbitux), manufactured by Bristol Meyers Squibb, Eli Lilly, and Merck, for colorectal cancer; natalizumab (Tysabri), manufactured by Biogen/Elan, for multiple sclerosis; panitumumab (Vectibix), manufactured by Amgen, for colorectal cancer; ranibizumab (Lucentix), manufactured by Genentech/Novartis, for macular degeneration; eculizumab (Soliris), manufactured by Alexion, for paroxysmal nocturnal hemoglobinuria; ofatumumab (Arzerra), manufactured by Novartis, for chronic lymphocytic leukemia; belimumab (Benlysta), manufactured by Human Genome Sciences, for systemic lupus erythematosus; ipilimumab (Yervoy), manufactured by Bristol Meyers Squibb, for metastatic melanoma; pertuzumab (Perjeta), manufactured by Genentech, for breast cancer; raxibacumab, manufactured by Human Genome Sciences, for anthrax infection; obinutuzumab (Gazyva, Gazyvaro), manufactured by Genentech, for chronic lymphocytic leukemia; siltuximab (Sylvant), manufactured by Janssen Biotech, for Castelman disease; ramucirumab (Cyramza), manufactured by Eli Lilly, for gastric cancer; vedolizumab (Entyvio), manufactured by Takeda, for ulcerative colitis, Crohn's disease; alemtuzumab (Lemtrada, MabCampath, Campath-1H), manufactured by Genzyme, for multiple sclerosis and chronic myeloid leukemia, necitumumab (Portrazza), manufactured by Eli Lilly, for non-small cell lung cancer; dinutuximab (Qarziba, Unituxin), manufactured by United Therapeutics, for neuroblastoma; elotuzumab (Empliciti), manufactured by Bristol Meyers Squibb, for multiple myeloma; reslizumab (Cinqaero, Cinqair), manufactured by Teva, for asthma; bezlotoxumab (Zinplava), manufactured by Merck Sharp Dohme, for prevention of *Clostridium difficile* infection recurrence; obiltoxaximab (Anthim), for prevention of inhalational anthrax; avelumab (Bavencio), manufactured by Merck, for Merkel cell carcinoma; and durvalumab (Imfinzi), manufactured by AstraZeneca, for bladder cancer.

In another aspect, the invention is directed to a method for administering a monoclonal and/or polyclonal antibody treatment via a rapid infusion device (e.g., for the treatment of a disease caused by a pathogen, e.g., for the treatment of COVID-19, caused by the virus SARS-CoV-2), the method comprising: administering by intravenous infusion a volume of solution (e.g., an aqueous sodium chloride solution) comprising one or more (e.g., a cocktail of) monoclonal and/or polyclonal antibodies to a patient using a rapid infusion device, wherein the rapid infusion device comprises a pump (e.g., a roller pump or centrifugal pump, e.g., a centrifugal pump has a motor that supplies rotational energy, and the pump transports fluid by converting rotational kinetic energy to the hydrodynamic energy of the fluid flow) and a tubing line or lines, wherein the tubing line or lines fluidly connect directly or indirectly (i) an intravenous (IV) bag or other receptacle containing the volume of solution to the pump and (ii) the pump to the patient, for intravenous delivery of the volume of solution to the patient, wherein one, two, or all three of (a), (b), and (c), as follows, applies: (a) the pump administers the volume of solution to the patient substantially faster than by gravity alone, at a flow rate ranging from at least 5.17 mL/min 6.5 mL/min to at least 300 mL/min; (b) the pump administers the volume of solution at a dosing rate ranging from at least 35 mg/min to at least 400 mg/min of the one or more monoclonal and/or polyclonal antibodies and/or combinations thereof and/or at a total [total mg mAb(s) and/or pAb(s) per mL IV solution, e.g., aqueous solution, e.g., saline solution] concentration ranging from at most 20 mg/mL to at most 2.0 mg/mL; and (c) administration of the volume of solution to the patient is completed in a range of no more than 40 minutes to no more than 3 minutes.

In certain embodiments, the rapid infusion device operator may establish an initial, lower flow rate, then increase to a safe, higher flow rate if no serious IRRs are observed in the patient. The lower initial flow rate(s) may be in the range of at most 300 mL/min to at most 6.5 mL/min or in some embodiments, about 5.17 mL/min (for example, 5.0 mL/min).

In certain embodiments, the method comprises using flow rates determined in units of mg drug per kg patient weight per minute (mg/kg/min), where the prescribed dosage varies depending on the weight of the patient.

In certain embodiments, the method comprises using the rapid infusion device comprising a flow control valve or other feature that limits flow of fluid to the patient to no greater than a predetermined maximum flow rate.

In certain embodiments, method comprises using the rapid infusion device to deliver the volume of solution to the patient at a rate that approximates a predetermined fixed rate within the range of 1% to 30% of the predetermined fixed rate to avoid noncompliance with a prescribed solution delivery rate.

In certain embodiments, the method comprises using the rapid infusion device to deliver the volume of solution to the patient at a rate that approximates a predetermined fixed rate within the range of 1% to 30% of the predetermined fixed rate to avoid noncompliance with a prescribed solution delivery rate, wherein the rapid infusion device is designed for operation at a single approximate rate.

In certain embodiments, the method comprises using the rapid infusion device to permit a lower initial flow rate then a faster controlled flow rate, permitting but not requiring a higher flow rate after no serious IRRs are observed in the patient at the lower initial flow rate.

In certain embodiments, the method comprises using a disposable infusion set for connection to the rapid infusion device, e.g., wherein the disposable infusion set comprises one or more members of the group consisting of: a needle (e.g., straight steel needle), one or more lengths of tubing, an infusion bag, and an adhesive support (e.g., to avoid dislodging of the needle).

In certain embodiments, the method comprises using the rapid infusion device comprising a heater and/or an air venting mechanism, wherein the rapid infusion device does not comprise dripping chambers or a drip pan as used in drip I.V. infusers.

In certain embodiments, the method comprises the rapid infusion device comprising a filter for filtering out particles from the volume of solution prior to (upstream of) delivery of the filtered solution to the patient.

In certain embodiments, the method comprises using the filter that has a mesh size suitable to catch particles, wherein the filter mesh size ranges from at most 170 μm to at most 0.2 μm.

In certain embodiments, the method comprises using the rapid infusion device in a portable and/or single use manner.

In certain embodiments, the method comprises using the rapid infusion device in portable and/or single use manner, wherein the rapid infusion device has a total weight ranging from at most 5 lbs to at most 2 lbs.

In certain embodiments, the method comprises using the rapid infusion device comprising a pressure infusion bag (e.g., IV bag inserted into a cuff with an inflatable bladder, e.g., inflated at 300 mmHg, putting pressure on the contents of the IV bag.

In certain embodiments, the method comprises using the pressure infusion bag device comprising a flow control valve to limit flow to a prescribed maximum.

In certain embodiments, the method comprises using the rapid infusion device comprising an elastomeric pump, wherein the pump comprises the receptacle containing the volume of solution, and wherein the tubing line or lines fluidly connect directly or indirectly the pump (and, therefore, the receptacle containing the volume of solution) to the patient, for intravenous delivery of the volume of solution to the patient.

In certain embodiments, the method comprises using the rapid infusion device that may include a disposable set with a sterile fluid path intended for single-use, with standard luer connectors for connection to a standard catheter and a pressure-regulating valve (PRV) at the input to protect the disposable set and the patient from unintended exposure to high pressure applied to the IV line, wherein the PRV may allow an increase of flow from a low level to a higher level by application of a pressure (e.g., up to 300 mmHg), but will prevent pressure higher than this from reaching the set or IV line distal to it.

In certain embodiments, the method is performed for the treatment of an organ and/or tissue transplant patient [e.g., wherein the one or more polyclonal and/or monoclonal antibodies comprises one or more members selected from the group consisting of Thymoglobulin® (anti-thymocyte globulin [rabbit]) (Sanofi), Atgam® (lymphocyte immune globulin, anti-thymocyte globulin [equine] sterile solution) (Pfizer), alemtuzumab (Sanofi), rituximab (Amgen Inc), alpha-1 antitrypsin, and a double antibody conjugate that is an anti-CD3 and anti-CD7 agent].

In certain embodiments, the rapid infuser device comprises a flow control value or other feature that limits flow of fluid to the patient to no greater than a predetermined maximum flow rate.

In certain embodiments, the rapid infuser device delivers the volume of solution to the patient at a rate that approximates a predetermined fixed rate (e.g., within 30%, or within 25%, or within 20%, or within 15%, or within 10%, or within 5%, or within 2%, or within 1% of the predetermined fixed rate) (e.g., wherein the rapid infuser device is designed for operation at a single approximate rate, e.g., to avoid noncompliance with a prescribed solution delivery rate). In certain embodiments, the rapid infuser device permits a lower initial flow rate then a faster controlled flow rate (e.g., permitting faster flow after no serious IRRs are observed in the patient at the lower initial flow rate).

In certain embodiments, the method comprises using a disposable infusion set for connection to the rapid infuser device, e.g., wherein the disposable infusion set comprises one or more members of the group consisting of: a needle (e.g., straight steel needle), one or more lengths of tubing, an infusion bag, and an adhesive support (e.g., to avoid dislodging of the needle).

In certain embodiments, the rapid infusion device comprises an elastomeric (e.g., ball) pump, wherein the pump comprises the receptacle containing the volume of solution, and wherein the tubing line or lines fluidly connect (e.g., directly or indirectly) the pump (and, therefore, the receptacle containing the volume of solution) to the patient, for intravenous delivery of the volume of solution to the patient.

In certain embodiments, the rapid infusion device comprises a heater and/or an air venting mechanism (e.g., wherein the rapid infuser device does not comprise dripping chambers or a drip pan as used in drip IV infusers). By contrast, drip infusers may cause air bubbles, particularly if the fluid is warmed, and drip infusers generally do not have any air venting mechanism. Air bubbles may cause stroke, among other serious problems. Furthermore, monoclonal antibodies (and/or polyclonal antibodies) can oxidize due to surface air contact—a rapid infuser with an air venting mechanism can mitigate this problem. Moreover, drip infusers may cause aggregation of monoclonal and/or polyclonal antibodies as the fluid contacts the drip chambers of the drip infuser, whereas, in various embodiments described herein, the rapid infuser does not have drip chambers, thereby avoiding the risk of aggregation due to the presence of drip chambers.

In certain embodiments, the rapid infusion device comprises a filter for filtering out particles (e.g., monoclonal antibody aggregates and/or polyclonal antibody aggregates) from the volume of solution prior to (upstream of) delivery of the filtered solution to the patient. In certain embodiments, the filter has a size small enough (e.g., a mesh tight enough) to catch the particles (e.g., monoclonal antibody aggregates and/or polyclonal antibody aggregates). In certain embodiments, the filter has a size below 170 microns (e.g., below 150 microns, e.g., below 125 microns, e.g., below 100 microns, e.g., below 75 microns, e.g., below 50 microns, e.g., below 40 microns, e.g., below 30 microns, e.g., below 20 microns, e.g., below 10 microns, e.g., below 8 microns, e.g., below 5 microns, e.g., below 4 microns).

In certain embodiments, the rapid infuser device is portable and/or is designed for a single use. For example, in certain embodiments, the rapid infuser device comprises a pressure infusion bag (e.g., IV bag inserted into a cuff with an inflatable bladder, e.g., inflated at 300 mmHg, putting pressure on the contents of the IV bag. In certain embodiments, the pressure infusion bag device comprises a flow control valve to limit flow to a prescribed maximum.

In another aspect, the invention is directed to a rapid infuser device for administering by intravenous infusion a volume of solution (e.g., a sodium chloride solution) comprising one or more (e.g., a cocktail of) monoclonal and/or polyclonal antibodies to a patient, the rapid infuser device comprising: a pump (e.g., a roller pump or centrifugal pump); and a tubing line or lines, wherein the tubing line or lines fluidly connect (e.g., directly or indirectly) (i) an intravenous (IV) bag or other receptacle containing the volume of solution to the pump and (ii) the pump to the patient, and wherein the pump is configured such that one, two, or all three of (a), (b), and (c), as follows, applies: (a) the pump is capable of administering the volume of solution to the patient at a flow rate substantially faster than by gravity alone (e.g., at a flow rate of at least 10 mL/min, or at least 15 mL/min, or at least 20 mL/min, or at least 25 mL/min, or at least 30 mL/min, or at least 35 mL/min, or at least 40 mL/min, or at least 45 mL/min, or at least 50 mL/min); (b) the pump is capable of administering the volume of solution at a dosing rate of at least 35 mg of the one or more monoclonal and/or polyclonal antibodies (e.g., combined) per minute (e.g., at least 40 mg/min, at least 50 mg/min, at least 60 mg/min, at least 70 mg/min, at least 80 mg/min, at least 90 mg/min, at least 100 mg/min, at least 125 mg/min, at least 150 mg/min, at least 175 mg/min, at least 200 mg/min, at least 225 mg/min, at least 250 mg/min, at least 275 mg/min, at least 300 mg/min, at least 325 mg/min, at least 350 mg/min, at least 375 mg/min, or at least 400 mg/min of the one or more monoclonal and/or polyclonal antibodies (e.g., combined)) and/or at a total [mAb(s) and/or pAb(s)] concentration of less than or equal to 20 mg/mL, less than or equal to 15 mg/mL, less than or equal to 10 mg/mL, less than or equal to 9 mg/mL, less than or equal to 8.5 mg/mL, less than or equal to 8 mg/mL, less than or equal to 7 mg/mL, less than or equal to 6 mg/mL, less than or equal to 5 mg/mL, less than or equal to 4.5 mg/mL, less than or equal to 4 mg/mL, less than or equal to 3.5 mg/mL, less than or equal to 3.0 mg/mL, less than or equal to 2.5 mg/mL, or less than or equal to 2.0 mg/mL [total mg mAb(s) and/or pAb(s) per mL IV solution, e.g., aqueous solution, e.g., saline solution]; and (c) the pump is capable of administering the volume of the solution in no more than 30 minutes (e.g., no more than 25 minutes, e.g., no more than 20 minutes, e.g., no more than 15 minutes, e.g., no more than 10 minutes, e.g., no more than 7 minutes, e.g., no more than 5 minutes, e.g., no more than 4 minutes, e.g., no more than 3 minutes).

In certain embodiments, the device comprises a flow control valve or other feature that limits flow of fluid to the patient to no greater than a predetermined maximum flow rate.

In certain embodiments, the rapid infuser device is capable of delivering the volume of solution to the patient at a rate that approximates a predetermined fixed rate (e.g., within 30%, or within 25%, or within 20%, or within 15%, or within 10%, or within 5%, or within 2%, or within 1% of the predetermined fixed rate) (e.g., wherein the rapid infuser device is designed for operation at a single approximate rate, e.g., to avoid noncompliance with a prescribed solution delivery rate).

In certain embodiments, the device comprises a disposable infusion set, e.g., wherein the disposable infusion set comprises one or more members of the group consisting of: a needle (e.g., straight steel needle), one or more lengths of tubing, and an adhesive support (e.g., to avoid dislodging of the needle).

In certain embodiments, the rapid infuser device comprises an elastomeric (e.g., ball) pump, wherein the pump comprises the receptacle containing the volume of solution, and wherein the tubing line or lines fluidly connect (e.g., directly or indirectly) the pump (and, therefore, the receptacle containing the volume of solution) to the patient, for intravenous delivery of the volume of solution to the patient.

In certain embodiments, the rapid infuser device comprises a heater and/or an air venting mechanism (e.g., wherein the rapid infuser device does not comprise dripping chambers or a drip pan as used in drip I.V. infusers).

In certain embodiments, the rapid infuser device comprises a filter for filtering out particles (e.g., monoclonal antibody aggregates and/or polyclonal antibody aggregates) from the volume of solution prior to (upstream of) delivery of the filtered solution to the patient. For example, in certain embodiments, the filter has a size small enough (e.g., a mesh tight enough) to catch the particles (e.g., monoclonal antibody aggregates and/or polyclonal antibody aggregates) (e.g., wherein the filter has a size below 170 microns, e.g., below 150 microns, e.g., below 125 microns, e.g., below 100 microns, e.g., below 75 microns, e.g., below 50 microns, e.g., below 40 microns, e.g., below 30 microns, e.g., below 20 microns, e.g., below 10 microns, e.g., below 8 microns, e.g., below 5 microns, e.g., below 4 microns, e.g., below 2 microns, e.g., below 1 micron, e.g., below 0.7 micron, e.g., below 0.5 micron, e.g., below 0.3 micron, e.g., about 0.2 µm).

In certain embodiments, the rapid infuser device is portable and/or is designed for a single use (e.g., wherein the rapid infuser has a total weight (e.g., including heater, battery, and disposable) less than 5 lbs., e.g., less than 3 lbs., e.g., less than 2 lbs.).

In another aspect, the invention is directed to a kit for administering a monoclonal and/or polyclonal antibody treatment via a rapid infuser device (e.g., for the treatment of a disease, e.g., a disease caused by a pathogen, e.g., for the treatment of COVID-19, caused by the virus SARS-CoV-2) according any of the methods described herein.

FIG. 1 shows an example of a rapid infusion system 100, in accordance with an illustrative embodiment of the invention. The rapid infusion system 100 includes an intravenous (IV) bag or other receptacle 110 containing a volume of drug solution to be administered to the patient. Elements of the rapid infusion system 100 are connected by tubing lines (e.g., a disposable set designed for one-time use). The drug solution is drawn from the IV bag or other receptacle 110 with pump 120 (e.g., a roller pump or centrifugal pump).

Element 130 is a heater (which in some embodiments, may be optional) or other temperature control device. LY-CoV555 appears to be stable at room temperature for up to 7 hours; thus no special temperature controls may be needed during infusion.[57] Additionally or alternatively, element 130 may optionally include one or more of a rate control device (e.g., a pressure-regulating valve 135, a pressure responsive valve 135, or the like), one or more sensors 140, and/or feedback circuitry 145. Heating element 130 may alternatively or additionally include an air venting mechanism 150.

In certain embodiments, element 130 includes (or is) a filter 155 for filtering out particles (e.g., monoclonal antibody aggregates and/or polyclonal antibody aggregates) from the volume of solution prior to (upstream of) delivery of the filtered solution to the patient. In certain embodiments, the filter 155 has a size small enough (e.g., a mesh tight enough) to catch the particles (e.g., monoclonal antibody aggregates and/or polyclonal antibody aggregates).

In certain embodiments, the filter 155 has a size below 170 microns (e.g., below 150 microns, e.g., below 125 microns, e.g., below 100 microns, e.g., below 75 microns, e.g., below 50 microns, e.g., below 40 microns, e.g., below 30 microns, e.g., below 20 microns, e.g., below 10 microns, e.g., below 8 microns, e.g., below 5 microns, e.g., below 4 microns, e.g., below 2 microns, e.g., below 1 micron, e.g., below 0.7 micron, e.g., below 0.5 micron, e.g., below 0.3 micron, e.g., about 0.2 µm). A standard filter size for blood administration is generally 170-260 microns, which is designed to trap fragments of cells, clots, or particulate matter that may develop as a result of blood product storage. However, particulate matter from antibody solutions is smaller (e.g., and/or the solution viscosity is less than that of blood), so a filter that traps smaller particles may be advantageously used for certain embodiments described herein.

The rapid infusion system 100 may include (e.g., as part or all of element 130, or as a separate element) an alarm 160 that identifies air or any other blockage in the line. The rapid infusion system 100 may include (e.g., as part or all of element 130, or as a separate element) an alarm 160 that identifies when a flow rate is above or below a prescribed rate. In certain alternative embodiments, element 130 is positioned between element 110 (IV bag or other receptacle) and the pump 120. In certain embodiments, element 130 (i.e., the heating element) is positioned downstream of pump 120.

Element 130 may have one or more components, any one or more of which may be in a different position with respect to other elements of the system than pictured in FIG. 1 (e.g., one or more elements of 130, e.g., a filter, may be positioned between IV bag 110 and pump 120, ahead of the pump, or may be part of the intravenous (IV) bag or other receptacle 110).

Figure 2:
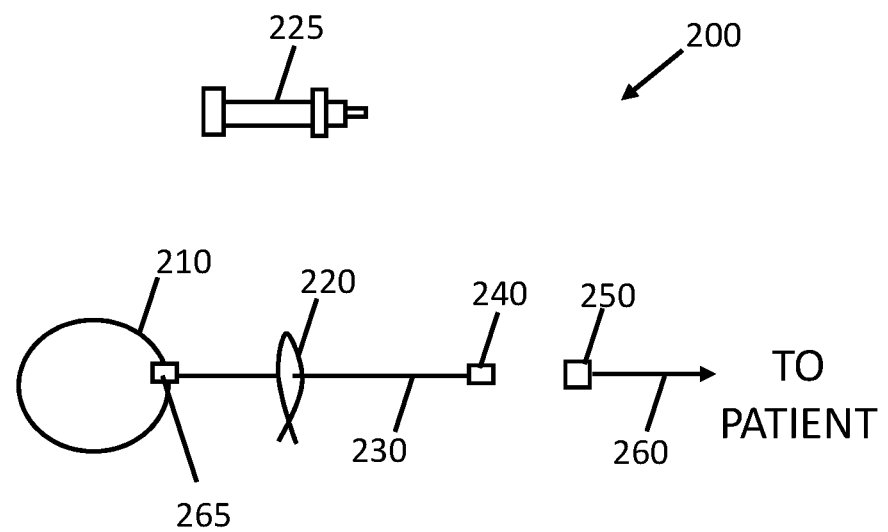
FIG. 2 shows another system and device for administering a monoclonal and/or polyclonal antibody solution via rapid infusion, according to an illustrative embodiment.

FIG. 2 shows an example of a rapid infusion system 200, in accordance with an illustrative embodiment of the present disclosure. The rapid infusion system 200 shown in FIG. 2 includes an elastomeric medicine ball 210 (also known as a "homeball," "ball pump," and/or "grenade pump"). The elastomeric medicine ball 210 may be used for drug delivery in place of the reservoir 110, pump 120, heating element 130, and/or other components illustrated in FIG. 1 and described above. In some embodiments, the system 200 may be used for administering rapid infusion to patients in their own homes, for example. Elastomeric medicine balls 210 are considered pumps, but they do not typically operate with electricity. Elastomeric pumps use pressure created by an elastomeric layer molded into the inside of the medicine ball 210 to infuse its fluid contents into a patient. In certain embodiments, the system 200 includes a pump line 230 that is configured to connect to a patient IV line 260 (that may be already installed (i.e., pre-installed) in the patient, or alternatively may be installed at the time of treatment). Prior to connection with the pump line 230, the patient IV line 260 may be flushed with saline solution (for example, via syringe 225) to ensure no clogs in the system 200, and then subsequently sanitized with alcohol wipes, especially at device access port (or hub) 250 (where contaminants could potentially enter the patient IV line 260). A pump line cap 240 can then be removed and the pump line 230 can be fluidly connected (for example, by inserting and twisting) into hub 250. When the patient is ready for drug delivery, clamp 220 can be removed from the pump line 230, and the drug will begin flowing into the patient via the patient IV line 260.

The elastomeric medicine ball 210, according to certain embodiments of the present disclosure, may be pre-filled with drug product (i.e., drug solution) and may be pre-pressurized. Once the clamp 220 is removed, the pressure within the elastomeric medicine ball 210 gradually forces the drug solution out of the elastomeric medicine ball 210, through the pump line 230 and patient IV line 260, and into the patient. In certain embodiments, the delivery process for a single administration can take as long as 90 minutes, but is preferably a shorter time period, for example, administration is completed in no more than 30 minutes (e.g., no more than 25 minutes, e.g., no more than 20 minutes, e.g., no more than 15 minutes, e.g., no more than 10 minutes, e.g., no more than 5 minutes). Elastomer balls generally have a flow restrictor 265 to control the accuracy of the rate of flow. The flow restrictor 265 may be, for example, a steel cannula or a glass capillary molded into system tubing or located inside the elastomeric reservoir. Standard elastomer balls generally provide a flow rate of up to about 250 mL/hr (about 4.17 mL/min). For the methods described herein, elastomer balls may be engineered to permit higher flow rate, for example, flow rate substantially faster than IV flow by gravity alone (e.g., the elastomer ball system provides a flow rate of at least 10 mL/min, or at least 15 mL/min, or at least 20 mL/min, or at least 25 mL/min, or at least 30 mL/min, or at least 35 mL/min, or at least 40 mL/min, or at least 45 mL/min, or at least 50 mL/min). Total drug delivery volumes per elastomeric medicine ball 210 may range up to about 500 mL (e.g., the total volume may be about 50 mL, about 100 mL, about 150 mL, about 250 mL, about 350 mL, about 450 mL, about 500 mL, or within ±50 mL ranges of each of these figures).

In some embodiments, where higher diffusion rates are required, a patient IV line 260 can be installed in each arm (or, alternatively, in one or more other locations of the body), each patient IV line 260 connecting to a separate elastomeric medicine ball 210. In certain embodiments, because the elastomeric medicine ball 210 is calibrated according to the inherent back pressure or resistance in the pump line 230, patient IV line 260, and patient himself/herself, the elastomeric medicine ball 210 generally would not be used in connection with, for example, the fluid heater 130 (shown in FIG. 1). Accordingly, where the contents must be kept refrigerated before use, each elastomeric medicine ball 210 should be removed from the refrigerator with enough time to warm up to room temperature (for example, 10-30 minutes, or about 10-20 minutes) prior to use. However, care should be taken not to expose each elastomeric medicine ball 210 to room temperature for a prolonged period of time, to avoid spoiling and/or breakdown of the drug product.

Still referring to FIG. 2, the system 200 may include one or more elastomeric medicine balls 210 that use only the pressure within each elastomeric medicine ball 210, and not gravity or a separate pump, for drug delivery. As such, patients have the ability to move around and carry the one or more elastomeric medicine balls 210 with them (for example, in a pocket or pockets, etc.) as the drug is flowing. In certain embodiments, once the treatment is complete, each elastomeric medicine ball 210 will be fully deflated, and the pump line 230 can be removed from the device access port 250 (or hub 250). The elastomeric medicine ball 210, pump line 230, clamp 220, and cap 240 can then be disposed of. In certain embodiments, post treatment flushing of the patient IV line 260 should be performed to ensure any drug solution still in the patient IV line at the end of treatment in pushed through the patient IV line 260 into the patient. In certain embodiments, final (i.e., post flushing) sterilization of the hub or device access port 250 should be performed, and the device access port should be capped after sterilization. In some embodiments, heparin may be administered before and/or after the final flushing to avoid clotting, depending on the patient needs. In some embodiments, the system 200 shown in FIG. 2 may also include a heating element in fluid communication with the drug IV line 230 (i.e., downstream of the ball pump 210) to more rapidly heat the infusate. The system 200 may also include an additional pump fluidly upstream of the heating element in order to overcome any addition flow restriction or pressure drop introduced by the heating element.

Figure 3:
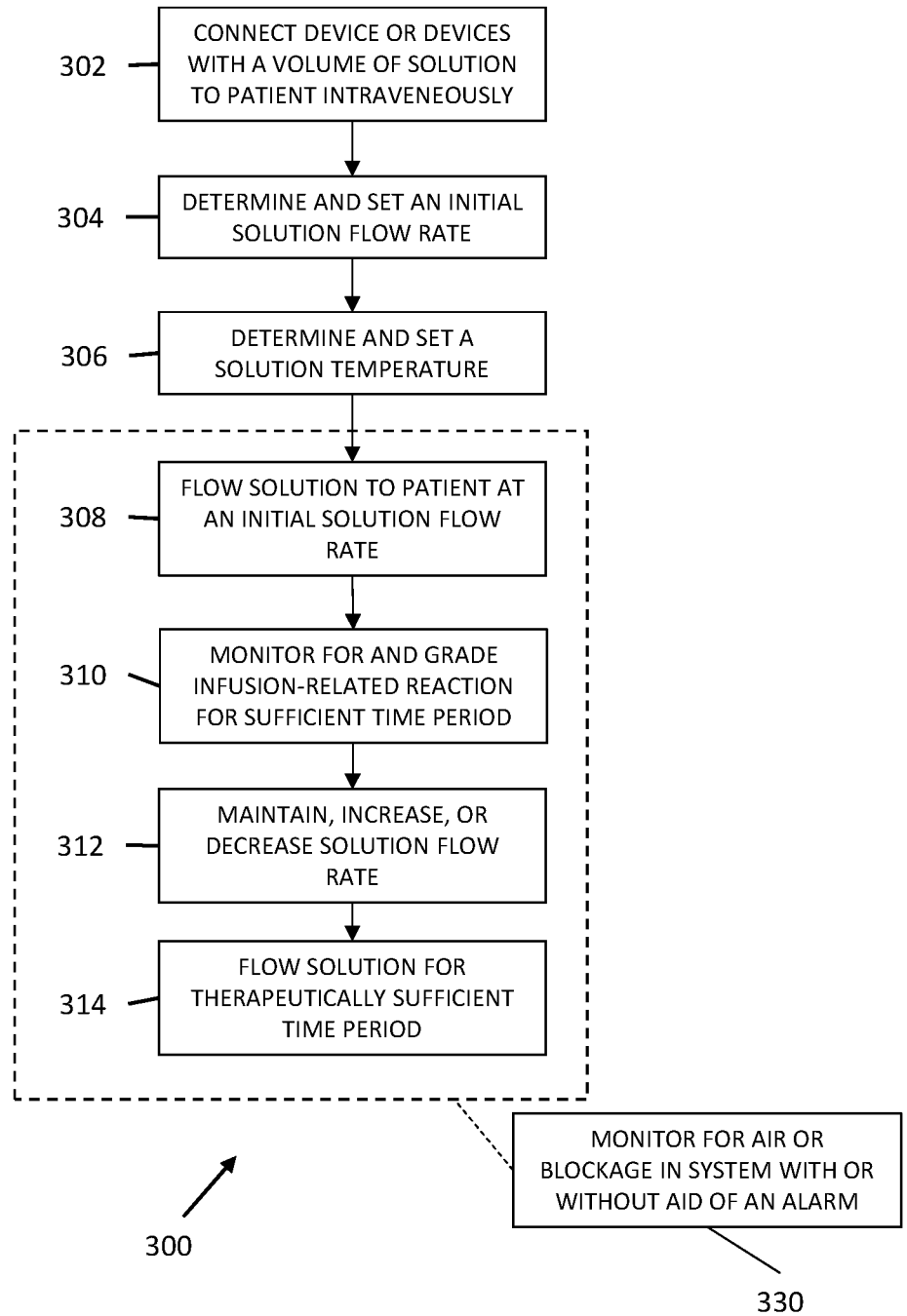
FIG. 3 shows a method of using devices for administering a monoclonal and/or polyclonal antibody solution via rapid infusion, according to an illustrative embodiment.

FIG. 3 illustrates a method 300 for systems 100 and/or 200, according to aspects of the present embodiments. Prior to step 302, the method 300 for system 200 may include using a syringe 225 and flushing the intravenously-attached system at port 250 with saline.

Still referring to FIG. 3, in step 304, a solution flow rate may be determined according to various embodiments of system 100 and may be controlled using a flow-controlling device 120. At step 304, an initial solution flow rate may be determined according to various embodiments of system 200 and may be controlled using a flow-controlling device 210. The initial solution flow rate may be 50 mg/hr, 100 mg/hr, or from about 25 mg/hr to about 75 mg/hr, or in other embodiments from about 75 mg/hr to about 125 mg/hr. The flow rate may then be increased in increments of about 25 mg/hr, 50 mg/hr, and/or 100 mg/hr, at time intervals of about 1 minute, 2 minutes, 5 minutes, 10 minutes, 15 minutes, 20, minutes, and/or 30 minutes, to a maximum flow rate of about 400 mg/hr, or from about 300 mg/hr to about 450 mg/hr, or from about 250 mg/hr to about 500 mg/hr, or from about 150 mg/hr to about 450 mg/hr.

Still referring to FIG. 3, in step 306, a solution temperature may be determined according to various embodiments of system 100 and a solution temperature may be set using an optional temperature-controlling device 130. In step 306, a solution temperature may be determined according to various embodiments of system 200 and a solution temperature may be set by equilibrating a solution to an ambient temperature or physiologically-relevant temperature.

Still referring to FIG. 3, in step 308, rapid infusion is started by flowing a solution at an initial flow rate determined by various embodiments of the invention. In step 310, the patient is monitored and graded for infusion-related reactions (IRR).

Still referring to FIG. 3, in step 312, a solution flow rate is maintained, increased, or decreased based on IRR grading and according to various embodiments of the present invention. In step 312, solution flow rate may be maintained for a patient presenting no IRR or presenting a minor IRR after an initial solution flow and being treated using an embodiment of system 100 or an embodiment of system 200. In step 312, solution flow rate may be increased for a patient presenting no IRR or presenting a minor IRR after an initial solution flow and being treated using an embodiment of system 100 or an embodiment of system 200. In step 312, solution flow rate may be increased for a patient presenting no IRR or presenting a minor IRR after an initial solution flow and being treated using an embodiment of system 100 or an embodiment of system 200.

Still referring to FIG. 3, in step 314 a solution may be continued to flow at a flow rate previously determined in method 300 for a time period sufficient for providing disease therapy. At step 330, the method 300 may include monitoring for air and/or blockage in the system (for example, with or without the air of alarm 160) during the entire period of time that solution is flowing (i.e., steps 308-314 in FIG. 3). In some embodiments, prior to step 302, a volume of therapeutic solution may be loaded into any device or devices (for example, 110, 210, 225) as needed according to aspects of the present disclosure.

In one embodiment, a solution temperature set-point is set at 37° C. (or from about 36° C. to about 38° C., or from about 30° C. to about 37° C., or from about 28° C. to about 37° C.), an initial flow rate of 50 mg/hr is maintained for a period of 15 minutes, and then after no infusion-related reactions (IRR) are observed, the flow rate is increased by 50 mg/hr every 10 minutes until a maximum flow rate of 350 mg/hr is reached. The maximum flow rate is then maintained for the duration of infusion. In another embodiment, an initial infusate flow rate of about 500 mg/hr is maintained for the entire infusion process until an infusate volume of about 250 ml has flowed into the patient after about 30 minutes. In other embodiments, average infusate flow rates higher than 500 mg/hr (for example, 750 mg/hr, or from about 600 mg/hr to about 850 mg/hr) are maintained such that the entire infusion process is complete within 15-25. Similarly, in some embodiments, a total infusate volume of less than 250 ml (for example 75-225 ml, or about 100 ml to about 200 ml) flows into the patient at a rate of about 500 mg/hr, again resulting in a total infusion time of less than 30 minutes (for example, from about 9 minutes to about 30 minutes, from about 9 minutes to about 27 minutes, from about 9 minutes to about 24 minutes, from about 12 minutes to about 24 minutes, and/or various subranges therebetween).

In some embodiments, the rapid infusion system is designed for simple operation at a single flow rate, or at a small number of flow rates (e.g., two, three, or four flow rates) (e.g., when operated for drug delivery, e.g., in a dedicated "drug delivery mode"), e.g., a flow rate prescribed specifically for delivery of a drug solution comprising a monoclonal antibody, e.g., for the treatment of COVID-19. This may be particularly helpful in situations for which simplified training is needed, e.g., during a pandemic when a large number of doses must be delivered in a short period of time and there is limited staff available to perform administration to the patients. As explained above, there may be a serious shortage of staff, and/or a serious shortage of available infusion sites that can accommodate COVID-19 patients without interfering with other infusion patients (e.g., patients who may have chronic conditions, e.g., patients who may be immunocompromised).

In certain embodiments, drug administration is further simplified by provision of a portable rapid infusion system with disposable tubing lines already attached, e.g., where the entire rapid infusion system, pump included, is designed for a single use. Further simplification may be possible by providing the IV bag (or other receptacle) pre-loaded with drug solution (e.g., pre-made drug solution) in the appropriate amount and at the appropriate concentration (e.g., all in a self-contained kit). Providing a pre-made solution may not be possible for certain drugs.

Publications mentioned herein are hereby incorporated by reference, in their entireties.

Constructive Exemplary Embodiments

Testing Stability, ADME, and $C_{max}$ of Rapidly Infused mAbs

It is possible to test the effect of rapid infusion (RI) of selected monoclonal antibodies (mAbs) of various concentrations on their stability, ADME characteristics, and $C_{max}$ when compared to the results achieved by subcutaneous administration and drip infusions, at various rates of infusion.

Stability mAbs become unstable when the higher-order structure is lost through unfolding. The consequences of unfolding include direct perturbation of the mAb's function, for example, in the promotion of aggregation.[58] (Aggregation is the assembly from initially native and folded proteins into high molecular weight species.)[59]

mAbs Aggregation is often irreversible, especially at later stages, and aggregates often contain high levels of proteins with a non-native conformation.[60-62] Aggregation may cause a stronger immunogenicity of protein therapeutics,[60, 63] which can lead to the loss of efficacy of the mAb and IgE-mediated immediate hypersensitivity and anaphylaxis.[64] In addition, unfolding reveals the hydrophobic residues that are mostly hidden in the native conformation, reducing solubility in hydrophilic buffer and increasing subsequent self-association and then aggregation.[65]

ADME

The ADME (Absorption, Distribution, Metabolism, and Elimination) properties provide a means to document the safety and efficacy of rapid infusion of mAbs.

Absorption (how much and how fast, often referred to as the absorbed fraction or bioavailability)

Distribution (where the drug is distributed, how fast and how extensively)

Metabolism (how fast, what mechanism/route, what metabolites are formed, and whether they are active or toxic)

Elimination (how fast, which route).[84]

CMAX

A pharmacokinetic measure used to determine drug dosing, $C_{max}$ is the highest concentration of a drug in the blood, cerebrospinal fluid, or target organ after a dose is given. It is measured by sampling the fluid or tissue and performing validated bioanalytical assays developed for the specific drug of interest.

Clinical Benefits of Rapid Infusion of mAbs

Subcutaneous Administration

Subcutaneous administration is considered subordinate to infusion. The FDA recommends intravenous infusion as the preferred administration route over subcutaneous administration[80] likely due to the slow absorption of mAbs during subcutaneous administration.[85] When mAbs are administered subcutaneously, they often present with slow absorption[85] and bioavailability that varies from 20-95%.[87]

Stability Enhancing Characteristics of RI:

mAbs can become unstable through agitation, oxidation, temperature, dilution in intravenous (IV) bags, and administration through IV-lines.[66] Stability may be enhanced through the use of an RI device to infuse mAbs in a manner that reduces these causes of instability. The RI device is a medical device that warms and pumps fluids that are intravenously administered to the patient, as discussed in this disclosure. A high-speed peristaltic pump enables accuracy in fluid delivery, with flow rates ranging from 2.5 to 1,000 ml/min. The flow rate can be automatically adjusted by the operator. The RI device includes features that can reduce agitation of mAbs that can occur in gravity fed IV lines and protect the patient from protein aggregation.

Fluid Dynamics

In general, mAbs do not disperse widely in tissues and remain heavily in the blood stream due to a low volume of distribution of 3-8 L at steady state.[86] Osmolality of the most concentrated recommended infusion of mAbs will be measured during the testing to ensure cells are not lysed or damaged due to osmotic pressure gradients. Although the viscosity of the mAbs solution is much less than that of blood—the dynamic viscosity (centipoise) of blood is 10 and that of water is 1—dynamic viscosity will be measured as part of the proposed testing.

Effect of Infusion Via an RI Device on Characteristics of mAbs Stability

Agitation

Agitation of the mAb can be caused in normal IV lines with gravity fed administration where drip chambers are used to gauge the flow rate. The drip chambers can cause agitation as the infusate forms droplets and falls to the bottom of the drip chamber. The RI device infusion set does not need a drip chamber to gauge flow rates as a software-controlled pump is used to administer the fluids. By eliminating the drip chamber in an RI device, agitation of the mAbs and infusate will be mitigated.

Air Interfaces

Because of the relative hydrophobicity of air compared to water, proteins may adsorb at the air-water interface, forming layers.[60] Significant volumes of air may be inherently present in IV infusion lines,[82] which the RI device completely eliminates. Air can be present within the IV line due to pre-existing air within the fluid bag, introduction of air during the bag spiking process, or incomplete priming efforts. A rupture of these protein absorption layers at air interfaces leads to the formation of protein aggregates in the solution, linked to surface tension forces at the interfaces that perturb the protein structure.[67]

Removing oxygen in the IV line suppresses aggregation due to the elimination of air interfaces. The RI device eliminates air as it is naturally outgassed from the solution during the warming process. As fluid is warmed to normothermic body temperature, any dissolved gases will come out of solution. By collecting and eliminating this air, the RI device potentially avoids excess protein aggregation from infusion in the body and potential aggregation that would otherwise have been formed within the body if the infusion were not pre-warmed to normothermic temperature prior to infusion.

Oxidation

The chemical reactions of oxidation may cause a reduction in binding affinity and mAb potency, and may also reduce the affinity for macrophages, specialized cells involved in the detection, phagocytosis and destruction of bacteria and other harmful organisms, or increase mAb clearance.[69,70] An increase in mAb clearance is undesirable as the mAb is not given sufficient time to have positive effects on the patient prior to being eliminated from the body. In addition, several studies have shown that these chemical instabilities can lead to conformational modifications and aggregation.[71] Removing dissolved oxygen in solution has been shown to suppress oxidation effects of mAbs.[68] The presence of dissolved oxygen assists in catalyzing oxidation reactions. By eliminating this air, the RI device potentially avoids excess protein aggregation from being infused in the body.

Temperature mAbs can be exposed to temperature variations during their processing, storage, transportation and infusion stages. High temperatures can perturb the native protein conformation sufficiently to promote aggregation, but aggregation begins at temperatures well below the equilibrium melting temperature (Tm) of the protein. Each protein has a specific Tm, which is the temperature where 50% of proteins are unfolded. This temperature is in most cases between 40° C. and 80° C. for mAbs. Heating and cooling rates are also important factors, as extreme rates seem to lead to instability.[72-74]

The RI device warms infusate to normal body temperature using controlled inductive heating. High temperatures are precisely controlled to ensure the device does not damage temperature sensitive infusates.

Concentration

Higher protein concentrations, as used in subcutaneous administration of mAbs and some drip infusions, seem to increase the viscosity of solutions, which may increase the aggregation potential of proteins by enhancing protein-protein interactions and self-association.[61,75] (However, the impact of high protein concentrations is complex; for example, some research found that high concentrations increased smaller particles concentrations while decreasing bigger ones,[76,60], whereas others[77] demonstrated an increase in aggregation rate with concentration.)

Testing the Effect of Rapid Infusion on the Stability of mAbs:

The effect of rapid infusion on mAb stability can be tested by comparing the results of infusing a mAb through a RI device to those achieved by slower infusion of the mAbs in various amounts of diluent.

Testing for Rituximab

Standard Infusion—The first infusion can be initiated at 50 mg/hr, with gradual increases up to max 400 mg/hr (total infusion time is 4.25 hours). Subsequent infusions can initiate at 100 mg/hr with less gradual increases up to max 400 mg/hr (total infusion time is 3.25 hours).[92] We will also test for a 90-minute infusion, which is considered appropriate for certain patients: NHL & CLL 90 Minute Infusion-|RITUXAN® (rituximab).[93]

mAbs will be diluted and infused using a RI warming device with controlled warming rates and out-gas elimination under various test conditions. After its completion, the exposed mAbs will be evaluated in first pass bench testing. Following first pass testing, second pass testing will be completed and analyzed prior to moving forward with clinical testing.

First Pass Bench Testing

Physiochemical stability testing methods will be used to characterize the stability of mAbs before and after their infusion via the RI device in comparison to that achieved using the FDA cleared instructions for use (IFUs) concerning flow rates, bag size (to evaluate low and high concentrations), and infusion time using drip infusion.

Stability Testing

Antibody stability may be tested for the three types of stability defined below: conformational stability, colloidal stability, and chemical stability.[81]

1. Conformational Stability

Under stressed conditions, such as high temperature, antibodies undergo a transition from the folded to unfolded state, thereby exposing hydrophobic patches that are usually buried in the native protein. Example techniques of choice for measuring unfolding temperatures and thermodynamic parameters during protein unfolding may be provided, for example, by Differential Scanning calorimetry (DSC) Services (https://www.creative-biolabs.com/Differential-scanning-calorimetry-DSC-Service.html). The melting temperature ($T_m$), at which the transition occurs is used as a surrogate parameter for the thermal stability of the antibody.

Aggregates tend to form due to the interaction between exposed hydrophobic regions. For aggregation analysis, analytical tools include analytical ultracentrifugation (AUC), size-exclusion chromatography (SEC), and dynamic light scattering (DLS). [e.g., See https://www.creative-biolabs.com/drug-discovery/therapeutics/sedimentation-velocity-analytical-ultracentrifugation-sv-auc-for-antibody-aggregation-analysis.htm, https://www.creative-biolabs.com/drug-discovery/therapeutics/size-exclusion-chromatography-sec-for-antibody-aggregation-analysis.htm, and https://www.creative-biolabs.com/drug-discovery/therapeutics/dynamic-light-scattering-dls.htm].

2. Colloidal Stability

Colloidal stability is the stability of protein with the native structure in solution to avoid aggregation, precipitation, or phase separations. Computational methods can calculate the theoretical pI (isoelectric point or pH at which the protein is electrically neutral), which can be used to estimate the stable pH range of potential formulations. To measure subsequent aggregation of phase separation, dynamic light scattering (DLS) can be used to measure the $K_D$, which indicates the interaction between molecules. Another manifestation of colloidal instability is the phase separation, which can be quantified using polyethylene glycol (PEG).

3. Chemical Stability

Chemical stability is the stability of amino acids and the covalent bonds between them and between different protein domains. Chemical instability can be caused by chemical modification of mAb amino acids, including C-terminal processing of lysine residues, N-terminal pyroglutamate formation, C, and oxidation. [e.g., See https://www.creative-biolabs.com/drug-discovery/therapeutics/c-terminal-lysine-variant-analysis.htm, https://www.creative-biolabs.com/drug-discovery/therapeutics/n-terminal-cyclization-analysis.htm, and https://www.creative-biolabs.com/drug-discovery/therapeutics/oxidation-analysis.htm.] These modifications can be characterized using various techniques, including chromatography-based techniques, charge-based techniques, and mass spectrometry (MS)-based techniques. The chemical stability can be predicted by analysis of these chemically unstable regions.

Testing for ADME (Absorption, Distribution, Metabolism, and Elimination)

The ADME (Absorption, Distribution, Metabolism, and Elimination) properties allow for the documentation of the safety and efficacy of rapid infusion of mAbs. Certain in vitro pharmacology testing for mAbs includes binding to the target antigen, mode of action and downstream effects, and binding to Fc receptors such as FcRn and FcγR. Other aspects of the mAb that are important to characterize include an assessment of effector functions such as ADCC and CDC, molecule characteristics such as charge, pI, hydrophobicity, glycosylation, and preliminary assessments of off-target binding using in vitro methods such as BV ELISA Second Pass Testing In general, when a demonstration of mAb product comparability is performed and presented to the FDA, the results of a rigorous physico-chemical characterization and in vitro functional comparisons may dictate whether additional data (e.g., pre-clinical and/or clinical data) may be needed or permitted.[88]

If necessary, in vitro and animal toxicology/efficacy studies may be performed. Animal studies are often performed to measure important PK parameters such as $C_{max}$ and such studies can conduct $C_{max}$ product comparability between normal infusion and RI methods of intravenous administration of mAbs. The plasma concentration of mAbs can vary abruptly and to a great extent, which cannot be explained by normal physiological or assay variability. Future studies may elucidate this phenomenon and determine its relevance for clinical practice.[85, 89-91] If $C_{max}$ comparability testing is not conclusive, and they can be highly variable, the following tests may be necessary. They include measurement of characteristics similar to that performed by Regeneron in support of an EUA for its COVID mAb cocktail, as detailed below.[59]

Antiviral Activity

In a SARS-CoV-2 virus neutralization assay in Vero E6 cells, Casirivimab, imdevimab, and casirivimab and imdevimab together neutralized SARS-CoV-2 (USA-WA1/2020 isolate) with EC50 values of 37.4 pM (0.006 µg/mL), 42.1 pM (0.006 µg/mL), and 31.0 pM (0.005 µg/mL) respectively, Antibody-dependent cell-mediated cytotoxicity (ADCC) and antibody-dependent cellular phagocytosis (ADCP) were assessed using Jurkat target cells expressing SARS-CoV-2 spike protein. Casirivimab, imdevimab and casirivimab and imdevimab together mediated ADCC with human natural killer (NK) effector cells. Casirivimab, imdevimab and casirivimab and imdevimab together mediated ADCP with human macrophages. Casirivimab, imdevimab and casirivimab and imdevimab together did not mediate complement-dependent cytotoxicity in cell-based assays.

Antibody Dependent Enhancement (ADE) of Infection

The potential of casirivimab and of imdevimab to mediate viral entry was assessed in immune cell lines co-incubated with recombinant vesicular stomatitis virus (VSV) virus-like particles (VLP) pseudotyped with SARS-CoV-2 spike protein at concentrations of mAb(s) down to approximately 10-fold below the respective neutralization EC50 values. Casirivimab and imdevimab together and imdevimab alone, but not casirivimab alone, mediated entry of pseudotyped VLP into FcγR2+Raji and FcγR1+/FcγR2+THP1 cells (maximum infection in total cells of 1.34% and 0.24%, respectively, for imdevimab; 0.69% and 0,06%, respectively for casirivimab and imdevimab together), but not any other cell lines tested (IM9, K562, Ramos and U937 cells).

Antiviral Resistance

Escape variants were identified following two passages in cell culture of recombinant VSV encoding SANS-CoV-2 spike protein in the presence of casirivimab or imdevimab individually, but not following two passages in the presence of casirivimab and imdevimab together. Variants which showed reduced susceptibility to casirivimab alone included those with spike protein amino acid substitutions K417E (182-fold), K417N (7-fold); K417R (61-fold), Y453F (>438-fold), L455F (80-fold), E484K (25-fold), F486V (>438-fold) and Q493K (>438-fold), Variants which showed reduced susceptibility to imdevimab alone included substitutions K444N (>755-fold), K444Q (>548-fold), K444T (>1,033-fold), and V445A (548-fold), Casirivimab and imdevimab together showed reduced susceptibility to variants with K444T (6-fold) and V445A (5-fold) substitutions.

In neutralization assays using VSV VLP pseudotyped with spike protein variants identified in circulating SARS-CoV-2, variants with reduced susceptibility to casirivimab alone included those with E406D (51-fold), V445T (107-fold), G476S (5-fold), E484Q (19-fold), G485D (5-fold), F486L (61-fold), F486S (>715-fold), Q493E (446-fold), Q493R (70-fold), and S494P (5-fold) substitutions, and variants with reduced susceptibility to imdevimab alone included those with P337L (5-fold), N439K (463-fold), N439V (4-fold), N440K (28-fold), K4441, (153-fold), K444M (1,577-fold), (I446V (135-fold), N450D (9-fold), Q493R (5-fold), Q498H (17-fold), P499S (206-fold) substitutions. The G476D substitution had an impact (4-fold) on casirivimab and imdevimab together. Substitutions tested concurrently which had reduced susceptibility to casirivimab and imdevimab together included N440K+E484K (21-fold), found in the B.1.619/B.1.625 lineages, and N439K+E484K (23-fold), found in the AV.1 lineage; variants harboring these concurrent substitutions have been detected rarely in the US. Casirivimab and imdevimab individually and together retained neutralization activity against pseudotyped VLP expressing all spike protein substitutions found in the B.1.1.7 lineage (Alpha; UK origin) and against pseudotyped VLP expressing only N501Y found in B.1.1.7 and other circulating lineages (Table 9). Casirivimab and imdevimab together retained neutralization activity against pseudotyped VLP expressing all spike protein substitutions, or individual substitutions K417N. E484K or N501Y, found in the B.1.351 lineage (Beta; South Africa origin), and all spike protein substitutions or key substitutions K417T, E484K, or N501Y, found in the P.1 lineage (Gamma; Brazil origin), although casirivimab alone, but not imdevimab, had reduced activity against pseudotyped VLP expressing K417N or E484K, as indicated above. The E484K substitution is also found in the B.1.526 lineage (Iota; USA [New York] origin). Casirivimab and imdevimab, individually and together, retained neutralization activity against the L452R substitution found in the B.1.427/B.1.429 lineages (Epsilon; USA [California] origin). Casirivimab and imdevimab, individually and together, retained neutralization activity against pseudotyped VLP expressing L452R+T478K substitutions found in the B.1.617.2 and AY.3 lineages (Delta; India origin). Casirivimab and imdevimab together retained neutralization activity against pseudotyped VLP expressing K417N+L452R+T478K, substitutions found in the B.1.617.2 sublineages AY.1/AY.2 (commonly known as "Delta plus"; India origin), although casirivimab alone, but not imdevimab, had reduced activity against pseudotyped VLP expressing K417N+L452R+T478K substitutions, as indicated above. Casirivimab and imdevimab together retained neutralization activity against pseudotyped VLP expressing L452R+E484Q substitutions, found in the B.1.617.1/B.1.617.3 lineages (Kappa/no designation; India origin), although casirivimab alone, but not imdevimab, had reduced activity against pseudotyped VLP expressing E484Q, as indicated above. Casirivimab and imdevimab, individually and together, retained neutralization activity against pseudotyped VLP expressing L452Q+F490S substitutions found in the C.37 lineage (Lambda; Peru origin). Casirivimab and imdevimab together retained activity against pseudotyped VLP expressing individual substitutions R346K, E484K and N501Y, found in the B.1.621/B.1.621.1 (Mu; Colombia origin) lineage.

In a plaque reduction assay, casirivimab and imdevimab together retained activity against authentic SARS-CoV-2 variants of B.1.1.7 (Alpha), B.1.351 (Beta), P.1 (Gamma), B.1.617.1 (Kappa) lineages (Table 10), although casirivimab alone, but not imdevimab, had reduced activity against B.1.351 (5-fold), P.1 (154-fold) and B.1.617.1 (6-fold) variants. It is not known how pseudotyped VLP or authentic SARS-CoV-2 data correlate with clinical outcomes.

Nonclinical Toxicology

In a toxicology study in cynomolgus monkeys, casirivimab and imdevimab had no adverse effects when administered intravenously or subcutaneously. Non-adverse liver findings (minor transient increases in AST and ALT) were observed.

In tissue cross-reactivity studies with casirivimab and imdevimab using human adult and fetal tissues, no binding of clinical concern was detected.

Animal Pharmacologic and Efficacy

Casirivimab and imdevimab administered together has been assessed in rhesus macaque and Syrian golden hamster treatment models of SARS-CoV-2 infection. Therapeutic administration of casirivimab and imdevimab together at 25 mg/kg or 150 mg/kg into rhesus macaques (n=4 for each dosing group) 1-day post infection resulted in approximately 1-2 log 10 reductions in genomic and sub-genomic viral RNA in nasopharyngeal swabs and oral swabs at Day 4 post-challenge in most animals, and reduced lung pathology relative to placebo-treated animals. Therapeutic administration of c-asirivimab and imdevimab together at 5 mg/kg and 50 mg/kg doses to hamsters 1-day post infection resulted in reduced weight loss relative to placebo treated animals. In the prophylactic setting in rhesus macaques, administration of 50 mg/kg casirivimab and imdevimab together prior to challenge with SARS-CoV-2 demonstrated reduction in viral RNA via nasopharyngeal, oral swabs and bronchioalveolar lavage fluid, as well as a reduction in lung inflammation. In the prophylactic setting in hamsters, administration of 0.5 mg/kg, 5 mg/kg, or 50 mg/kg casirivimab and imdevimab together prior to challenge with SARS-CoV-2 protected against weight loss, and reduced percentage of lung area showing pneumonia pathology and severity of lung inflammation, indicative of reduced morbidity in this model. The applicability of these findings to a clinical setting is to be confirmed.

END NOTES AND REFERENCES

1. "Regeneron, GlaxoSmithKline and Eli Lilly COVID-19 drugs prioritized for expedited review," by Kevin Dunleavy, Jun. 30, 2021, https://www.fiercepharma.com/pharma/covid-19-treatments-from-regeneron-lilly-gsk-vir-among-5-prioritized-for-expedited-review.
2. European Commission Identifies 10 Most Promising Treatments for COVID-19, HospiMedica International, Oct. 26, 2021. https://www.hospimedica.com/covid-19/articles/294790274/european-commission-identifies-10-most-promising-treatments-for-covid-19. html.
3. 50 of 2020's best-selling pharmaceuticals, by Brian Buntz, May 14, 2021, Drug Discovery & Development. https://www.drugdiscoverytrends.com/50-of-2020s-best-selling-pharmaceuticals/.
4. Gklinos, P.; Papadopoulou, M.; Stanulovic, V.; Mitsikostas, D. D.; Papadopoulos, D. Monoclonal Antibodies as Neurological Therapeutics. Pharmaceuticals 2021, 14, 92. Https://doi.org/10.3390/ph14020092.
5. ClinicalTrials.gov. A Study to Evaluate Safety, Tolerability, and Efficacy of Lecanemab in Subjects with Early Alzheimer's Disease. 2020. Available online: https://clinicaltrials.gov/ct2/show/NCT01767311,NCT01767311 (accessed on 20 Nov. 2020)

6. Schofield, D. J.; Irving, L.; Calo, L.; Bogstedt, A.; Rees, G.; Nuccitelli, A.; Narwal, R.; Petrone, M.; Roberts, J.; Brown, L.; et al. Preclinical development of a high affinity α-synuclein antibody, MEDI1341, that can enter the brain, sequester extracellular α-synuclein and attenuate α-synuclein spreading in vivo. Neurobiol. Dis. 2019, 132, 104582.
7. Affinity-matured 'aquaporumab' anti-aquaporin-4 antibody for therapy of seropositive neuromyelitis optica spectrum disorders; October 2019; Neuropharmacology 162:107827; DOI:10.1016/j.neuropharm.2019.107827.
8. Efficacy and Safety of Rozanolixizumab in Moderate to Severe Generalized Myasthenia Gravis
A Phase 2 Randomized Control Trial; Vera Bril, Michael Benatar, Henning Andersen, John Vissing, Melissa Brock, Bernhard Greve, Peter Kiessling, Franz Woltering, Laura Griffin, Peter Van den Bergh, on behalf of the MG0002 Investigators; Neurology February 2021, 96 (6) e853-e865; DO I: 10.1212/WNL.0000000000011108.
9. Gedeon, P. C.; Streicker, M. A.; Schaller, T. H.; Archer, G. E.; Jokinen, M. P.; Sampson, J. H. GLP toxicology study of a fully-human T cell redirecting CD3:EGFRvIII binding immunotherapeutic bispecific antibody. PLoS ONE 2020, 15, e0236374.
10. "Rezurock is approved with more transplant agents in pipeline," Jul. 22, 2021, AIS Health, Member: RADAR on Drug Benefits,
11. https://products.sanofi.us/thymoglobulin/thymoglobulin.pdf
12. http://labeling.pfizer.com/ShowLabeling.aspx?id=525
13. https://infusioncenter.org
14. https://www.phe.gov/emergency/events/COVID19/therapeutics/Pages/Infusion-Center-Model. aspx
15. https://www.fda.gov/vaccines-blood-biologics/vaccines/emergency-use-authorization-vaccines-explained
16. See, for example, Ryman J T, Meibohm B. Pharmacokinetics and Monoclonal Antibodies. CPT Pharmacometrics Syst Pharmacol. 2017 September; 6(9): 576-588; Dirks N L, Meibohm B. Population pharmacokinetics of therapeutic monoclonal antibodies. Clin. Pharamcokinet. 2010; 49: 633-659; and Zhao L, Li P, Li Z, Roy P, Sahajwalla C G; The antibody drug absorption following subcutaneous or intramuscular administration and its mathematical description by coupling physiologically based absorption process with the conventional compartment pharmacokinetic model. J. Clin. Pharmacol. 2013; 53: 314-325.
17. https://www.regeneron.com/downloads/treatment-covid19-eua-fact-sheet-for-hcp.pdf
18. https://www.covid19treatmentguidelines.nih.gov/therapies/anti-sars-cov-2-antibody-products/anti-sars-cov-2-monoclonal-antibodies/19.
19. https://www.gsk.com/en-gb/media/press-releases/primary-endpoint-met-in-comet-tail-phase-iii-trial-evaluating-intramuscular-administration-of-sotrovimab-for-early-treatment-of-covid-19/
20. See, e.g., Salinas B, Sathish H, Bishop S, Harn N, Carpenter J. Understanding and modulating opalescence and viscosity in a monoclonal antibody formulation. J Pharm Sci. 2010; 99(1): 82 93.
21. https://www.merck.com/news/merck-and-ridgebacks-investigational-oral-antiviral-molnupiravir-reduced-the-risk-of-hospitalization-or-death-by-approximately-50-percent-compared-to-placebo-for-patients-with-mild-or-moderat/
22. "FDA advisory panel narrowly endorses Merck's oral Covid treatment pill, despite reduced efficacy and safety questions," Spencer Kimball, CNBC Health and Science, Nov. 30, 2021. https://www.cnbc.com/2021/11/30/fda-advisory-panel-narrowly-endorses-mercks-oral-covid-treatment-pill-despite-reduced-efficacy.html
23. Ibid.
24. https://www.pfizer.com/news/press-release/press-release-detail/pfizers-novel-covid-19-oral-antiviral-treatment-candidate
25. Eight lingering questions about the new Covid pills from Merck and Pfizer, STAT Health, Nov. 15, 2021. https://www.statnews.com/2021/11/15/8-lingering-questions-about-the-new-covid-pills-from-merck-and-pfizer/
26. Ibid.
27. Ibid.
28. https://investor.regeneron.com/news-releases/news-release-details/phase-3-trial-shows-regen-covtm-casirivimab-imdevimab-antibody
29. Reynald Castaneda, Oct. 5, 2021, "Oral Covid-19 drugs: Merck's molnupiravir and its closest rivals," Clinical Trials Arena. https://www.clinicaltrialsarena.com/analysis/oral-covid-19-drugs-molnupiravir/
30. Katella, Kathy, "9 Things You Need to Know About the New COVID-19 Pill," YaleMedicine, Oct. 11, 2021, https://www.yalemedicine.org/news/9-things-to-know-about-covid-pill.
31. N Engl J Med 2010; 362:1553-5. Osterberg L, Blaschke T. Adherence to medication. N Engl J Med 2005; 353: 487-97.
32. Bozzette S A, Ake C F, Tam H K, Chang S W, Louis T A. Cardiovascular and cerebrovascular events in patients treated for human immunodeficiency virus infection. N Engl J Med. 2003; 348(8):702-710; Hruz P W. HIV protease inhibitors and insulin resistance: lessons from in-vitro, rodent and healthy human volunteer models. Curr Opin HIV AIDS. 2008; 3(6):660-665. Kotler D P. HIV and antiretroviral therapy: lipid abnormalities and associated cardiovascular risk in HIV-infected patients. J Acquir Immune Defic Syndr. 2008; 49(Suppl 2):579-585. Soontornniyomkij V, Umlauf A, Chung S A, et al. HIV protease inhibitor exposure predicts cerebral small vessel disease. AIDS. 2014; 28(9):1297-1306.
33. "What to Know About COVID-19 Pills and What They Mean for the Pandemic Fight," Nov. 16, 2021. NBC Channel 5 Chicago, https://www.nbcchicago.com/news/coronavirus/what-to-know-about-covid-19-pills-and-what-they-mean-for-the-pandemic-fight/2686151/
34. https://nhia.org/NEWS/BAM-PILOT-PROGRAM/35.
Minnema L A, Giezen T J, Souverein P C, Egberts T C G, Leufkens H G M, Gardarsdottir H. Exploring the Association between Monoclonal Antibodies and Depression and Suicidal Ideation and Behavior: A VigiBase Study. Drug Saf. 2019 July; 42(7):887-895. doi: 10.1007/s40264-018-00789-9. PMID: 30617497; PMCID: PMC6581921.
36. https://www.eviq.org.au/dose-mod-gradings/standard-ctcae/infusion-related-reaction-irr
37. Fact Sheet for Health Care Providers Emergency Use Authorization (EUA) of Bamlanivimab and Etesevimab, FDA, https://www.fda.gov/media/145802/download
38. Anderson, T. S., O'Donoghue, A. L., Dechen, T. et al. Uptake of Outpatient Monoclonal Antibody Treatments for COVID-19 in the United States: a Cross-Sectional Analysis. J GEN INTERN MED (2021). https://doi.org/10.1007/s11606-021-07109-5
39. https://www.whitehouse.gov/covidplan/
40. Ibid.

41. https://www.cms.govinewsroom/press-releases/cms-increases-medicare-payment-covid-19-monoclonal-antibody-infusions
42. J Ryan Bariola, et al., Impact of Bamlanivimab Monoclonal Antibody Treatment on Hospitalization and Mortality Among Nonhospitalized Adults With Severe Acute Respiratory Syndrome Coronavirus 2 Infection, Open Forum Infectious Diseases, Volume 8, Issue 7, July 2021, ofab254, https://doi.org/10.1093/ofid/ofab254.
43. Regina Herzlinger and Barak Richman, "Preparing Hospitals for the Next Pandemic," Harvard Business Review, Jun. 10, 2021. https://hbr.org/2021/06/preparing-hospitals-for-the-next-pandemic
44. https://newsroom.regeneron.com/index.php/static-files/a7173b5a-28f3-45d4-bede-b97370bd03f8
45. Cohen M S, Nirula A, Mulligan M J, et al. Effect of Bamlanivimab vs Placebo on Incidence of COVID-19 Among Residents and Staff of Skilled Nursing and Assisted Living Facilities: A Randomized Clinical Trial. JAMA. 2021; 326(1):46-55. doi:10.1001/jama.2021.8828
46. https://clinicaltrials.gov/ct2/show/study/NCT00719472
47. Anticancer Research, March 2020, vol. 40, no. 3, 1201-1218. https://ar.iiarjournals.org/content/anticanres/40/3/1201.full.pdf
48. Ibid.
49. https://www.thelancet.com/journals/lancet/article/PIIS0140-6736(19)30036-4/fulltext.
50. https://www.aha.org/system/files/media/file/2020/11/operation-warp-speed-playbook-allocation-distribution-covid-19-therapeutic-medications.pdf
51. https://www.fda.gov/media/145802/download
52. https://www.regeneron.com/downloads/treatment-covid19-eua-fact-sheet-for-hcp.pdf
53. https://www.fda.gov/media/150321/download
54. https://www.fda.gov/media/149534/download
55. Gupta et al., "Early Treatment for Covid-19 with SARS-CoV-2 Neutralizing Antibody Sotrovimab," N Engl J Med 2021; 385:1941-1950, Nov. 18, 2021. https://www.nejm.org/doi/full/10.1056/NEJMoa2107934
56. https://www.fda.gov/media/149534/download
57. https://www.covid19.lilly.com/bamlanivimab/hcp/dosing-administration
58. Shire S J. Stability of monoclonal antibodies (mAbs). In: Monoclonal Antibodies. Amsterdam, the Netherlands: Elsevier; 2015:45-92. https://doi.org/10.1016/B978-0-08-100296-4.00003-8.
59. Mahler H-C, Friess W, Grauschopf U, Kiese S. Protein aggregation: pathways, induction factors and analysis. J Pharm Sci. 2009; 98(9):2909-2934.
60. Wang W. Protein aggregation and its inhibition in biopharmaceutics. Int J Pharm. 2005; 289(1-2): 1-30.
61. Uchiyama S. Liquid formulation for antibody drugs. Biochim Biophys Acta. 2014; 1844(11):2041-2052.
62. Chi E Y, Krishnan S, Randolph T W, Carpenter J F. Physical stability of proteins in aqueous solution: mechanism and driving forces in nonnative protein aggregation. Pharm Res. 2003; 20(9):1325-1336.
63. Hawe A, Kasper J C, Friess W, Jiskoot W. Structural properties of monoclonal antibody aggregates induced by freeze-thawing and thermal stress. Eur J Pharm Sci. 2009; 38(2):79-87.
64. Rosenberg A S. Effects of protein aggregates: an immunologic perspective. AAPS J. 2006; 8(3):E501-E507.
65. Wang M, Li Y, Srinivasan P, et al. Interactions between biological products and product packaging and potential approaches to overcome them. AAPS PharmSciTech. 2018; 19(8):3681-3686.
66. Le Basle Y, Chennell P, Tokhadze N, Astier A, Sautou V. Physiochemical stability of monoclonal antibodies: a review. J Pharmaceutical Sci. 2020; 109:169-190
67. Mehta S B, Lewus R, Bee J S, Randolph T W, Carpenter J F. Gelation of a monoclonal antibody at the silicone oilewater interface and subsequent rupture of the interfacial gel results in aggregation and particle formation. J Pharm Sci. 2015; 104(4):1282-1290.
68. Masato A, Kiichi F, Uchiyama S. Suppression of Methionine Oxidation of a Pharmaceutical Antibody Stored in a Polymer-Based Syringe. J Pharm Sci. 2016 February; 105(2):623-629. doi: 10.1002/jps.24675. Epub 2016 Jan. 11. PMID: 26462145.
69. Berrill A, Biddlecombe J, Bracewell D. Product quality during manufacture and supply. In: Peptide and Protein Delivery. Amsterdam, the Netherlands: Elsevier; 2011: 313-339. https://doi.org/10.1016/B978-0-12-384935-9.10013-6.
70. Yang R, Jain T, Lynaugh H, et al. Rapid assessment of oxidation via middledown LCMS correlates with methionine side-chain solvent-accessible surface area for 121 clinical stage monoclonal antibodies. MAbs. 2017; 9(4): 646-653.
71. Li S, Nguyen T H, Schoneich C, Borchardt R T. Aggregation and precipitation of human relaxin induced by metal-catalyzed oxidation. Biochemistry. 1995; 34(17):5762-5772.
72. Horn J, Schanda J, Friess W. Impact of fast and conservative freeze-drying on product quality of protein-mannitol-sucrose-glycerol lyophilizates. Eur J Pharm Biopharm. 2018; 127:342-354.
73. Barnard J G, Singh S, Randolph T W, Carpenter J F. Subvisible particle counting provides a sensitive method of detecting and quantifying aggregation of monoclonal antibody caused by freeze-thawing: insights into the roles of particles in the protein aggregation pathway. J Pharm Sci. 2011; 100(2):492-503
74. Kueltzo L A, Wang W, Randolph T W, Carpenter J F. Effects of solution conditions, processing parameters, and container materials on aggregation of a monoclonal antibody during freeze-thawing. J Pharm Sci. 2008; 97(5): 1801-1812.
75. Schermeyer M-T, W€oll A K, Kokke B, Eppink M, Hubbuch J. Characterization of highly concentrated antibody solutionea toolbox for the description of protein long-term solution stability. MAbs. 2017; 9(7):1169-1185.
76. Hauptmann A, Podgor_sek K, Kuzman D, Sr_ci_c S, Hoelzl G, Loerting T. Impact of buffer, protein concentration and sucrose addition on the aggregation and particle formation during freezing and thawing. Pharm Res. 2018; 35(5):101
77. Nicoud L, Jagielski J, Pfister D, et al. Kinetics of monoclonal antibody aggregation from dilute toward concentrated conditions. J Phys Chem B. 2016; 120(13): 3267-3280.
78. Harn N, Allan C, Oliver C, Middaugh C R. Highly concentrated monoclonal antibody solutions: direct analysis of physical structure and thermal stability. J Pharm Sci. 2007; 96(3):532-546.
79. Sreedhara A, Glover Z K, Piros N, Xiao N, Patel A, Kabakoff B. Stability of IgG1 monoclonal antibodies in intravenous infusion bags under clinical in-use conditions. J Pharm Sci. 2012; 101(1):21-30.
80. https://www.fda.gov/media/145611/download
81. https://www.creative-biolabs.com/drug-discovery/therapeutics/antibody-stability-analysis.htm 82. Munson E S. Air from IV bags may pose danger; venous embolism comes from many causes. APSF Newsletter, 1993; 8(2).
83. Ogawa C, Inoue M, Yatabe M, Nagayama Y, Gomi H, Nakadate K, Adachi S, Yachi Y, Itoh T, Analysis of inline-filter blockage with trastuzumab formulation using scanning-electron microscopy. Biomed Pharmacother, 2019; 112:108711.
84. Wan H. What ADME tests should be conducted for preclinical studies? ADMET & DMPK. 2013; 1(3):19-28.
85. Keizer R J, Huitema A D, Schellens J H, Beijnen J H. Clinical pharmacokinetics of therapeutic monoclonal antibodies. Clin. Pharmacokinet. 2010; 49:493-507.
86. Lobo E D, Hansen R J, & Balthasar J P. Antibody pharmacokinetics and pharmacodynamics. J. Pharm. Sci. 93, 2645-2668 (2004).
87. Kamath A V. Translational pharmacokinetics and pharmacodynamics of monoclonal antibodies. Drug Discov Today Technol. 2016; 21-22:75-83.
88. FDA. Points to Consider in the Manufacture and Testing of Monoclonal Antibody Products for Human Use. 1997
89. Wang W, Wang E Q, Balthasar J P. Monoclonal antibody pharmacokinetics and pharmacodynamics. Clin Pharmacol Ther. 2008; 84:548-58.
90. Dirks N L, Meibohm B. Population pharmacokinetics of therapeutic monoclonal antibodies. Clin Pharmacokinet. 2010; 49:633-59.
91. Dostalek M, Gardner I, Gurbaxani B M, et al. Pharmacokinetics, pharmacodynamics and physiologically-based pharmacokinetic modelling of monoclonal antibodies. Clin Pharmacokinet. 2013; 52:83-124.
92. https://www.rituxan-hcp.com/nhl-clUdosing-and-administration/rituxan-administration/rituxan-infusion.html
93. rituxan-hcp.com

EQUIVALENTS

It is to be understood that while the disclosure has been described in conjunction with the description thereof, and the foregoing description is intended to illustrate and not limit the scope of the invention(s). Other aspects, advantages, and modifications are within the scope of the following claims.

What is claimed is:

1. A method for administering a monoclonal and/or polyclonal antibody treatment via a rapid infusion device, the method comprising:
   administering by intravenous infusion a volume of solution comprising one or more monoclonal and/or polyclonal antibodies to a patient using a rapid infusion device, wherein the rapid infusion device comprises a pump, a tubing line or lines, and an air venting mechanism without a dripping chamber or a drip pan to prevent delivery of air bubbles to the patient, wherein the tubing line or lines fluidly connect (i) an intravenous (IV) bag or other receptacle containing the volume of solution to the pump and (ii) the pump to the patient, for intravenous delivery of the volume of solution to the patient, wherein the pump administers the volume of solution to the patient at a flow rate of at least 10 mL/min.

2. The method of claim 1, wherein the one or more monoclonal and/or polyclonal antibodies comprises a monoclonal and/or polyclonal antibody (or cocktail of antibodies) for the treatment of one or more members selected from the group consisting of: cancer, a neurological disease or condition; dermatitis; psoriasis; asthma or other respiratory disease; macular degeneration; an autoimmune disease; cytokine release syndrome; Castelman disease; a disease caused by a pathogen; and organ and/or tissue transplant.

3. The method of claim 1, wherein the one or more monoclonal and/or polyclonal antibodies comprises a member selected from the group consisting of the following:
   an anti-inflammatory; an anti-cancer; an anti-cancer and anti-viral; palivizumab; and abciximab.

4. The method of claim 1, wherein the one or more monoclonal and/or polyclonal antibodies comprises a monoclonal and/or polyclonal antibody (or cocktail of antibodies) for the treatment of COVID-19.

5. The method of claim 1, wherein the one or more monoclonal and/or polyclonal antibodies comprises a monoclonal and/or polyclonal antibody (or cocktail of antibodies) for the treatment of a neurological disease or condition.

6. The method of claim 1, wherein the one or more monoclonal antibodies comprises one or more members selected from the group consisting of:
   pembrolizumab; nivolumab; bevacizumab; ocrelizumab; rituximab; daratumumab; pertuzumab;
   trastuzumab; infliximab; tocilizumab; atezolizumab; tositumomab-1131; olaratumab; ;
   basiliximab; ibritumomab tiuxetan; cetuximab; natalizumab; panitumumab; ranibizumab ;
   eculizumab ; ofatumumab ; belimumab; ipilimumab ; pertuzumab ; raxibacumab; obinutuzumab;
   siltuximab; ramucirumab; vedolizumabdisease; alemtuzumab, necitumumab; dinutuximab;
   elotuzumab; reslizumab; bezlotoxumab; obiltoxaximab; avelumab; and durvalumab.

7. The method of claim 1, wherein the method is performed for the treatment of an organ and/or tissue transplant patient.

8. The method of claim 1, wherein the rapid infusion device comprises a flow control feature that limits flow of fluid to the patient to no greater than a predetermined maximum flow rate.

9. The method of claim 1, wherein the rapid infusion device delivers the volume of solution to the patient at a rate that approximates a predetermined fixed rate.

10. The method of claim 1, comprising using a disposable infusion set for connection to the rapid infusion device, wherein the disposable infusion set comprises one or more members of the group consisting of: a needle, one or more lengths of tubing, and an adhesive support.

11. The method of claim 1, wherein the rapid infusion device comprises an elastomeric pump, wherein the pump comprises the receptacle containing the volume of solution, and wherein the tubing line or lines fluidly connect the pump and, therefore, the receptacle containing the volume of solution, to the patient, for intravenous delivery of the volume of solution to the patient.

12. The method of claim 1, wherein the rapid infusion device comprises a heater.

13. The method of claim 1, wherein the rapid infusion device comprises a filter for filtering out particles from the volume of solution prior to, and upstream of, delivery of the filtered solution to the patient.

14. The method of claim 13, wherein the filter has a size small enough to catch the particles, wherein the filter has a size below 170 microns.

15. The method of claim 1, wherein the rapid infusion device is portable and/or is designed for a single use.

16. The method of claim 1, wherein the one or more monoclonal and/or polyclonal antibodies comprises a monoclonal and/or polyclonal antibody (or cocktail of antibodies) for the treatment of cancer.

17. The method of claim 1, wherein the one or more monoclonal and/or polyclonal antibodies comprises a monoclonal and/or polyclonal antibody (or cocktail of antibodies) for the treatment of one or more members selected from the group consisting of dermatitis or psoriasis.

18. The method of claim 1, wherein the one or more monoclonal and/or polyclonal antibodies comprises a monoclonal and/or polyclonal antibody (or cocktail of antibodies) for the treatment of asthma or other respiratory disease.

19. The method of claim 1, wherein the one or more monoclonal and/or polyclonal antibodies comprises a monoclonal and/or polyclonal antibody (or cocktail of antibodies) for the treatment of macular degeneration.

20. The method of claim 1, wherein the one or more monoclonal and/or polyclonal antibodies comprises a monoclonal and/or polyclonal antibody (or cocktail of antibodies) for the treatment of an autoimmune disease.

21. The method of claim 1, wherein the one or more monoclonal and/or polyclonal antibodies comprises a monoclonal and/or polyclonal antibody (or cocktail of antibodies) for the treatment of cytokine release syndrome.

22. The method of claim 1, wherein the one or more monoclonal and/or polyclonal antibodies comprises a monoclonal and/or polyclonal antibody (or cocktail of antibodies) for the treatment of Castelman disease.

23. The method of claim 1, wherein the one or more monoclonal and/or polyclonal antibodies comprises a monoclonal and/or polyclonal antibody (or cocktail of antibodies) for the treatment of a disease caused by a pathogen.

24. The method of claim 23, wherein the pathogen comprises SARS-CoV-2.

25. The method of claim 1, wherein the method comprises administering at least a portion of the volume of solution to the patient at a flow rate of at least 15 mL/min.

26. The method of claim 1, wherein the method comprises administering at least a portion of the volume of solution to the patient at a flow rate of at least 30 mL/min.

27. A method for administering a monoclonal and/or polyclonal antibody treatment via a rapid infusion device, the method comprising:
administering by intravenous infusion a volume of solution comprising one or more monoclonal and/or polyclonal antibodies to a patient using a rapid infusion device, wherein the rapid infusion device comprises a pump, a tubing line or lines, and an air venting mechanism without a dripping chamber or a drip pan to prevent delivery of air bubbles to the patient, wherein the tubing line or lines fluidly connect (i) an intravenous (IV) bag or other receptacle containing the volume of solution to the pump and (ii) the pump to the patient, for intravenous delivery of the volume of solution to the patient, wherein all three of (a), (b), and (c), as follows, applies:
(a) the pump administers the volume of solution to the patient at a flow rate of at least 10 mL/min;
(b) the pump administers the volume of solution at a dosing rate of at least 35 mg of the one or more monoclonal and/or polyclonal antibodies per minute and/or at a total [mAb(s) and/or pAb(s)] concentration of less than or equal to 20 mg/mL [total mg mAb(s) and/or pAb(s) per mL IV solution]; and
(c) administration of the volume of solution to the patient is completed in no more than 30 minutes.

28. A method for administering a monoclonal and/or polyclonal antibody treatment via a rapid infusion device, the method comprising:
administering by intravenous infusion a volume of solution comprising one or more monoclonal and/or polyclonal antibodies to a patient using a rapid infusion device, wherein the rapid infusion device comprises a pump a tubing line or lines, wherein the tubing line or lines fluidly connect (i) an intravenous (IV) bag or other receptacle containing the volume of solution to the pump and (ii) the pump to the patient, for intravenous delivery of the volume of solution to the patient,
wherein the pump is capable of administering administers the volume of solution to the patient at a flow rate of at least 10 mL/min,
wherein the flow rate is capable of being adjusted,
wherein the rapid infusion device comprises an air venting mechanism without a dripping chamber or a drip pan to prevent delivery of air bubbles to the patient, and
wherein the rapid infusion device comprises a temperature control device, thereby enhancing stability of the monoclonal and/or polyclonal antibodies being administered to the patient.

* * * * *

UNITED STATES PATENT AND TRADEMARK OFFICE
CERTIFICATE OF CORRECTION

| | |
|---|---|
| PATENT NO. | : 11,806,397 B2 |
| APPLICATION NO. | : 17/589068 |
| DATED | : November 7, 2023 |
| INVENTOR(S) | : Regina E. Herzlinger |

It is certified that error appears in the above-identified patent and that said Letters Patent is hereby corrected as shown below:

In the Claims

At Column 50, Claim number 6, Line number 30, replace the word "vedolizumabdisease" with the word --vedolizumab--.

Signed and Sealed this
Nineteenth Day of December, 2023

Katherine Kelly Vidal
*Director of the United States Patent and Trademark Office*